US005536636A

United States Patent [19]
Freeman, Jr. et al.

[11] Patent Number: 5,536,636
[45] Date of Patent: Jul. 16, 1996

[54] METHODS FOR IDENTIFYING A TYROSINE PHOSPHATASE ABNORMALITY ASSOCIATED WITH NEOPLASTIC DISEASE

[75] Inventors: Robert M. Freeman, Jr.; Jorge Plutzky, both of Boston; Benjamin G. Neel, Wayland; Robert D. Rosenberg, Brookline, all of Mass.

[73] Assignees: Beth Israel Hospital, Boston; Massachusetts Institute of Technology, Cambridge, both of Mass.

[21] Appl. No.: 202,389

[22] Filed: Feb. 28, 1994

Related U.S. Application Data

[63] Continuation-in-part of Ser. No. 983,926, Dec. 1, 1992, abandoned, which is a continuation-in-part of Ser. No. 829,141, Jan. 31, 1992, abandoned, which is a continuation-in-part of Ser. No. 721,112, Jun. 26, 1991, abandoned.

[51] Int. Cl.$^6$ ............ C07H 21/64; C12P 19/34; C12Q 1/68
[52] U.S. Cl. ............ 435/6; 435/91.1; 435/91.2; 536/24.3; 536/24.31; 935/77; 935/78
[58] Field of Search ............ 435/6, 91.1, 91.2; 536/24.3, 24.31; 935/77, 78

[56] References Cited

FOREIGN PATENT DOCUMENTS

WO91/13989  9/1991  WIPO.

OTHER PUBLICATIONS

Suijkerbuijk et al. Am. J. Hum. Genet. 48:269–273, 1991.
Perré et al. Hum. Genet. 87:231–233, 1991.
Koch, C. Anne et al., "SH2 and SH3 Domains: Elements that Control Interactions of Cytoplasmic Signaling Proteins", *Science* 252:668–674 (May 1991).
Tonks, N. K., "Protein Phosphateses: Key Players in the Regulation of Cell function", *Current Opinion in Cell Biology* 2:1114–1124 (1990).
Hunter, Tony, "Protein–Tyrosine Phosphatases: The Other Side of the Coin", *Cell* 58:1013–1016 (1989).
Gewirtz, Alan M. and Hoffman, Ronald, "Human Megakaryocyte Production: Cell Biology and Clinical Considerations", *Hematology/Oncology Clinics of North America* 4(1):43–64 (Feb. 1990).
Shen, Shi–Hsiang et al., "A protein–tyrosine phosphatase with sequence similarity to the SH2 domain of the protein–tyrosine kinases", *Nature* 352:736–739, (Aug. 1991), including correction page, *Nature* 353:868 (Oct. 1991).
Yi, Taolin et al., "Protein Tyrosine Phosphatase Containing SH2 domains: Characterization, Preferential Expression in Hematopoietic Cells, and Localization to Human Chromosome 12p12–p13", *Molecular and Cellular Biology* 12(2):836–848 (Feb. 1992).
Plutzky, Jorge et al., "Isolation of a src homology 2–containing tyrosine phosphatase", *Proc. Natl. Acad. Sci. USA* 89:1123–1127 (Feb. 1992).
Lathe, R., "Synthetic Oligonucleotide Probes Deduced from Amino Acid Sequence Data Theoretical and Practical Considerations", *J. Mol. Biol.* 183:1–12 (1985).
Chernoff, Jonathan et al., "Cloning of a cDNA for a major human protein–tyrosine–phosphatase", *Proc. Natl. Acad. Sci. USA* 87:2735–2739 (Apr. 1990).

(List continued on next page.)

*Primary Examiner*—W. Gary Jones
*Assistant Examiner*—Paul B. Tran
*Attorney, Agent, or Firm*—Hamilton, Brook, Smith & Reynolds

[57] ABSTRACT

The present invention relates to the isolation of genes encoding novel protein tyrosine phosphatases (PTPs) having SH2 domains, the nucleic acid sequences isolated, and the encoded phosphatases. The invention further relates to methods of altering tyrosine phosphatase activities encoded by the novel phosphatases. By altering (i.e., increasing or decreasing) tyrosine phosphatase activity, one can alter megakaryocyte cell function, and thereby alter platelet production. Alteration of the genes is associated with neoplastic disease.

8 Claims, 16 Drawing Sheets

OTHER PUBLICATIONS

Charbonneau, Harry et al., "Human placenta protein–tyrosine–phosphatase: Amino acid sequence and relationship to a family of receptor–like proteins", *Proc. Natl. Acad. Sci. USA* 86:5252–5256 (Jul. 1989).

Fischer, E. H. et al., "Protein Tyrosine Phosphatases: A Diverse Family of Intracellular and Transmembrane Enzymes", *Science* 253:401–406 (Jul. 1991).

Perkins, Lizabeth A. et al., "*corkscrew* Encodes a Putative Protein Tyrosine Phosphatase That Functions to Transducer the Terminal Signal from the Receptor Tyrosine Kinase torso", *Cell* 70:225–236 (Jul. 1992).

Matthews, R. J., et al., "Characterization of Hematopoietic Intracellular Protein Tyrosine Phosphatases: Description of a Phosphatase Containing an SH2 Domain and Another Enriched in Proline–, Glutamic Acid–, Serine–, and Threonine–Rich Sequences", *Mol. and Cell. Biol.* 12(5):2396–2405 (May 1992).

Feng, G–S., et al., "SH2–Containing Phosphotyrosine phosphatase as a Target of Protein–Tyrosine Kinases", *Science* 259:1607–1611 (Mar. 1993).

Vogel, W., et al., "Activation of a Phosphotyrosine Phosphatase by Tyrosine Phosphorylation", *Science* 259:1611–1614 (Mar. 1993).

Ahmad, S., et al., "A widely expressed human protein–tyrosine phosphatase containing src homology 2 domains", *Proc. Natl. Acad. Sci. USA* 90:2197–2201 (Mar. 1993).

Songyang, Z., et al., "SH2 Domains Recognize Specific Phosphopeptide Sequences", *Cell* 72:767–778 (Mar. 1993).

Freeman, Robert M., et al., "Identification of a human src homology 2–containing protein–tyrosine–phosphatase: A putative homolog of Drosophila corkscrew", *Proc. Natl. Acad. Sci. USA* 89:11239–11243 (1992).

```
CGGCAGAACT GGGACCACCG GGGGTGGTGA GGCGGCCCGG CACTGGGAGC TGCATCTGAG      60

GCTTAGTCCC TGAGCTCTCT GCCTGCCCAG ACTAGCTGCA CCTCCTCATT CCCTGCGCCC     120

CCTTCCTCTC CGGAAGCCCC CAGG ATG GTG AGG TGG TTT CAC CGA GAC CTC       171
                          Met Val Arg Trp Phe His Arg Asp Leu
                            1             5

AGT GGG CTG GAT GCA GAG ACC CTG CTC AAG GGC CGA GGT GTC CAC GGT      219
Ser Gly Leu Asp Ala Glu Thr Leu Leu Lys Gly Arg Gly Val His Gly
 10              15                  20                  25

AGC TTC CTG GTC TGG CCC AGT CGC AAG AAC CAG GGT GAC TTC TCG CTC      267
Ser Phe Leu Val Trp Pro Ser Arg Lys Asn Gln Gly Asp Phe Ser Leu
             30                  35                  40

TCC GTC AGG GTG GGG GAT CAG GTG ACC CAT ATT CGG ATC CAG AAC TCA      315
Ser Val Arg Val Gly Asp Gln Val Thr His Ile Arg Ile Gln Asn Ser
         45                  50                  55

GGG GAT TTC TAT GAC CTG TAT GGA GGG GAG AAG TTT GCG ACT CTG ACA      363
Gly Asp Phe Tyr Asp Leu Tyr Gly Gly Glu Lys Phe Ala Thr Leu Thr
     60                  65                  70

GAG CTG GTG GAG TAC TAC ACT CAG CAG CAG GGT GTG GTG CAG GAC CGC      411
Glu Leu Val Glu Tyr Tyr Thr Gln Gln Gln Gly Val Val Gln Asp Arg
 75                  80                  85

GAC GGC ACC ATC ATC CAC CTC AAG TAC CCG CTG AAC TGC TCC GAT CCC      459
Asp Gly Thr Ile Ile His Leu Lys Tyr Pro Leu Asn Cys Ser Asp Pro
 90                  95                 100                 105

ACT AGT GAG AGG TGG TAC CAT GGC CAC ATG TCT GGC GGG CAG GCA GAG      507
Thr Ser Glu Arg Trp Tyr His Gly His Met Ser Gly Gly Gln Ala Glu
             110                 115                 120

ACG CTG CTG CAG GCC AAG GGC GAG CCC TGG ACG TTT CTT GTG CGT GAG      555
Thr Leu Leu Gln Ala Lys Gly Glu Pro Trp Thr Phe Leu Val Arg Glu
         125                 130                 135

AGC CTC AGC CAG CCT GGA GAC TTC GTG CTT TCT GTG CTC AGT GAC CAG      603
Ser Leu Ser Gln Pro Gly Asp Phe Val Leu Ser Val Leu Ser Asp Gln
     140                 145                 150

CCC AAG GCT GGC CCA GGC TCC CCG CTC AGG GTC ACC CAC ATC AAG GTC      651
Pro Lys Ala Gly Pro Gly Ser Pro Leu Arg Val Thr His Ile Lys Val
 155                 160                 165

ATG TGC GAG GGT GGA CGC TAC ACA GTG GGT GGT TTG GAG ACC TTC GAC      699
Met Cys Glu Gly Gly Arg Tyr Thr Val Gly Gly Leu Glu Thr Phe Asp
170                 175                 180                 185

AGC CTC ACG GAC CTG GTG GAG CAT TTC AAG AAG ACG GGG ATT GAG GAG      747
Ser Leu Thr Asp Leu Val Glu His Phe Lys Lys Thr Gly Ile Glu Glu
             190                 195                 200

GCC TCA GGC GCC TTT GTC TAC CTG CGG CAG CCG TAC TAT GCC ACG AGG      795
Ala Ser Gly Ala Phe Val Tyr Leu Arg Gln Pro Tyr Tyr Ala Thr Arg
         205                 210                 215

GTG AAT GCG GCT GAC ATT GAG AAC CGA GTG TTG GAA CTG AAC AAG AAG      843
Val Asn Ala Ala Asp Ile Glu Asn Arg Val Leu Glu Leu Asn Lys Lys
     220                 225                 230
```

FIGURE 2 (1 of 3)

| | | | | | | | | | | | | | | | |
|---|---|---|---|---|---|---|---|---|---|---|---|---|---|---|---|
| CAG | GAG | TCC | GAG | GAT | ACA | GCC | AAG | GCT | GGC | TTC | TGG | GAG | GAG | TTT | GAG |
| Gln | Glu | Ser | Glu | Asp | Thr | Ala | Lys | Ala | Gly | Phe | Trp | Glu | Glu | Phe | Glu |
| | | 235 | | | 240 | | | | | 245 | | | | | |

```
CAG GAG TCC GAG GAT ACA GCC AAG GCT GGC TTC TGG GAG GAG TTT GAG          891
Gln Glu Ser Glu Asp Thr Ala Lys Ala Gly Phe Trp Glu Glu Phe Glu
        235             240                 245

AGT TTG CAG AAG CAG GAG GTG AAG AAC TTG CAC CAG CGT CTG GAA GGG          939
Ser Leu Gln Lys Gln Glu Val Lys Asn Leu His Gln Arg Leu Glu Gly
250             255                 260                 265

CAA CGG CCA GAG AAC AAG GGC AAG AAC CGC TAC AAG AAC ATT CTC CCC          987
Gln Arg Pro Glu Asn Lys Gly Lys Asn Arg Tyr Lys Asn Ile Leu Pro
                270                 275                 280

TTT GAC CAC AGC CGA GTG ATC CTG CAG GGA CGG GAC AGT AAC ATC CCC         1035
Phe Asp His Ser Arg Val Ile Leu Gln Gly Arg Asp Ser Asn Ile Pro
            285                 290                 295

GGG TCC GAC TAC ATC AAT GCC AAC TAC ATC AAG AAC CAG CTG CTA GGC         1083
Gly Ser Asp Tyr Ile Asn Ala Asn Tyr Ile Lys Asn Gln Leu Leu Gly
        300                 305                 310

CCT GAT GAG AAC GCT AAG ACC TAC ATC GCC AGC CAG GGC TGT CTG GAG         1131
Pro Asp Glu Asn Ala Lys Thr Tyr Ile Ala Ser Gln Gly Cys Leu Glu
    315                 320                 325

GCC ACA GTC AAT GAC TTC TGG CAG ATG GCG TGG CAG GAG AAC AGC CGT         1179
Ala Thr Val Asn Asp Phe Trp Gln Met Ala Trp Gln Glu Asn Ser Arg
330                 335                 340                 345

GTC ATC GTC ATG ACC ACC CGA GAG GTG GAG AAA GGC CGG AAC AAA TGC         1227
Val Ile Val Met Thr Thr Arg Glu Val Glu Lys Gly Arg Asn Lys Cys
                350                 355                 360

GTC CCA TAC TGG CCC GAG GTG GGC ATG CAG CGT GCT TAT GGG CCC TAC         1275
Val Pro Tyr Trp Pro Glu Val Gly Met Gln Arg Ala Tyr Gly Pro Tyr
            365                 370                 375

TCT GTG ACC AAC GTC GGG GAG CAT GAC ACA ACC GAA TAC AAA CTC CGT         1323
Ser Val Thr Asn Val Gly Glu His Asp Thr Thr Glu Tyr Lys Leu Arg
        380                 385                 390

ACC TTA CAG GTC TCC CCG CTG GAC AAT GGA GAC CTG ATT CGG GAG ATC         1371
Thr Leu Gln Val Ser Pro Leu Asp Asn Gly Asp Leu Ile Arg Glu Ile
    395                 400                 405

TGG CAT TAC CAG TAC CTG AGC TGG CCC GAC CAT GGG GTC CCC AGT GAG         1419
Trp His Tyr Gln Tyr Leu Ser Trp Pro Asp His Gly Val Pro Ser Glu
410                 415                 420                 425

CCT GGG GGT GTC CTC AGC TTC CTG GAC CAG ATC AAC CAG CGG CAG GAA         1467
Pro Gly Gly Val Leu Ser Phe Leu Asp Gln Ile Asn Gln Arg Gln Glu
                430                 435                 440

AGT CTG CCT CAC GCA GGG CCC ATC ATC GTG CAC TGC AGC GCC GGC ATC         1515
Ser Leu Pro His Ala Gly Pro Ile Ile Val His Cys Ser Ala Gly Ile
            445                 450                 455

GGC CGC ACA GGC ACC ATC ATT GTC ATC GAC ATG CTC ATG GAG AAC ATC         1563
Gly Arg Thr Gly Thr Ile Ile Val Ile Asp Met Leu Met Glu Asn Ile
        460                 465                 470

TCC ACC AAG GGC CTG GAC TGT GAC ATT GAC ATC CAG AAG ACC ATC CAG         1611
Ser Thr Lys Gly Leu Asp Cys Asp Ile Asp Ile Gln Lys Thr Ile Gln
    475                 480                 485
```

FIGURE 2 (2 of 3)

```
ATG GTG CGG GCG CAG CGC TCG GGC ATG GTG CAG ACG GAG GCG CAG TAC    1659
Met Val Arg Ala Gln Arg Ser Gly Met Val Gln Thr Glu Ala Gln Tyr
490             495                 500                 505

AAG TTC ATC TAC GTG GCC ATC GCC CAG TTC ATT GAA ACC ACT AAG AAG    1707
Lys Phe Ile Tyr Val Ala Ile Ala Gln Phe Ile Glu Thr Thr Lys Lys
            510                 515                 520

AAG CTG GAG GTC CTG CAG TCG CAG AAG GGC CAG GAG TCG GAG TAC GGG    1755
Lys Leu Glu Val Leu Gln Ser Gln Lys Gly Gln Glu Ser Glu Tyr Gly
                525                 530                 535

AAC ATC ACC TAT CCC CCA GCC ATG AAG AAT GCC CAT GCC AAG GCC TCC    1803
Asn Ile Thr Tyr Pro Pro Ala Met Lys Asn Ala His Ala Lys Ala Ser
            540                 545                 550

CGC ACC TCG TCC AAA CAC AAG GAG GAT GTG TAT GAG AAC CTG CAC ACT    1851
Arg Thr Ser Ser Lys His Lys Glu Asp Val Tyr Glu Asn Leu His Thr
        555                 560                 565

AAG AAC AAG AGG GAG GAG AAA GTG AAG AAG CAG CGG TCA GCA GAC AAG    1899
Lys Asn Lys Arg Glu Glu Lys Val Lys Lys Gln Arg Ser Ala Asp Lys
570                 575                 580                 585

GAG AAG AGC AAG GGT TCC CTC AAG AGG AAG TGAGCGGTGC TGTCCTCAGG      1949
Glu Lys Ser Lys Gly Ser Leu Lys Arg Lys ***
                590                 595

TGGCCATGCC TCAGCCCTGA CCCTGTGGAA GCATTTCGCG ATGGACAGAC TCACAACCTG  2009

AACCTAGGAG TGCCCCATTC TTTTGTAATT TAAATGGCTG CATCCCCCCC ACCTCTCCCT  2069

GACCCTGTAT ATAGCCCAGC CAGGCCCCAG GCAGGGCCAA CCCTTCTCCT CTTGTAAATA  2129

AAGCCCTGGG ATCACT                                                  2145
```

```
3B4-15 clone
(rat SH-PTP2)  KCVKYWPDECALKEYGVMRVRNVRESAAHDYTLREVKVCKVG QGNTERTVWQYHFRTWPD HGVPSDPGGVLDLVEEVHHKQESIVDA  GPVVHCSAG
               |||||||||||:|||||||||||||||||||||||||||||| |||||||||||||||||| |||||||||||:|||||||||||||||.  |||.|||||
hum SH-PTP2    KCVKYWPDEYALKEYGVMRVRNVKESAAHDYTLRELKLSKVG QGNTERTVWQYHFRTWPD HGVPSDPGGVLDFLEEVHHKQESIMDA. ..GPVVHCSAG
               |:.:||||:..:  :..:  .: .:.|:..:.  |||.:|.:                    ||||  ||||:.
      C8w      KCARYWPDEGRSEQFGHARIQCVSENSTSDYTLREFLVS    WRDQPARRIFHYHFQVWPD HGVPADPGCVLNFLQDVNTRQSHLAQAGEKPGPICVHCSAG
               |:.: |||| .|: |.:   ..: .|:. ..:|: :|| ::                     ||||:  ||: ::.: :    ||| :|.
   SH-PTP1     KCVPYWPEVGMQRAYGPYSVTNCGEHDTTEYKLRTLQVSPLD NGDLIREIWHYQYLSWPD HGVPSEPGGVLSFLDQINQRQESLPHA  GPIIVHCSAG hum RPTPμ      LCPQYWPENGVHR  HGPIQVEFVSADLEEDIISRIFRIYNAARPQDGYRMVQQFQFLGWPMYRDTPVSKRSFLKLIRQVDKWQEEYNGGE  GPTVHCLNG
hum HPTPβ      KCDHYWPADQDSLYYGDLILQMLSESVLPEWTIREFKICGEE QLDAHRLIRHFHYTVWPD HGVPETTQSLIQFVRTVRDYINRSPGA  GPTVHCSAG
hum LAR        KCHQYWPAKRSAR  YQYFVVDPMAEYNMPQYILREFKVT DA RDGQSRTIRQFQFTDWPE QGVPKTGEGFIDFIGQVHKTKEQFGQD  GPITVHCSAG
hum HPTPδ      KCHQYWPAKRSAR  YQYFVVDPMAEYNMPQYILREFKVT DA RDGQSRTVRQFQFTDWPE QGVPKSGEGFIDFIGQVHKTKEQFGQD  GPISVHCSAG
   DLAR        KCFQYWPHKRSVR  YQYYVVDPIAEYNMPQYKLREFKVT DA RDGSSRTVRQFQFIDWPE QGVPKSGEGFIDFIGQVHKTKEQFGQD  GPITVHCSAG
               ** *****                                                                                     ** *******
```

FIGURE 6A

```
CTGCCCCGCG TCCGGTCCCG AGCGGGCCTC CCTCGGGCCA GCCCGATGTG ACCGAGCCCA     60

GCGGAGCCTG AGCAAGGAGC GGGTCCGTCG CGGAGCCGGA GGGCGGGAGG AAC ATG       116
                                                             Met
                                                             1

ACA TCG CGG AGA TGG TTT CAC CCA AAT ATC ACT GGT GTG GAG GCA GAA     164
Thr Ser Arg Arg Trp Phe His Pro Asn Ile Thr Gly Val Glu Ala Glu
            5               10              15

AAC CTA CTG TTG ACA AGA GGA GTT GAT GGC AGT TTT TTG GCA AGG CCT     212
Asn Leu Leu Leu Thr Arg Gly Val Asp Gly Ser Phe Leu Ala Arg Pro
        20              25              30

AGT AAA AGT AAC CCT GGA GAC TTC ACA CTT TCC GTT AGA AGA AAT GGA     260
Ser Lys Ser Asn Pro Gly Asp Phe Thr Leu Ser Val Arg Arg Asn Gly
    35              40              45

GCT GTC ACC CAC ATC AAG ATT CAG AAC ACT GGT GAT TAC TAT GAC CTG     308
Ala Val Thr His Ile Lys Ile Gln Asn Thr Gly Asp Tyr Tyr Asp Leu
50              55              60              65

TAT GGA GGG GAG AAA TTT GCC ACT TTG GCT GAG TTG GTC CAG TAT TAC     356
Tyr Gly Gly Glu Lys Phe Ala Thr Leu Ala Glu Leu Val Gln Tyr Tyr
            70              75              80

ATG GAA CAT CAC GGG CAA TTA AAA GAG AAG AAT GGA GAT GTC ATT GAG     404
Met Glu His His Gly Gln Leu Lys Glu Lys Asn Gly Asp Val Ile Glu
        85              90              95

CTT AAA TAT CCT CTG AAC TGT GCA GAT CCT ACC TCT GAA AGG TGG TTT     452
Leu Lys Tyr Pro Leu Asn Cys Ala Asp Pro Thr Ser Glu Arg Trp Phe
    100             105             110

CAT GGA CAT CTC TCT GGG AAA GAA GCA GAG AAA TTA TTA ACT GAA AAA     500
His Gly His Leu Ser Gly Lys Glu Ala Glu Lys Leu Leu Thr Glu Lys
115             120             125

GGA AAA CAT GGT AGT TTT CTT GTA CGA GAG AGC CAG AGC CAC CCT GGA     548
Gly Lys His Gly Ser Phe Leu Val Arg Glu Ser Gln Ser His Pro Gly
130             135             140             145

GAT TTT GTT CTT TCT GTG CGC ACT GGT GAT GAC AAA GGG GAG AGC AAT     596
Asp Phe Val Leu Ser Val Arg Thr Gly Asp Asp Lys Gly Glu Ser Asn
            150             155             160

GAC GGC AAG TCT AAA GTG ACC CAT GTT ATG ATT CGC TGT CAG GAA CTG     644
Asp Gly Lys Ser Lys Val Thr His Val Met Ile Arg Cys Gln Glu Leu
        165             170             175

AAA TAC GAC GTT GGT GGA GGA GAA CGG TTT GAT TCT TTG ACA GAT CTT     692
Lys Tyr Asp Val Gly Gly Gly Glu Arg Phe Asp Ser Leu Thr Asp Leu
    180             185             190

GTG GAA CAT TAT AAG AAG AAT CCT ATG GTG GAA ACA TTG GGT ACA GTA     740
Val Glu His Tyr Lys Lys Asn Pro Met Val Glu Thr Leu Gly Thr Val
195             200             205

CTA CAA CTC AAG CAG CCC CTT AAC ACG ACT CGT ATA AAT GCT GCT GAA     788
Leu Gln Leu Lys Gln Pro Leu Asn Thr Thr Arg Ile Asn Ala Ala Glu
210             215             220             225
```

FIGURE 6B (1 of 3)

```
ATA GAA AGC AGA GTT CGA GAA CTA AGC AAA TTA GCT GAG ACC ACA GAT        836
Ile Glu Ser Arg Val Arg Glu Leu Ser Lys Leu Ala Glu Thr Thr Asp
            230                 235                 240

AAA GTC AAA CAA GGC TTT TGG GAA GAA TTT GAG ACA CTA CAA CAA CAG        884
Lys Val Lys Gln Gly Phe Trp Glu Glu Phe Glu Thr Leu Gln Gln Gln
            245                 250                 255

GAG TGC AAA CTT CTC TAC AGC CGA AAA GAG GGT CAA AGG CAA GAA AAC        932
Glu Cys Lys Leu Leu Tyr Ser Arg Lys Glu Gly Gln Arg Gln Glu Asn
            260                 265                 270

AAA AAC AAA AAT AGA TAT AAA AAC ATC CTG CCC TTT GAT CAT ACC AGG        980
Lys Asn Lys Asn Arg Tyr Lys Asn Ile Leu Pro Phe Asp His Thr Arg
        275                 280                 285

GTT GTC CTA CAC GAT GGT GAT CCC AAT GAG CCT GTT TCA GAT TAC ATC       1028
Val Val Leu His Asp Gly Asp Pro Asn Glu Pro Val Ser Asp Tyr Ile
290                 295                 300                 305

AAT GCA AAT ATC ATC ATG CCT GAA TTT GAA ACC AAG TGC AAC AAT TCA       1076
Asn Ala Asn Ile Ile Met Pro Glu Phe Glu Thr Lys Cys Asn Asn Ser
            310                 315                 320

AAG CCC AAA AAG AGT TAC ATT GCC ACA CAA GGC TGC CTG CAA AAC ACG       1124
Lys Pro Lys Lys Ser Tyr Ile Ala Thr Gln Gly Cys Leu Gln Asn Thr
            325                 330                 335

GTG AAT GAC TTT TGG CGG ATG GTG TTC CAA GAA AAC TCC CGA GTG ATT       1172
Val Asn Asp Phe Trp Arg Met Val Phe Gln Glu Asn Ser Arg Val Ile
            340                 345                 350

GTC ATG ACA ACG AAA GAA GTG GAG AGA GGA AAG AGT AAA TGT GTC AAA       1220
Val Met Thr Thr Lys Glu Val Glu Arg Gly Lys Ser Lys Cys Val Lys
        355                 360                 365

TAC TGG CCT GAT GAG TAT GCT CTA AAA GAA TAT GGC GTC ATG CGT GTT       1268
Tyr Trp Pro Asp Glu Tyr Ala Leu Lys Glu Tyr Gly Val Met Arg Val
370                 375                 380                 385

AGG AAC GTC AAA GAA AGC GCC GCT CAT GAC TAT ACG CTA AGA GAA CTT       1316
Arg Asn Val Lys Glu Ser Ala Ala His Asp Tyr Thr Leu Arg Glu Leu
            390                 395                 400

AAA CTT TCA AAG GTT GGA CAA GGG AAT ACG GAG AGA ACG GTC TGG CAA       1364
Lys Leu Ser Lys Val Gly Gln Gly Asn Thr Glu Arg Thr Val Trp Gln
            405                 410                 415

TAC CAC TTT CGG ACC TGG CCG GAC CAC GGC GTG CCC AGC GAC CCT GGG       1412
Tyr His Phe Arg Thr Trp Pro Asp His Gly Val Pro Ser Asp Pro Gly
            420                 425                 430

GGC GTG CTG GAC TTC CTG GAG GAG GTG CAC CAT AAG CAG GAG AGC ATC       1460
Gly Val Leu Asp Phe Leu Glu Glu Val His His Lys Gln Glu Ser Ile
        435                 440                 445
```

FIGURE 6B (2 of 3)

```
ATG GAT GCA GGG CCG GTC GTG GTG CAC TGC AGT GCT GGA ATT GGC CGG        1508
Met Asp Ala Gly Pro Val Val Val His Cys Ser Ala Gly Ile Gly Arg
450                 455                 460                 465

ACA GGG ACG TTC ATT GTG ATT GAT ATT CTT ATT GAC ATC ATC AGA GAG        1556
Thr Gly Thr Phe Ile Val Ile Asp Ile Leu Ile Asp Ile Ile Arg Glu
                    470                 475                 480

AAA GGT GTT GAC TGC GAT ATT GAC GTT CCC AAA ACC ATC CAG ATG GTG        1604
Lys Gly Val Asp Cys Asp Ile Asp Val Pro Lys Thr Ile Gln Met Val
                485                 490                 495

CGG TCT CAG AGG TCA GGG ATG GTC CAG ACA GAA GCA CAG TAC CGA TTT        1652
Arg Ser Gln Arg Ser Gly Met Val Gln Thr Glu Ala Gln Tyr Arg Phe
            500                 505                 510

ATC TAT ATG GCG GTC CAG CAT TAT ATT GAA ACA CTA CAG CGC AGG ATT        1700
Ile Tyr Met Ala Val Gln His Tyr Ile Glu Thr Leu Gln Arg Arg Ile
        515                 520                 525

GAA GAA GAG CAG AAA AGC AAG AGG AAA GGG CAC GAA TAT ACA AAT ATT        1748
Glu Glu Glu Gln Lys Ser Lys Arg Lys Gly His Glu Tyr Thr Asn Ile
530                 535                 540                 545

AAG TAT TCT CTA GCG GAC CAG ACG AGT GGA GAT CAG AGC CCT CTC CCG        1796
Lys Tyr Ser Leu Ala Asp Gln Thr Ser Gly Asp Gln Ser Pro Leu Pro
                    550                 555                 560

CCT TGT ACT CCA ACG CCA CCC TGT GCA GAA ATG AGA GAA GAC AGT GCT        1844
Pro Cys Thr Pro Thr Pro Pro Cys Ala Glu Met Arg Glu Asp Ser Ala
                565                 570                 575

AGA GTC TAT GAA AAC GTG GGC CTG ATG CAA CAG CAG AAA AGT TTC AGA T      1893
Arg Val Tyr Glu Asn Val Gly Leu Met Gln Gln Gln Lys Ser Phe Arg *
            580                 585                 590

GAGAAAACCT GCCAAAACTT CAGCACAGAA ATAGATGTGG ACTTTCACCC TCTCCCTAAA      1953

AAGATCAAGA ACAGACGCAA GAAAGTTTAT GTGAAGACAG AATTTGGATT TGGAAGGCTT      2013

GCAATGTGGT TGACTACCTT TTGATAAGCA AAATTTGAAA CCATTTAAAG ACCACTGTAT      2073

TTTAACTCAA CAATACCTGC TTCCCAATTA CTCATTTCCT CAGATAAGAA GAAATCATCT      2133

CTACAATGTA GACAACATTA TATTTTATAG AATTTGTTTG AAATTGAGGA AGCAGTTAAA      2193

TTGTGCGCTG TATTTTGCAG ATTATGGGGA TTCAAATTCT AGTAATAGGC TTTTTTATTT      2253

TTATTTTTAT ACCCTTAACC AGG                                              2276
```

FIGURE 6B (3 of 3)

```
SH-PTP2-N     WFHPNITGVEAENLLL TRGV  DGSFLARPSKSNPGDFTLSVRRNGA
CSW-N         WFHPTISGIEAEK    LLQEQGF DGSFLARLSSSNPGAFTLSVRRGNE
SH-PTP1-N     WFHRDLSGLDART    LLKGRGV HGSFLARPSRKNQGDFSLSVRVGDQ

SH-PTP2-C     WFHGHLSGKEAEK    LLTEKGK HGSFLVRESQSHPGDFVLSVRTGDPKGESNDGKS
CSW-C         WFHGNLSGKEAEKLIL ERGK   NGSFLVRESQSKPGDFVLSVRTDD
SH-PTP1-C     WYHGHMSGGQAET    LLQAKGE PWTFLVRESLSQPGDFVLSVLSDQPKAGP     GSPL consensus     W H   G   AR     L   G   FL RS    G F LSV
                                +                        + hum fer       WYHGAIPRIEAQE    LLKKQ        GDFLVRESHGKPGEYVLSVYSDGQR
bov GAP       WFHGKISKQEAYN    LLMTVGQ ACSFLVRPSDNTPGDYSLYFRTSEN
mouse fgr-N   WYFGKKSRKDAERQLLSS GNPQGAFLIRESETTKGAYSLSIRDWDQNRGD
hum Nck-N     WYYGKVTRHQAEMALN ERGH   EGDFLIRDSESSPNDFSVSLKAQG
hydra stk     WYFGDVKRAKAEKRLM VRGLPSGTFLIRKAETAVGNFSLSVRD              GD mouse fgr-C   WYFGKISRKDAERQLLSS GNPQGAFLIRESETTKGAYSLSIRDWDQNRGD
chick yes     WYFGKMGRKDAER    LLLNPGNQRGIFLVRESETTKGAYSLSIRDWDEVRGD
hum fyn       WYFGKLGRKDAERQLLSF GNPRGTFLIRESETTKGAYSLSIRDWDDMKGD
mouse lsk     WFFKNLSRKDAERQLLAP GNTHGSFLIRESESTAGSFSLSVRDFDQNQGE
mouse blk     WFFRTISRKDAERQLLAP MNKAGSFLIRESESNKGAFSLSVKDIT TQGE
hum Nck-C     WYYGKVTRHQAEMALN ERGH   EGDFLIRDSESSPNDFSVSLKAQG
                                •                        •
              |_____|      |_____|
                      I                          II
```

FIGURE 7 (1 of 2)

```
SH-PTP2-N  (cont'd)  VTHIKIQNTGD  YDLYGGEKFATLAELVQYYMEHHGQLKEKNGDVIELKYPLNCA
Csw-N      (cont'd)  VTHIKIQNNGD  FFDLYGGEKFATLPELVQYYME NGELKEKNGQAIELKQPLICA
SH-PTP1-N  (cont'd)  VTHIRIQNSGD  FYDLYGGEKFATLTELVEYYTQQGVVQDRDGTIIHLKYPLNCS SH-PTP2-C  (cont'd)  KVTHVMIRCQEL KYDVGGGERFDSLTDLVEHYK  KNRMVETLGTVLQLK
Csw-C      (cont'd)  KVTHVMIRWQDK KYDVGGGESFGTLSELIDHYK  RNPMVETCGTVVHLR
SH-PTP1-C  (cont'd)  RVTHIKVMCEGG RYTVGGLETFDSLTDLVEHFK  KTGIEEASGAFVYL consensus  (cont'd)  VTH              G  E F   L  L             G    L  PL  C
                     + hum fer    (cont'd)  RHFIIQYVDN MYRFEGTG FSNIPQLIDHHYTTKQVITKKSGVVLLNPIPKDKK
bov GAP    (cont'd)  IQRFKICPTPN NQFMMGGRYYNSIGDIIDHYRKEQIVEGYYLKEPVPMQDQEQVL
mouse fgr-N (cont'd) HIKHYKIRKLDTGGYYITTRAQFDSIQDLVQHYMEVNDGLCYLLTAPCTTTKPQTLG
hum Nck-N  (cont'd)  KNKHFKVQLKET VYCI GQRKFSTMEELVEHYKKAPIFTSEQGEKLYLVKHLS
hydra stk  (cont'd)  SVKHYRVRKLDTGGYFITTRAPFNSLYELVQHYTKDADGLVCALTLPCPKDKPVTGG mouse fgr-C (cont'd) HIKHYKIRKLDTGGYYITTRAQFDSIQDLVQHYMEVNDGLCYLLTAPCT
chick yes  (cont'd)  NVKHYKIRKLDNGGYYITTRAQFESLQKLVKHYREHADGLCHKLTTVCP
hum fyn    (cont'd)  HVKHYKIRKLDNGGYYITTRAQFETLQQLVQHYSERAAGLCCRLVVPCH
mouse lsk  (cont'd)  VVKHYKIRNLDNGGYYISPRITFPGLHDLVRHYTNASDGLCTKLSRPCQ
mouse blk  (cont'd)  VVKHYKIRSLDNGGYYISPRITFPTLQALVQHYSKKGDGLCQKLTLPCV
hum Nck-C  (cont'd)  KNKHFKVQLKET VYCI GQRKFSTMEKLVEHYKKAPIFTSEQGEKLYL ─────        ─────          ─────
                      III           IV              V
```

FIGURE 7 (2 of 2)

200A:      TCC ACG GTA GCT TCC TGG CTC
200B       AGT GGG ATC GGA GCA GTT CAG

400A:      CCA TCA TCC ACC TCA AGT ACC CG
400B:      CCA CCC TCG CAC ATG ACC TTG

600A:      CCG CTC AGG GTC ACC CAC ATC
600B:      CTG TAT CCT CGG ACT CCT GC

800A:      CGA GTG TTG GAA CTG AAC AAG
800B:      GAT GTA GTT GGC ATT GAT GTA G

1000A:     GAC GGG ACA GTA ACA TCC CCG
1000B:     CCA TAA GCA CGC TGC ATG CC

1200A:     GAA CAA ATG CGT CCC ATA CTG
1200B:     CTG CCG CTG GTT GAT CTG GTC

1400A:     GGG TGT CCT CAG CCT CCT G
1400B:     CTT GTA CTG CGC CTC CGT CTG

FIGURE 9

SEQUENCE LISTING ( 1 ) GENERAL INFORMATION:

( i i i ) NUMBER OF SEQUENCES: 54

( 2 ) INFORMATION FOR SEQ ID NO:1:

( i ) SEQUENCE CHARACTERISTICS:
        ( A ) LENGTH: 1747 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 2..1540

( x i ) SEQUENCE DESCRIPTION: SEQ ID NO:1:

```
A  ATT  CCG  ATC  CTG  CAG  GAC  CGA  GAC  GGC  ACC  ATC  ATC  CAC  CTC  AAG              46
   Ile  Pro  Ile  Leu  Gln  Asp  Arg  Asp  Gly  Thr  Ile  Ile  His  Leu  Lys
   1              5                        10                       15

TAC  CCA  CTG  AAC  TGC  TCG  GAC  CCC  ACC  AGC  GAG  AGG  TGG  TAT  CAT  GGT            94
Tyr  Pro  Leu  Asn  Cys  Ser  Asp  Pro  Thr  Ser  Glu  Arg  Trp  Tyr  His  Gly
                    20                       25                       30

CAC  ATG  TCT  GGA  GGG  CAG  GCA  GAG  TCA  CTG  CTG  CAG  GCC  AAG  GGC  GAG           142
His  Met  Ser  Gly  Gly  Gln  Ala  Glu  Ser  Leu  Leu  Gln  Ala  Lys  Gly  Glu
                    35                       40                       45

CCC  TGG  ACA  TTT  CTT  GTG  CGT  GAG  AGT  CTC  AGC  CAA  CCT  GGT  GAT  TTT           190
Pro  Trp  Thr  Phe  Leu  Val  Arg  Glu  Ser  Leu  Ser  Gln  Pro  Gly  Asp  Phe
               50                       55                       60

GTG  CTC  TCT  GTG  CTC  AAT  GAC  CAG  CCC  AAG  GCT  GGC  CCG  GGT  TCC  CCG           238
Val  Leu  Ser  Val  Leu  Asn  Asp  Gln  Pro  Lys  Ala  Gly  Pro  Gly  Ser  Pro
```

-continued

| | | | | 65 | | | | 70 | | | | 75 | | | |
|---|---|---|---|---|---|---|---|---|---|---|---|---|---|---|---|

| CTC | AGG | GTC | ACG | CAC | ATC | AAG | GTT | ATG | TGT | GAG | GGT | GGA | CGA | TAC | ACT | 286 |
| Leu | Arg | Val | Thr | His | Ile | Lys | Val | Met | Cys | Glu | Gly | Gly | Arg | Tyr | Thr | |
| 80 | | | | | 85 | | | | | 90 | | | | | 95 | |

| GTG | GGT | GGC | TCA | GAG | ACA | TTC | GAT | AGC | CTC | ACA | GAC | CTG | GTG | GAG | CAC | 334 |
| Val | Gly | Gly | Ser | Glu | Thr | Phe | Asp | Ser | Leu | Thr | Asp | Leu | Val | Glu | His | |
| | | | | 100 | | | | | 105 | | | | | 110 | | |

| TTC | AAG | AAG | ACG | GGG | ATT | GAG | GAG | GCC | TCA | GGT | GCC | TTT | GTC | TAC | CTG | 382 |
| Phe | Lys | Lys | Thr | Gly | Ile | Glu | Glu | Ala | Ser | Gly | Ala | Phe | Val | Tyr | Leu | |
| | | | 115 | | | | | 120 | | | | | 125 | | | |

| AGG | CAG | CCT | TAC | TAT | GCC | ACT | CGG | GTA | AAT | GCA | GCA | GAC | ATT | GAG | AAC | 430 |
| Arg | Gln | Pro | Tyr | Tyr | Ala | Thr | Arg | Val | Asn | Ala | Ala | Asp | Ile | Glu | Asn | |
| | | 130 | | | | | 135 | | | | | 140 | | | | |

| CGG | GTC | TTG | GAA | CTG | AAC | AAG | AAG | CAG | GAG | TCA | GAG | GAC | ACA | GCC | AAG | 478 |
| Arg | Val | Leu | Glu | Leu | Asn | Lys | Lys | Gln | Glu | Ser | Glu | Asp | Thr | Ala | Lys | |
| | 145 | | | | | 150 | | | | | 155 | | | | | |

| GCC | GGC | TTC | TGG | GAG | GAG | TTT | GAG | AGT | CTG | CAA | AAG | CAA | GAG | GTA | AAG | 526 |
| Ala | Gly | Phe | Trp | Glu | Glu | Phe | Glu | Ser | Leu | Gln | Lys | Gln | Glu | Val | Lys | |
| 160 | | | | | 165 | | | | | 170 | | | | | 175 | |

| AAC | TTG | CAC | CAG | CGT | CTG | GAA | GGG | CAG | CGG | CCG | GAG | AAC | AAG | AGC | AAG | 574 |
| Asn | Leu | His | Gln | Arg | Leu | Glu | Gly | Gln | Arg | Pro | Glu | Asn | Lys | Ser | Lys | |
| | | | | 180 | | | | | 185 | | | | | 190 | | |

| AAC | CGC | TAC | AAG | AAC | ATT | CTT | CCC | TTT | GAC | CAC | AGC | CGA | GTG | ATC | CTG | 622 |
| Asn | Arg | Tyr | Lys | Asn | Ile | Leu | Pro | Phe | Asp | His | Ser | Arg | Val | Ile | Leu | |
| | | | 195 | | | | | 200 | | | | | 205 | | | |

| CAG | GGA | CGT | GAC | AGT | AAC | ATC | CCA | GGG | TCT | GAT | TAC | ATC | AAT | GCC | AAC | 670 |
| Gln | Gly | Arg | Asp | Ser | Asn | Ile | Pro | Gly | Ser | Asp | Tyr | Ile | Asn | Ala | Asn | |
| | | 210 | | | | | 215 | | | | | 220 | | | | |

| TAC | GTT | AAG | AAC | CAG | CTG | CTA | GGT | CCG | GAT | GAG | AAC | TCT | AAG | ACC | TAC | 718 |
| Tyr | Val | Lys | Asn | Gln | Leu | Leu | Gly | Pro | Asp | Glu | Asn | Ser | Lys | Thr | Tyr | |
| | 225 | | | | | 230 | | | | | 235 | | | | | |

| ATC | GCC | AGT | CAG | GGC | TGT | CTG | GAC | GCT | ACC | GTC | AAT | GAC | TTC | TGG | CAG | 766 |
| Ile | Ala | Ser | Gln | Gly | Cys | Leu | Asp | Ala | Thr | Val | Asn | Asp | Phe | Trp | Gln | |
| 240 | | | | | 245 | | | | | 250 | | | | | 255 | |

| ATG | GCT | CGG | CAG | GAG | AAC | ACT | CGT | GTC | ATC | GTC | ATG | ACT | ACC | AGA | GAG | 814 |
| Met | Ala | Arg | Gln | Glu | Asn | Thr | Arg | Val | Ile | Val | Met | Thr | Thr | Arg | Glu | |
| | | | | 260 | | | | | 265 | | | | | 270 | | |

| GTG | GAG | AAA | GGC | CGG | AAC | AAA | TGT | GTC | CCA | TAC | TGG | CCT | GAG | GTG | GGC | 862 |
| Val | Glu | Lys | Gly | Arg | Asn | Lys | Cys | Val | Pro | Tyr | Trp | Pro | Glu | Val | Gly | |
| | | | 275 | | | | | 280 | | | | | 285 | | | |

| ACT | CAG | CGC | GTC | TAT | GGG | CTC | TAC | TCT | GTG | ACC | AAC | TGT | AAA | GAG | CAT | 910 |
| Thr | Gln | Arg | Val | Tyr | Gly | Leu | Tyr | Ser | Val | Thr | Asn | Cys | Lys | Glu | His | |
| | | 290 | | | | | 295 | | | | | 300 | | | | |

| GAC | ACA | GCA | GAG | TAC | AAA | CTT | CGA | ACA | TTG | CAG | ATC | TCC | CCA | CTG | GAC | 958 |
| Asp | Thr | Ala | Glu | Tyr | Lys | Leu | Arg | Thr | Leu | Gln | Ile | Ser | Pro | Leu | Asp | |
| | 305 | | | | | 310 | | | | | 315 | | | | | |

| AAT | GGG | GAC | CTG | GTT | CGG | GAG | ATA | TGG | CAC | TAC | CAG | TAC | CTG | AGC | TGG | 1006 |
| Asn | Gly | Asp | Leu | Val | Arg | Glu | Ile | Trp | His | Tyr | Gln | Tyr | Leu | Ser | Trp | |
| 320 | | | | | 325 | | | | | 330 | | | | | 335 | |

| CCT | GAC | CAT | GGG | GTT | CCC | AGT | GAG | CCT | GGG | GGT | GTC | CTC | GGC | TTC | CTG | 1054 |
| Pro | Asp | His | Gly | Val | Pro | Ser | Glu | Pro | Gly | Gly | Val | Leu | Gly | Phe | Leu | |
| | | | | 340 | | | | | 345 | | | | | 350 | | |

| GAT | CAG | ATC | AAC | CAG | CGG | CAG | GAA | AGT | TTG | CCT | CAC | GCG | GGG | CCC | ATC | 1102 |
| Asp | Gln | Ile | Asn | Gln | Arg | Gln | Glu | Ser | Leu | Pro | His | Ala | Gly | Pro | Ile | |
| | | | 355 | | | | | 360 | | | | | 365 | | | |

| ATT | GTG | CAT | TGC | AGC | GCT | GGC | ATC | GGC | CGC | ACG | GGC | ACC | ATC | ATC | GTC | 1150 |
| Ile | Val | His | Cys | Ser | Ala | Gly | Ile | Gly | Arg | Thr | Gly | Thr | Ile | Ile | Val | |
| | | 370 | | | | | 375 | | | | | 380 | | | | |

| ATT | GAT | ATG | CTC | ATG | GAG | AGC | GTT | TCC | ACC | AAG | GGG | CTA | GAC | TGT | GAC | 1198 |
| Ile | Asp | Met | Leu | Met | Glu | Ser | Val | Ser | Thr | Lys | Gly | Leu | Asp | Cys | Asp | |

|   |   |   |   |   |   |   |   |   |   |   |   |   |   |   |   |   |
|---|---|---|---|---|---|---|---|---|---|---|---|---|---|---|---|---|
|   |   | 385 |   |   |   |   | 390 |   |   |   |   | 395 |   |   |   |   |
| ATT | GAC | ATC | CAG | AAG | ACC | ATC | CAG | ATG | GTA | CGG | GCA | CAG | CGC | TCT | GGC | 1246 |
| Ile | Asp | Ile | Gln | Lys | Thr | Ile | Gln | Met | Val | Arg | Ala | Gln | Arg | Ser | Gly |   |
| 400 |   |   |   |   | 405 |   |   |   |   | 410 |   |   |   |   | 415 |   |
| ATG | GTG | CAG | ACA | GAG | GCA | CAG | TAC | AAG | TTT | ATT | TAT | GTG | GCC | ATC | GCC | 1294 |
| Met | Val | Gln | Thr | Glu | Ala | Gln | Tyr | Lys | Phe | Ile | Tyr | Val | Ala | Ile | Ala |   |
|   |   |   |   | 420 |   |   |   |   | 425 |   |   |   |   | 430 |   |   |
| CAG | TTC | ATC | GAA | ACA | ACC | AAG | AAG | AAA | CTG | GAG | ATC | ATA | CAA | TCC | CAG | 1342 |
| Gln | Phe | Ile | Glu | Thr | Thr | Lys | Lys | Lys | Leu | Glu | Ile | Ile | Gln | Ser | Gln |   |
|   |   |   |   | 435 |   |   |   |   | 440 |   |   |   |   | 445 |   |   |
| AGG | GGC | CAG | GAG | TCG | GAG | TAT | GGG | AAC | ATC | ACC | TAC | CCT | CCG | GCT | TTG | 1390 |
| Arg | Gly | Gln | Glu | Ser | Glu | Tyr | Gly | Asn | Ile | Thr | Tyr | Pro | Pro | Ala | Leu |   |
|   |   | 450 |   |   |   |   | 455 |   |   |   |   | 460 |   |   |   |   |
| AGG | AGT | GCC | CAC | GCC | AAA | GCC | TCC | CGT | ACC | TCC | TCC | AAA | CAC | AAG | GAG | 1438 |
| Arg | Ser | Ala | His | Ala | Lys | Ala | Ser | Arg | Thr | Ser | Ser | Lys | His | Lys | Glu |   |
|   | 465 |   |   |   |   | 470 |   |   |   |   | 475 |   |   |   |   |   |
| GAG | GTG | TAC | GAA | AAC | GTG | CAT | AGC | AAG | AAC | AAG | AAA | GAA | GAG | AAA | GTA | 1486 |
| Glu | Val | Tyr | Glu | Asn | Val | His | Ser | Lys | Asn | Lys | Lys | Glu | Glu | Lys | Val |   |
| 480 |   |   |   |   | 485 |   |   |   |   | 490 |   |   |   |   | 495 |   |
| AAG | AAG | CAG | CGA | TCG | GCA | GAC | AAG | GAG | AAG | AAC | AAA | GGT | TCT | CTC | AAG | 1534 |
| Lys | Lys | Gln | Arg | Ser | Ala | Asp | Lys | Glu | Lys | Asn | Lys | Gly | Ser | Leu | Lys |   |
|   |   |   |   | 500 |   |   |   |   | 505 |   |   |   |   | 510 |   |   |

```
AGG AAG TGAGCTGGCA TCAGCCTTAC TCCGTGCAGA GGCCTCCGCT GGGCAGACAG      1590
Arg Lys
AGACCTGTAG TCCACACCAC CCCCATCTTG TTGTAATTTA AGTGACCGTG GTCCTCTGAA   1650

CCTGTATATG GCTCAGCAAG CCTCAGGGAG AGTCAGACCC TTCTCTTCTT GTAAATAAAG   1710

CCCCTGGACA ACTGTGAAAA AAAAAAAAA AAAAAA                              1747
```

( 2 ) INFORMATION FOR SEQ ID NO:2:

( i ) SEQUENCE CHARACTERISTICS:
        ( A ) LENGTH: 513 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

|   |   |   |   |   |   |   |   |   |   |   |   |   |   |   |
|---|---|---|---|---|---|---|---|---|---|---|---|---|---|---|
| Ile | Pro | Ile | Leu | Gln | Asp | Arg | Asp | Gly | Thr | Ile | Ile | His | Leu | Lys | Tyr |
| 1 |   |   |   | 5 |   |   |   |   | 10 |   |   |   |   | 15 |   |
| Pro | Leu | Asn | Cys | Ser | Asp | Pro | Thr | Ser | Glu | Arg | Trp | Tyr | His | Gly | His |
|   |   |   | 20 |   |   |   |   | 25 |   |   |   |   | 30 |   |   |
| Met | Ser | Gly | Gly | Gln | Ala | Glu | Ser | Leu | Leu | Gln | Ala | Lys | Gly | Glu | Pro |
|   |   | 35 |   |   |   |   | 40 |   |   |   |   | 45 |   |   |   |
| Trp | Thr | Phe | Leu | Val | Arg | Glu | Ser | Leu | Ser | Gln | Pro | Gly | Asp | Phe | Val |
|   | 50 |   |   |   |   | 55 |   |   |   |   | 60 |   |   |   |   |
| Leu | Ser | Val | Leu | Asn | Asp | Gln | Pro | Lys | Ala | Gly | Pro | Gly | Ser | Pro | Leu |
| 65 |   |   |   |   | 70 |   |   |   |   | 75 |   |   |   |   | 80 |
| Arg | Val | Thr | His | Ile | Lys | Val | Met | Cys | Glu | Gly | Gly | Arg | Tyr | Thr | Val |
|   |   |   |   | 85 |   |   |   |   | 90 |   |   |   |   | 95 |   |
| Gly | Gly | Ser | Glu | Thr | Phe | Asp | Ser | Leu | Thr | Asp | Leu | Val | Glu | His | Phe |
|   |   |   | 100 |   |   |   |   | 105 |   |   |   |   | 110 |   |   |
| Lys | Lys | Thr | Gly | Ile | Glu | Glu | Ala | Ser | Gly | Ala | Phe | Val | Tyr | Leu | Arg |
|   |   | 115 |   |   |   |   | 120 |   |   |   |   | 125 |   |   |   |
| Gln | Pro | Tyr | Tyr | Ala | Thr | Arg | Val | Asn | Ala | Ala | Asp | Ile | Glu | Asn | Arg |
|   | 130 |   |   |   |   | 135 |   |   |   |   | 140 |   |   |   |   |
| Val | Leu | Glu | Leu | Asn | Lys | Lys | Gln | Glu | Ser | Glu | Asp | Thr | Ala | Lys | Ala |
| 145 |   |   |   |   | 150 |   |   |   |   | 155 |   |   |   |   | 160 |

```
Gly Phe Trp Glu Glu Phe Glu Ser Leu Gln Lys Gln Glu Val Lys Asn
            165                 170                 175

Leu His Gln Arg Leu Glu Gly Gln Arg Pro Glu Asn Lys Ser Lys Asn
            180                 185                 190

Arg Tyr Lys Asn Ile Leu Pro Phe Asp His Ser Arg Val Ile Leu Gln
            195                 200                 205

Gly Arg Asp Ser Asn Ile Pro Gly Ser Asp Tyr Ile Asn Ala Asn Tyr
            210                 215                 220

Val Lys Asn Gln Leu Leu Gly Pro Asp Glu Asn Ser Lys Thr Tyr Ile
225                 230                 235                 240

Ala Ser Gln Gly Cys Leu Asp Ala Thr Val Asn Asp Phe Trp Gln Met
                245                 250                 255

Ala Arg Gln Glu Asn Thr Arg Val Ile Val Met Thr Thr Arg Glu Val
            260                 265                 270

Glu Lys Gly Arg Asn Lys Cys Val Pro Tyr Trp Pro Glu Val Gly Thr
            275                 280                 285

Gln Arg Val Tyr Gly Leu Tyr Ser Val Thr Asn Cys Lys Glu His Asp
    290                 295                 300

Thr Ala Glu Tyr Lys Leu Arg Thr Leu Gln Ile Ser Pro Leu Asp Asn
305                 310                 315                 320

Gly Asp Leu Val Arg Glu Ile Trp His Tyr Gln Tyr Leu Ser Trp Pro
                325                 330                 335

Asp His Gly Val Pro Ser Glu Pro Gly Gly Val Leu Gly Phe Leu Asp
            340                 345                 350

Gln Ile Asn Gln Arg Gln Glu Ser Leu Pro His Ala Gly Pro Ile Ile
            355                 360                 365

Val His Cys Ser Ala Gly Ile Gly Arg Thr Gly Thr Ile Ile Val Ile
    370                 375                 380

Asp Met Leu Met Glu Ser Val Ser Thr Lys Gly Leu Asp Cys Asp Ile
385                 390                 395                 400

Asp Ile Gln Lys Thr Ile Gln Met Val Arg Ala Gln Arg Ser Gly Met
                405                 410                 415

Val Gln Thr Glu Ala Gln Tyr Lys Phe Ile Tyr Val Ala Ile Ala Gln
            420                 425                 430

Phe Ile Glu Thr Thr Lys Lys Lys Leu Glu Ile Ile Gln Ser Gln Arg
            435                 440                 445

Gly Gln Glu Ser Glu Tyr Gly Asn Ile Thr Tyr Pro Pro Ala Leu Arg
    450                 455                 460

Ser Ala His Ala Lys Ala Ser Arg Thr Ser Ser Lys His Lys Glu Glu
465                 470                 475                 480

Val Tyr Glu Asn Val His Ser Lys Asn Lys Glu Glu Lys Val Lys
                485                 490                 495

Lys Gln Arg Ser Ala Asp Lys Glu Lys Asn Lys Gly Ser Leu Lys Arg
            500                 505                 510

Lys
```

( 2 ) INFORMATION FOR SEQ ID NO:3:

( i ) SEQUENCE CHARACTERISTICS:
        ( A ) LENGTH: 285 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:

(A) NAME/KEY: CDS
(B) LOCATION: 1..285

(xi) SEQUENCE DESCRIPTION: SEQ ID NO:3:

| AAA | TGC | GCG | GAA | TAT | TGG | CCT | TCC | AAG | CAG | GCT | CAG | GAC | TAC | GGG | GAC | 48 |
| Lys | Cys | Ala | Glu | Tyr | Trp | Pro | Ser | Lys | Gln | Ala | Gln | Asp | Tyr | Gly | Asp | |
| 1 | | | | 5 | | | | | 10 | | | | | 15 | | |

| ATA | ACT | GTG | GCA | ATG | ACA | TCA | GAA | GTT | GTT | CTT | CCG | GAA | TGG | ACC | ATC | 96 |
| Ile | Thr | Val | Ala | Met | Thr | Ser | Glu | Val | Val | Leu | Pro | Glu | Trp | Thr | Ile | |
| | | | 20 | | | | | 25 | | | | | 30 | | | |

| AGA | GAT | TTT | GTG | GTG | AAA | AAT | ATG | CAG | AGT | AGT | GAG | AGT | CAT | CCT | CTG | 144 |
| Arg | Asp | Phe | Val | Val | Lys | Asn | Met | Gln | Ser | Ser | Glu | Ser | His | Pro | Leu | |
| | | 35 | | | | | 40 | | | | | 45 | | | | |

| CGG | CAG | TTC | CAT | TTC | ACC | TCC | TGG | CCT | GAC | CAT | GGT | GTT | CCT | GAC | ACC | 192 |
| Arg | Gln | Phe | His | Phe | Thr | Ser | Trp | Pro | Asp | His | Gly | Val | Pro | Asp | Thr | |
| | 50 | | | | | 55 | | | | | 60 | | | | | |

| ACC | GAC | CTG | CTC | ATC | AAC | TTT | CGG | TAC | CTG | GTC | CGG | GAT | TAC | ATG | AAG | 240 |
| Thr | Asp | Leu | Leu | Ile | Asn | Phe | Arg | Tyr | Leu | Val | Arg | Asp | Tyr | Met | Lys | |
| 65 | | | | | 70 | | | | | 75 | | | | | 80 | |

| CAG | ATC | CCC | CCT | GAG | TCA | CCA | ATC | CTG | GTC | CAT | TGT | TCT | GCC | GGA | | 285 |
| Gln | Ile | Pro | Pro | Glu | Ser | Pro | Ile | Leu | Val | His | Cys | Ser | Ala | Gly | | |
| | | | | 85 | | | | | 90 | | | | | 95 | | |

(2) INFORMATION FOR SEQ ID NO:4:

(i) SEQUENCE CHARACTERISTICS:
(A) LENGTH: 95 amino acids
(B) TYPE: amino acid
(D) TOPOLOGY: linear (ii) MOLECULE TYPE: protein (xi) SEQUENCE DESCRIPTION: SEQ ID NO:4:

| Lys | Cys | Ala | Glu | Tyr | Trp | Pro | Ser | Lys | Gln | Ala | Gln | Asp | Tyr | Gly | Asp |
| 1 | | | | 5 | | | | | 10 | | | | | 15 | |

| Ile | Thr | Val | Ala | Met | Thr | Ser | Glu | Val | Val | Leu | Pro | Glu | Trp | Thr | Ile |
| | | | 20 | | | | | 25 | | | | | 30 | | |

| Arg | Asp | Phe | Val | Val | Lys | Asn | Met | Gln | Ser | Ser | Glu | Ser | His | Pro | Leu |
| | | 35 | | | | | 40 | | | | | 45 | | | |

| Arg | Gln | Phe | His | Phe | Thr | Ser | Trp | Pro | Asp | His | Gly | Val | Pro | Asp | Thr |
| | 50 | | | | | 55 | | | | | 60 | | | | |

| Thr | Asp | Leu | Leu | Ile | Asn | Phe | Arg | Tyr | Leu | Val | Arg | Asp | Tyr | Met | Lys |
| 65 | | | | | 70 | | | | | 75 | | | | | 80 |

| Gln | Ile | Pro | Pro | Glu | Ser | Pro | Ile | Leu | Val | His | Cys | Ser | Ala | Gly |
| | | | | 85 | | | | | 90 | | | | | 95 |

(2) INFORMATION FOR SEQ ID NO:5:

(i) SEQUENCE CHARACTERISTICS:
(A) LENGTH: 2145 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 145..1929

(xi) SEQUENCE DESCRIPTION: SEQ ID NO:5:

| CGGCAGAACT | GGGACCACCG | GGGGTGGTGA | GGCGGCCCGG | CACTGGGAGC | TGCATCTGAG | 60 |
| GCTTAGTCCC | TGAGCTCTCT | GCCTGCCCAG | ACTAGCTGCA | CCTCCTCATT | CCCTGCGCCC | 120 |

```
CCTTCCTCTC CGGAAGCCCC CAGG ATG GTG AGG TGG TTT CAC CGA GAC CTC         171
                          Met Val Arg Trp Phe His Arg Asp Leu
                          1               5

AGT GGG CTG GAT GCA GAG ACC CTG CTC AAG GGC CGA GGT GTC CAC GGT         219
Ser Gly Leu Asp Ala Glu Thr Leu Leu Lys Gly Arg Gly Val His Gly
 10               15                  20                  25

AGC TTC CTG GTC TGG CCC AGT CGC AAG AAC CAG GGT GAC TTC TCG CTC         267
Ser Phe Leu Val Trp Pro Ser Arg Lys Asn Gln Gly Asp Phe Ser Leu
                 30                  35                  40

TCC GTC AGG GTG GGG GAT CAG GTG ACC CAT ATT CGG ATC CAG AAC TCA         315
Ser Val Arg Val Gly Asp Gln Val Thr His Ile Arg Ile Gln Asn Ser
             45                  50                  55

GGG GAT TTC TAT GAC CTG TAT GGA GGG GAG AAG TTT GCG ACT CTG ACA         363
Gly Asp Phe Tyr Asp Leu Tyr Gly Gly Glu Lys Phe Ala Thr Leu Thr
         60                  65                  70

GAG CTG GTG GAG TAC TAC ACT CAG CAG CAG GGT GTG GTG CAG GAC CGC         411
Glu Leu Val Glu Tyr Tyr Thr Gln Gln Gln Gly Val Val Gln Asp Arg
     75                  80                  85

GAC GGC ACC ATC ATC CAC CTC AAG TAC CCG CTG AAC TGC TCC GAT CCC         459
Asp Gly Thr Ile Ile His Leu Lys Tyr Pro Leu Asn Cys Ser Asp Pro
 90                  95                 100                 105

ACT AGT GAG AGG TGG TAC CAT GGC CAC ATG TCT GGC GGG CAG GCA GAG         507
Thr Ser Glu Arg Trp Tyr His Gly His Met Ser Gly Gly Gln Ala Glu
                110                 115                 120

ACG CTG CTG CAG GCC AAG GGC GAG CCC TGG ACG TTT CTT GTG CGT GAG         555
Thr Leu Leu Gln Ala Lys Gly Glu Pro Trp Thr Phe Leu Val Arg Glu
            125                 130                 135

AGC CTC AGC CAG CCT GGA GAC TTC GTG CTT TCT GTG CTC AGT GAC CAG         603
Ser Leu Ser Gln Pro Gly Asp Phe Val Leu Ser Val Leu Ser Asp Gln
        140                 145                 150

CCC AAG GCT GGC CCA GGC TCC CCG CTC AGG GTC ACC CAC ATC AAG GTC         651
Pro Lys Ala Gly Pro Gly Ser Pro Leu Arg Val Thr His Ile Lys Val
    155                 160                 165

ATG TGC GAG GGT GGA CGC TAC ACA GTG GGT GGT TTG GAG ACC TTC GAC         699
Met Cys Glu Gly Gly Arg Tyr Thr Val Gly Gly Leu Glu Thr Phe Asp
170                 175                 180                 185

AGC CTC ACG GAC CTG GTG GAG CAT TTC AAG AAG ACG GGG ATT GAG GAG         747
Ser Leu Thr Asp Leu Val Glu His Phe Lys Lys Thr Gly Ile Glu Glu
                190                 195                 200

GCC TCA GGC GCC TTT GTC TAC CTG CGG CAG CCG TAC TAT GCC ACG AGG         795
Ala Ser Gly Ala Phe Val Tyr Leu Arg Gln Pro Tyr Tyr Ala Thr Arg
            205                 210                 215

GTG AAT GCG GCT GAC ATT GAG AAC CGA GTG TTG GAA CTG AAC AAG AAG         843
Val Asn Ala Ala Asp Ile Glu Asn Arg Val Leu Glu Leu Asn Lys Lys
        220                 225                 230

CAG GAG TCC GAG GAT ACA GCC AAG GCT GGC TTC TGG GAG GAG TTT GAG         891
Gln Glu Ser Glu Asp Thr Ala Lys Ala Gly Phe Trp Glu Glu Phe Glu
    235                 240                 245

AGT TTG CAG AAG CAG GAG GTG AAG AAC TTG CAC CAG CGT CTG GAA GGG         939
Ser Leu Gln Lys Gln Glu Val Lys Asn Leu His Gln Arg Leu Glu Gly
250                 255                 260                 265

CAA CGG CCA GAG AAC AAG GGC AAG AAC CGC TAC AAG AAC ATT CTC CCC         987
Gln Arg Pro Glu Asn Lys Gly Lys Asn Arg Tyr Lys Asn Ile Leu Pro
                270                 275                 280

TTT GAC CAC AGC CGA GTG ATC CTG CAG GGA CGG GAC AGT AAC ATC CCC        1035
Phe Asp His Ser Arg Val Ile Leu Gln Gly Arg Asp Ser Asn Ile Pro
            285                 290                 295

GGG TCC GAC TAC ATC AAT GCC AAC TAC ATC AAG AAC CAG CTG CTA GGC        1083
Gly Ser Asp Tyr Ile Asn Ala Asn Tyr Ile Lys Asn Gln Leu Leu Gly
        300                 305                 310
```

| | | | | | | | | | | | | | | | |
|---|---|---|---|---|---|---|---|---|---|---|---|---|---|---|---|
| CCT | GAT | GAG | AAC | GCT | AAG | ACC | TAC | ATC | GCC | AGC | CAG | GGC | TGT | CTG | GAG |
| Pro | Asp | Glu | Asn | Ala | Lys | Thr | Tyr | Ile | Ala | Ser | Gln | Gly | Cys | Leu | Glu |
| | 315 | | | | 320 | | | | | 325 | | | | | |

1131

| | | | | | | | | | | | | | | | |
|---|---|---|---|---|---|---|---|---|---|---|---|---|---|---|---|
| GCC | ACA | GTC | AAT | GAC | TTC | TGG | CAG | ATG | GCG | TGG | CAG | GAG | AAC | AGC | CGT |
| Ala | Thr | Val | Asn | Asp | Phe | Trp | Gln | Met | Ala | Trp | Gln | Glu | Asn | Ser | Arg |
| 330 | | | | | 335 | | | | | 340 | | | | | 345 |

1179

| | | | | | | | | | | | | | | | |
|---|---|---|---|---|---|---|---|---|---|---|---|---|---|---|---|
| GTC | ATC | GTC | ATG | ACC | ACC | CGA | GAG | GTG | GAG | AAA | GGC | CGG | AAC | AAA | TGC |
| Val | Ile | Val | Met | Thr | Thr | Arg | Glu | Val | Glu | Lys | Gly | Arg | Asn | Lys | Cys |
| | | | | 350 | | | | | 355 | | | | | 360 | |

1227

| | | | | | | | | | | | | | | | |
|---|---|---|---|---|---|---|---|---|---|---|---|---|---|---|---|
| GTC | CCA | TAC | TGG | CCC | GAG | GTG | GGC | ATG | CAG | CGT | GCT | TAT | GGG | CCC | TAC |
| Val | Pro | Tyr | Trp | Pro | Glu | Val | Gly | Met | Gln | Arg | Ala | Tyr | Gly | Pro | Tyr |
| | | | 365 | | | | | 370 | | | | | 375 | | |

1275

| | | | | | | | | | | | | | | | |
|---|---|---|---|---|---|---|---|---|---|---|---|---|---|---|---|
| TCT | GTG | ACC | AAC | GTC | GGG | GAG | CAT | GAC | ACA | ACC | GAA | TAC | AAA | CTC | CGT |
| Ser | Val | Thr | Asn | Val | Gly | Glu | His | Asp | Thr | Thr | Glu | Tyr | Lys | Leu | Arg |
| | | 380 | | | | | 385 | | | | | 390 | | | |

1323

| | | | | | | | | | | | | | | | |
|---|---|---|---|---|---|---|---|---|---|---|---|---|---|---|---|
| ACC | TTA | CAG | GTC | TCC | CCG | CTG | GAC | AAT | GGA | GAC | CTG | ATT | CGG | GAG | ATC |
| Thr | Leu | Gln | Val | Ser | Pro | Leu | Asp | Asn | Gly | Asp | Leu | Ile | Arg | Glu | Ile |
| | | 395 | | | | | 400 | | | | | 405 | | | |

1371

| | | | | | | | | | | | | | | | |
|---|---|---|---|---|---|---|---|---|---|---|---|---|---|---|---|
| TGG | CAT | TAC | CAG | TAC | CTG | AGC | TGG | CCC | GAC | CAT | GGG | GTC | CCC | AGT | GAG |
| Trp | His | Tyr | Gln | Tyr | Leu | Ser | Trp | Pro | Asp | His | Gly | Val | Pro | Ser | Glu |
| 410 | | | | | 415 | | | | | 420 | | | | | 425 |

1419

| | | | | | | | | | | | | | | | |
|---|---|---|---|---|---|---|---|---|---|---|---|---|---|---|---|
| CCT | GGG | GGT | GTC | CTC | AGC | TTC | CTG | GAC | CAG | ATC | AAC | CAG | CGG | CAG | GAA |
| Pro | Gly | Gly | Val | Leu | Ser | Phe | Leu | Asp | Gln | Ile | Asn | Gln | Arg | Gln | Glu |
| | | | | 430 | | | | | 435 | | | | | 440 | |

1467

| | | | | | | | | | | | | | | | |
|---|---|---|---|---|---|---|---|---|---|---|---|---|---|---|---|
| AGT | CTG | CCT | CAC | GCA | GGG | CCC | ATC | ATC | GTG | CAC | TGC | AGC | GCC | GGC | ATC |
| Ser | Leu | Pro | His | Ala | Gly | Pro | Ile | Ile | Val | His | Cys | Ser | Ala | Gly | Ile |
| | | | 445 | | | | | 450 | | | | | 455 | | |

1515

| | | | | | | | | | | | | | | | |
|---|---|---|---|---|---|---|---|---|---|---|---|---|---|---|---|
| GGC | CGC | ACA | GGC | ACC | ATC | ATT | GTC | ATC | GAC | ATG | CTC | ATG | GAG | AAC | ATC |
| Gly | Arg | Thr | Gly | Thr | Ile | Ile | Val | Ile | Asp | Met | Leu | Met | Glu | Asn | Ile |
| | | 460 | | | | | 465 | | | | | 470 | | | |

1563

| | | | | | | | | | | | | | | | |
|---|---|---|---|---|---|---|---|---|---|---|---|---|---|---|---|
| TCC | ACC | AAG | GGC | CTG | GAC | TGT | GAC | ATT | GAC | ATC | CAG | AAG | ACC | ATC | CAG |
| Ser | Thr | Lys | Gly | Leu | Asp | Cys | Asp | Ile | Asp | Ile | Gln | Lys | Thr | Ile | Gln |
| 475 | | | | | 480 | | | | | 485 | | | | | |

1611

| | | | | | | | | | | | | | | | |
|---|---|---|---|---|---|---|---|---|---|---|---|---|---|---|---|
| ATG | GTG | CGG | GCG | CAG | CGC | TCG | GGC | ATG | GTG | CAG | ACG | GAG | GCG | CAG | TAC |
| Met | Val | Arg | Ala | Gln | Arg | Ser | Gly | Met | Val | Gln | Thr | Glu | Ala | Gln | Tyr |
| 490 | | | | | 495 | | | | | 500 | | | | | 505 |

1659

| | | | | | | | | | | | | | | | |
|---|---|---|---|---|---|---|---|---|---|---|---|---|---|---|---|
| AAG | TTC | ATC | TAC | GTG | GCC | ATC | GCC | CAG | TTC | ATT | GAA | ACC | ACT | AAG | AAG |
| Lys | Phe | Ile | Tyr | Val | Ala | Ile | Ala | Gln | Phe | Ile | Glu | Thr | Thr | Lys | Lys |
| | | | | 510 | | | | | 515 | | | | | 520 | |

1707

| | | | | | | | | | | | | | | | |
|---|---|---|---|---|---|---|---|---|---|---|---|---|---|---|---|
| AAG | CTG | GAG | GTC | CTG | CAG | TCG | CAG | AAG | GGC | CAG | GAG | TCG | GAG | TAC | GGG |
| Lys | Leu | Glu | Val | Leu | Gln | Ser | Gln | Lys | Gly | Gln | Glu | Ser | Glu | Tyr | Gly |
| | | | 525 | | | | | 530 | | | | | 535 | | |

1755

| | | | | | | | | | | | | | | | |
|---|---|---|---|---|---|---|---|---|---|---|---|---|---|---|---|
| AAC | ATC | ACC | TAT | CCC | CCA | GCC | ATG | AAG | AAT | GCC | CAT | GCC | AAG | GCC | TCC |
| Asn | Ile | Thr | Tyr | Pro | Pro | Ala | Met | Lys | Asn | Ala | His | Ala | Lys | Ala | Ser |
| | | 540 | | | | | 545 | | | | | 550 | | | |

1803

| | | | | | | | | | | | | | | | |
|---|---|---|---|---|---|---|---|---|---|---|---|---|---|---|---|
| CGC | ACC | TCG | TCC | AAA | CAC | AAG | GAG | GAT | GTG | TAT | GAG | AAC | CTG | CAC | ACT |
| Arg | Thr | Ser | Ser | Lys | His | Lys | Glu | Asp | Val | Tyr | Glu | Asn | Leu | His | Thr |
| | | 555 | | | | | 560 | | | | | 565 | | | |

1851

| | | | | | | | | | | | | | | | |
|---|---|---|---|---|---|---|---|---|---|---|---|---|---|---|---|
| AAG | AAC | AAG | AGG | GAG | GAG | AAA | GTG | AAG | AAG | CAG | CGG | TCA | GCA | GAC | AAG |
| Lys | Asn | Lys | Arg | Glu | Glu | Lys | Val | Lys | Lys | Gln | Arg | Ser | Ala | Asp | Lys |
| 570 | | | | | 575 | | | | | 580 | | | | | 585 |

1899

| | | | | | | | | | | |
|---|---|---|---|---|---|---|---|---|---|---|
| GAG | AAG | AGC | AAG | GGT | TCC | CTC | AAG | AGG | AAG | TGAGCGGTGC TGTCCTCAGG |
| Glu | Lys | Ser | Lys | Gly | Ser | Leu | Lys | Arg | Lys | |
| | | | | 590 | | | | | 595 | |

1949

TGGCCATGCC TCAGCCCTGA CCCTGTGGAA GCATTTCGCG ATGGACAGAC TCACAACCTG 2009

AACCTAGGAG TGCCCCATTC TTTTGTAATT TAAATGGCTG CATCCCCCCC ACCTCTCCCT 2069

GACCCTGTAT ATAGCCCAGC CAGGCCCCAG GCAGGGCCAA CCCTTCTCCT CTTGTAAATA 2129

AAGCCCTGGG ATCACT 2145

5,536,636

( 2 ) INFORMATION FOR SEQ ID NO:6:

( i ) SEQUENCE CHARACTERISTICS:
    ( A ) LENGTH: 595 amino acids
    ( B ) TYPE: amino acid
    ( D ) TOPOLOGY: linear ( i i ) MOLECULE TYPE: protein ( x i ) SEQUENCE DESCRIPTION: SEQ ID NO:6:

```
Met Val Arg Trp Phe His Arg Asp Leu Ser Gly Leu Asp Ala Glu Thr
 1               5                  10                  15

Leu Leu Lys Gly Arg Gly Val His Gly Ser Phe Leu Val Trp Pro Ser
            20                  25                  30

Arg Lys Asn Gln Gly Asp Phe Ser Leu Ser Val Arg Val Gly Asp Gln
        35                  40                  45

Val Thr His Ile Arg Ile Gln Asn Ser Gly Asp Phe Tyr Asp Leu Tyr
    50                  55                  60

Gly Gly Glu Lys Phe Ala Thr Leu Thr Glu Leu Val Glu Tyr Tyr Thr
65                  70                  75                  80

Gln Gln Gln Gly Val Val Gln Asp Arg Asp Gly Thr Ile Ile His Leu
                85                  90                  95

Lys Tyr Pro Leu Asn Cys Ser Asp Pro Thr Ser Glu Arg Trp Tyr His
            100                 105                 110

Gly His Met Ser Gly Gly Gln Ala Glu Thr Leu Leu Gln Ala Lys Gly
        115                 120                 125

Glu Pro Trp Thr Phe Leu Val Arg Glu Ser Leu Ser Gln Pro Gly Asp
    130                 135                 140

Phe Val Leu Ser Val Leu Ser Asp Gln Pro Lys Ala Gly Pro Gly Ser
145                 150                 155                 160

Pro Leu Arg Val Thr His Ile Lys Val Met Cys Glu Gly Gly Arg Tyr
                165                 170                 175

Thr Val Gly Gly Leu Glu Thr Phe Asp Ser Leu Thr Asp Leu Val Glu
            180                 185                 190

His Phe Lys Lys Thr Gly Ile Glu Glu Ala Ser Gly Ala Phe Val Tyr
        195                 200                 205

Leu Arg Gln Pro Tyr Tyr Ala Thr Arg Val Asn Ala Ala Asp Ile Glu
    210                 215                 220

Asn Arg Val Leu Glu Leu Asn Lys Lys Gln Glu Ser Glu Asp Thr Ala
225                 230                 235                 240

Lys Ala Gly Phe Trp Glu Glu Phe Glu Ser Leu Gln Lys Gln Glu Val
                245                 250                 255

Lys Asn Leu His Gln Arg Leu Glu Gly Gln Arg Pro Glu Asn Lys Gly
            260                 265                 270

Lys Asn Arg Tyr Lys Asn Ile Leu Pro Phe Asp His Ser Arg Val Ile
        275                 280                 285

Leu Gln Gly Arg Asp Ser Asn Ile Pro Gly Ser Asp Tyr Ile Asn Ala
    290                 295                 300

Asn Tyr Ile Lys Asn Gln Leu Leu Gly Pro Asp Glu Asn Ala Lys Thr
305                 310                 315                 320

Tyr Ile Ala Ser Gln Gly Cys Leu Glu Ala Thr Val Asn Asp Phe Trp
                325                 330                 335

Gln Met Ala Trp Gln Glu Asn Ser Arg Val Ile Val Met Thr Thr Arg
            340                 345                 350

Glu Val Glu Lys Gly Arg Asn Lys Cys Val Pro Tyr Trp Pro Glu Val
        355                 360                 365
```

| | | | | | | | | | | | | | | |
|---|---|---|---|---|---|---|---|---|---|---|---|---|---|---|
|Gly|Met 370|Gln|Arg|Ala|Tyr|Gly 375|Pro|Tyr|Ser|Val|Thr 380|Asn|Val|Gly|Glu|
|His 385|Asp|Thr|Thr|Glu|Tyr 390|Lys|Leu|Arg|Thr|Leu 395|Gln|Val|Ser|Pro|Leu 400|
|Asp|Asn|Gly|Asp|Leu 405|Ile|Arg|Glu|Ile|Trp 410|His|Tyr|Gln|Tyr|Leu 415|Ser|
|Trp|Pro|Asp|His 420|Gly|Val|Pro|Ser|Glu 425|Pro|Gly|Gly|Val|Leu 430|Ser|Phe|
|Leu|Asp|Gln 435|Ile|Asn|Gln|Arg|Gln 440|Glu|Ser|Leu|Pro|His 445|Ala|Gly|Pro|
|Ile|Ile 450|Val|His|Cys|Ser|Ala 455|Gly|Ile|Gly|Arg|Thr 460|Gly|Thr|Ile|Ile|
|Val 465|Ile|Asp|Met|Leu|Met 470|Glu|Asn|Ile|Ser|Thr 475|Lys|Gly|Leu|Asp|Cys 480|
|Asp|Ile|Asp|Ile|Gln 485|Lys|Thr|Ile|Gln|Met 490|Val|Arg|Ala|Gln|Arg 495|Ser|
|Gly|Met|Val|Gln 500|Thr|Glu|Ala|Gln|Tyr 505|Lys|Phe|Ile|Tyr|Val 510|Ala|Ile|
|Ala|Gln|Phe 515|Ile|Glu|Thr|Thr|Lys 520|Lys|Lys|Leu|Glu|Val 525|Leu|Gln|Ser|
|Gln|Lys 530|Gly|Gln|Glu|Ser|Glu 535|Tyr|Gly|Asn|Ile|Thr 540|Tyr|Pro|Pro|Ala|
|Met 545|Lys|Asn|Ala|His|Ala 550|Lys|Ala|Ser|Arg|Thr 555|Ser|Ser|Lys|His|Lys 560|
|Glu|Asp|Val|Tyr|Glu 565|Asn|Leu|His|Thr|Lys 570|Asn|Lys|Arg|Glu|Glu 575|Lys|
|Val|Lys|Lys|Gln|Arg 580|Ser|Ala|Asp|Lys 585|Glu|Lys|Ser|Lys|Gly 590|Ser|Leu|
|Lys|Arg|Lys 595| | | | | | | | | | | | | |

( 2 ) INFORMATION FOR SEQ ID NO:7:

( i ) SEQUENCE CHARACTERISTICS:
        ( A ) LENGTH: 2143 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 145..2037

( x i ) SEQUENCE DESCRIPTION: SEQ ID NO:7:

```
CGGCAGAACT GGGACCACCG GGGGTGGTGA GGCGGCCCGG CACTGGGAGC TGCATCTGAG      60

GCTTAGTCCC TGAGCTCTCT GCCTGCCCAG ACTAGCTGCA CCTCCTCATT CCCTGCGCCC     120

CCTTCCTCTC CGGAAGCCCC CAGG ATG GTG AGG TGG TTT CAC CGA GAC CTC       171
                             Met Val Arg Trp Phe His Arg Asp Leu
                              1               5

AGT GGG CTG GAT GCA GAG ACC CTG CTC AAG GGC CGA GGT GTC CAC GGT       219
Ser Gly Leu Asp Ala Glu Thr Leu Leu Lys Gly Arg Gly Val His Gly
 10                  15                  20                  25

AGC TTC CTG GCT CGG CCC AGT CGC AAG AAC CAG GGT GAC TTC TCG CTC       267
Ser Phe Leu Ala Arg Pro Ser Arg Lys Asn Gln Gly Asp Phe Ser Leu
                 30                  35                  40

TCC GTC AGG GTG GGG GAT CAG GTG ACC CAT ATT CGG ATC CAG AAC TCA       315
```

|   |   |   |   |   |   |   |   |   |   |   |   |   |   |   |   |
|---|---|---|---|---|---|---|---|---|---|---|---|---|---|---|---|
| Ser | Val | Arg | Val<br>45 | Gly | Asp | Gln | Val | Thr<br>50 | His | Ile | Arg | Ile | Gln<br>55 | Asn | Ser |

| GGG | GAT | TTC | TAT | GAC | CTG | TAT | GGA | GGG | GAG | AAG | TTT | GCG | ACT | CTG | ACA | 363 |
|---|---|---|---|---|---|---|---|---|---|---|---|---|---|---|---|---|
| Gly | Asp | Phe<br>60 | Tyr | Asp | Leu | Tyr | Gly<br>65 | Gly | Glu | Lys | Phe | Ala<br>70 | Thr | Leu | Thr | |

| GAG | CTG | GTG | GAG | TAC | TAC | ACT | CAG | CAG | CAG | GGT | GTG | GTG | CAG | GAC | CGC | 411 |
|---|---|---|---|---|---|---|---|---|---|---|---|---|---|---|---|---|
| Glu | Leu<br>75 | Val | Glu | Tyr | Tyr | Thr<br>80 | Gln | Gln | Gln | Gly | Val<br>85 | Val | Gln | Asp | Arg | |

| GAC | GGC | ACC | ATC | ATC | CAC | CTC | AAG | TAC | CCG | CTG | AAC | TGC | TCC | GAT | CCC | 459 |
|---|---|---|---|---|---|---|---|---|---|---|---|---|---|---|---|---|
| Asp | Gly<br>90 | Thr | Ile | Ile | His<br>95 | Leu | Lys | Tyr | Pro | Leu<br>100 | Asn | Cys | Ser | Asp<br>105 | Pro | |

| ACT | AGT | GAG | AGG | TGG | TAC | CAT | GGC | CAC | ATG | TCT | GGC | GGG | CAG | GCA | GAG | 507 |
|---|---|---|---|---|---|---|---|---|---|---|---|---|---|---|---|---|
| Thr | Ser | Glu | Arg | Trp<br>110 | Tyr | His | Gly | His | Met<br>115 | Ser | Gly | Gly | Gln | Ala<br>120 | Glu | |

| ACG | CTG | CTG | CAG | GCC | AAG | GGC | GAG | CCC | TGG | ACG | TTT | CTT | GTG | CGT | GAG | 555 |
|---|---|---|---|---|---|---|---|---|---|---|---|---|---|---|---|---|
| Thr | Leu | Leu | Gln<br>125 | Ala | Lys | Gly | Glu | Pro<br>130 | Trp | Thr | Phe | Leu | Val<br>135 | Arg | Glu | |

| AGC | CTC | AGC | CAG | CCT | GGA | GAC | TTC | GTG | CTT | TCT | GTG | CTC | AGT | GAC | CAG | 603 |
|---|---|---|---|---|---|---|---|---|---|---|---|---|---|---|---|---|
| Ser | Leu | Ser<br>140 | Gln | Pro | Gly | Asp | Phe<br>145 | Val | Leu | Ser | Val | Leu<br>150 | Ser | Asp | Gln | |

| CCC | AAG | GCT | GGC | CCA | GGC | TCC | CCG | CTC | AGG | GTC | ACC | CAC | ATC | AAG | GTC | 651 |
|---|---|---|---|---|---|---|---|---|---|---|---|---|---|---|---|---|
| Pro | Lys<br>155 | Ala | Gly | Pro | Gly | Ser<br>160 | Pro | Leu | Arg | Val | Thr<br>165 | His | Ile | Lys | Val | |

| ATG | TGC | GAG | GGT | GGA | CGC | TAC | ACA | GTG | GGT | GGT | TTG | GAG | ACC | TTC | GAC | 699 |
|---|---|---|---|---|---|---|---|---|---|---|---|---|---|---|---|---|
| Met<br>170 | Cys | Glu | Gly | Gly | Arg<br>175 | Tyr | Thr | Val | Gly | Gly<br>180 | Leu | Glu | Thr | Phe | Asp<br>185 | |

| AGC | CTC | ACG | GAC | CTG | GTG | GAG | CAT | TTC | AAG | AAG | ACG | GGG | ATT | GAG | GAG | 747 |
|---|---|---|---|---|---|---|---|---|---|---|---|---|---|---|---|---|
| Ser | Leu | Thr | Asp | Leu<br>190 | Val | Glu | His | Phe | Lys<br>195 | Lys | Thr | Gly | Ile | Glu<br>200 | Glu | |

| GCC | TCA | GGC | GCC | TTT | GTC | TAC | CTG | CGG | CAG | CCG | TAC | TAT | GCC | ACG | AGG | 795 |
|---|---|---|---|---|---|---|---|---|---|---|---|---|---|---|---|---|
| Ala | Ser | Gly | Ala | Phe<br>205 | Val | Tyr | Leu | Arg | Gln<br>210 | Pro | Tyr | Tyr | Ala | Thr<br>215 | Arg | |

| GTG | AAT | GCG | GCT | GAC | ATT | GAG | AAC | CGA | GTG | TTG | GAA | CTG | AAC | AAG | AAG | 843 |
|---|---|---|---|---|---|---|---|---|---|---|---|---|---|---|---|---|
| Val | Asn | Ala<br>220 | Ala | Asp | Ile | Glu | Asn<br>225 | Arg | Val | Leu | Glu | Leu<br>230 | Asn | Lys | Lys | |

| CAG | GAG | TCC | GAG | GAT | ACA | GCC | AAG | GCT | GGC | TTC | TGG | GAG | GAG | TTT | GAG | 891 |
|---|---|---|---|---|---|---|---|---|---|---|---|---|---|---|---|---|
| Gln | Glu | Ser<br>235 | Glu | Asp | Thr | Ala | Lys<br>240 | Ala | Gly | Phe | Trp | Glu<br>245 | Glu | Phe | Glu | |

| AGT | TTG | CAG | AAG | CAG | GAG | GTG | AAG | AAC | TTG | CAC | CAG | CGT | CTG | GAA | GGG | 939 |
|---|---|---|---|---|---|---|---|---|---|---|---|---|---|---|---|---|
| Ser<br>250 | Leu | Gln | Lys | Gln | Glu<br>255 | Val | Lys | Asn | Leu | His<br>260 | Gln | Arg | Leu | Glu | Gly<br>265 | |

| CAA | CGG | CCA | GAG | AAC | AAG | GGC | AAG | AAC | CGC | TAC | AAG | AAC | ATT | CTC | CCC | 987 |
|---|---|---|---|---|---|---|---|---|---|---|---|---|---|---|---|---|
| Gln | Arg | Pro | Glu | Asn<br>270 | Lys | Gly | Lys | Asn | Arg<br>275 | Tyr | Lys | Asn | Ile | Leu<br>280 | Pro | |

| TTT | GAC | CAC | AGC | CGA | GTG | ATC | CTG | CAG | GGA | CGG | GAC | AGT | AAC | ATC | CCC | 1035 |
|---|---|---|---|---|---|---|---|---|---|---|---|---|---|---|---|---|
| Phe | Asp | His | Ser<br>285 | Arg | Val | Ile | Leu | Gln<br>290 | Gly | Arg | Asp | Ser | Asn<br>295 | Ile | Pro | |

| GGG | TCC | GAC | TAC | ATC | AAT | GCC | AAC | TAC | ATC | AAG | AAC | CAG | CTG | CTA | GGC | 1083 |
|---|---|---|---|---|---|---|---|---|---|---|---|---|---|---|---|---|
| Gly | Ser | Asp<br>300 | Tyr | Ile | Asn | Ala | Asn<br>305 | Tyr | Ile | Lys | Asn | Gln<br>310 | Leu | Leu | Gly | |

| CCT | GAT | GAG | AAC | GCT | AAG | ACC | TAC | ATC | GCC | AGC | CAG | GGC | TGT | CTG | GAG | 1131 |
|---|---|---|---|---|---|---|---|---|---|---|---|---|---|---|---|---|
| Pro | Asp | Glu<br>315 | Asn | Ala | Lys | Thr<br>320 | Tyr | Ile | Ala | Ser | Gln<br>325 | Gly | Cys | Leu | Glu | |

| GCC | ACG | GTC | AAT | GAC | TTC | TGG | CAG | ATG | GCG | TGG | CAG | GAG | AAC | AGC | CGT | 1179 |
|---|---|---|---|---|---|---|---|---|---|---|---|---|---|---|---|---|
| Ala<br>330 | Thr | Val | Asn | Asp | Phe<br>335 | Trp | Gln | Met | Ala | Trp<br>340 | Gln | Glu | Asn | Ser | Arg<br>345 | |

| GTC | ATC | GTC | ATG | ACC | ACC | CGA | GAG | GTG | GAG | AAA | GGC | CGG | AAC | AAA | TGC | 1227 |
|---|---|---|---|---|---|---|---|---|---|---|---|---|---|---|---|---|
| Val | Ile | Val | Met | Thr<br>350 | Thr | Arg | Glu | Val | Glu<br>355 | Lys | Gly | Arg | Asn | Lys<br>360 | Cys | |

| GTC | CCA | TAC | TGG | CCC | GAG | GTG | GGC | ATG | CAG | CGT | GCT | TAT | GGG | CCC | TAC | 1275 |

| | | | | | | | | | | | | | | | | |
|---|---|---|---|---|---|---|---|---|---|---|---|---|---|---|---|---|
| Val | Pro | Tyr | Trp<br>365 | Pro | Glu | Val | Gly | Met<br>370 | Gln | Arg | Ala | Tyr<br>375 | Gly | Pro | Tyr | |
| TCT<br>Ser | GTG<br>Val | ACC<br>Thr<br>380 | AAC<br>Asn | TGC<br>Cys | GGG<br>Gly | GAG<br>Glu | CAT<br>His<br>385 | GAC<br>Asp | ACA<br>Thr | ACC<br>Thr | GAA<br>Glu | TAC<br>Tyr<br>390 | AAA<br>Lys | CTC<br>Leu | CGT<br>Arg | 1323 |
| ACC<br>Thr | TTA<br>Leu<br>395 | CAG<br>Gln | GTC<br>Val | TCC<br>Ser | CCG<br>Pro | CTG<br>Leu<br>400 | GAC<br>Asp | AAT<br>Asn | GGA<br>Gly | GAC<br>Asp | CTG<br>Leu<br>405 | ATT<br>Ile | CGG<br>Arg | GAG<br>Glu | ATC<br>Ile | 1371 |
| TGG<br>Trp<br>410 | CAT<br>His | TAC<br>Tyr | CAG<br>Gln | TAC<br>Tyr | CTG<br>Leu<br>415 | AGC<br>Ser | TGG<br>Trp | CCC<br>Pro | GAC<br>Asp | CAT<br>His<br>420 | GGG<br>Gly | GTC<br>Val | CCC<br>Pro | AGT<br>Ser | GAG<br>Glu<br>425 | 1419 |
| CCT<br>Pro | GGG<br>Gly | GGT<br>Gly | GTC<br>Val | CTC<br>Leu<br>430 | AGC<br>Ser | TTC<br>Phe | CTG<br>Leu | GAC<br>Asp | CAG<br>Gln<br>435 | ATC<br>Ile | AAC<br>Asn | CAG<br>Gln | CGG<br>Arg | CAG<br>Gln<br>440 | GAA<br>Glu | 1467 |
| AGT<br>Ser | CTG<br>Leu | CCT<br>Pro | CAC<br>His<br>445 | GCA<br>Ala | GGG<br>Gly | CCC<br>Pro | ATC<br>Ile | ATC<br>Ile<br>450 | GTG<br>Val | CAC<br>His | TGC<br>Cys | AGC<br>Ser | GCC<br>Ala<br>455 | GGC<br>Gly | ATC<br>Ile | 1515 |
| GGC<br>Gly | CGC<br>Arg | ACA<br>Thr<br>460 | GGC<br>Gly | ACC<br>Thr | ATC<br>Ile | ATT<br>Ile | GTC<br>Val<br>465 | ATC<br>Ile | GAC<br>Asp | ATG<br>Met | CTC<br>Leu | ATG<br>Met<br>470 | GAG<br>Glu | AAC<br>Asn | ATC<br>Ile | 1563 |
| TCC<br>Ser | ACC<br>Thr<br>475 | AAG<br>Lys | GGC<br>Gly | CTG<br>Leu | GAC<br>Asp | TGT<br>Cys<br>480 | GAC<br>Asp | ATT<br>Ile | GAC<br>Asp | ATC<br>Ile | CAG<br>Gln<br>485 | AAG<br>Lys | ACC<br>Thr | ATC<br>Ile | CAG<br>Gln | 1611 |
| ATG<br>Met<br>490 | GTG<br>Val | CGG<br>Arg | GCG<br>Ala | CAG<br>Gln | CGC<br>Arg<br>495 | TCG<br>Ser | GGC<br>Gly | ATG<br>Met | GTG<br>Val | CAG<br>Gln<br>500 | ACG<br>Thr | GAG<br>Glu | GCG<br>Ala | CAG<br>Gln | TAC<br>Tyr<br>505 | 1659 |
| AAG<br>Lys | TTC<br>Phe | ATC<br>Ile | TAC<br>Tyr | GTG<br>Val<br>510 | GCC<br>Ala | ATC<br>Ile | GCC<br>Ala | CAG<br>Gln | TTC<br>Phe<br>515 | ATT<br>Ile | GAA<br>Glu | ACC<br>Thr | ACT<br>Thr | AAG<br>Lys<br>520 | AAG<br>Lys | 1707 |
| AAG<br>Lys | CTG<br>Leu | GAG<br>Glu | GTC<br>Val<br>525 | CTG<br>Leu | CAG<br>Gln | TCG<br>Ser | CAG<br>Gln | AAG<br>Lys<br>530 | GGC<br>Gly | CAG<br>Gln | GAG<br>Glu | TCG<br>Ser | GAG<br>Glu<br>535 | TAC<br>Tyr | GGG<br>Gly | 1755 |
| AAC<br>Asn | ATC<br>Ile | ACC<br>Thr<br>540 | TAT<br>Tyr | CCC<br>Pro | CCA<br>Pro | GCC<br>Ala | ATG<br>Met<br>545 | AAG<br>Lys | AAT<br>Asn | GCC<br>Ala | CAT<br>His | GCC<br>Ala<br>550 | AAG<br>Lys | GCC<br>Ala | TCC<br>Ser | 1803 |
| CGC<br>Arg | ACC<br>Thr<br>555 | TCG<br>Ser | TCC<br>Ser | AAA<br>Lys | CAC<br>His<br>560 | AAG<br>Lys | GAG<br>Glu | GAT<br>Asp | GTG<br>Val | TAT<br>Tyr<br>565 | GAG<br>Glu | AAC<br>Asn | CTG<br>Leu | CAC<br>His | ACT<br>Thr | 1851 |
| AAG<br>Lys<br>570 | AAC<br>Asn | AAG<br>Lys | AGG<br>Arg | GAG<br>Glu | GAA<br>Glu<br>575 | AGT<br>Ser | GAA<br>Glu | GAA<br>Glu | GCA<br>Ala | GCG<br>Ala<br>580 | GTC<br>Val | AGC<br>Ser | AGA<br>Arg | CAA<br>Gln | GGA<br>Gly<br>585 | 1899 |
| GAA<br>Glu | GAG<br>Glu | CAA<br>Gln | GGG<br>Gly | TTC<br>Phe<br>590 | CCT<br>Pro | CAA<br>Gln | GAG<br>Glu | GAA<br>Glu | GTG<br>Val<br>595 | AGC<br>Ser | GGT<br>Gly | GCT<br>Ala | GTC<br>Val | CTC<br>Leu<br>600 | AGG<br>Arg | 1947 |
| TGG<br>Trp | CCA<br>Pro | TGC<br>Cys | CTC<br>Leu<br>605 | AGC<br>Ser | CCT<br>Pro | GAC<br>Asp | CCT<br>Pro | GTG<br>Val<br>610 | GAA<br>Glu | GCA<br>Ala | TTT<br>Phe | CGC<br>Arg | GAT<br>Asp<br>615 | GGA<br>Gly | CAG<br>Gln | 1995 |
| ACT<br>Thr | CAC<br>His | AAC<br>Asn<br>620 | CTG<br>Leu | AAC<br>Asn | CTA<br>Leu | GGA<br>Gly | GTG<br>Val<br>625 | CCC<br>Pro | CAT<br>His | TCT<br>Ser | TTT<br>Phe | GTA<br>Val<br>630 | ATT<br>Ile | | | 2037 |

TAAATGGCTG CATCCCCCCC ACCTCTCCCT GACCCTGTAT ATAGCCCAGC CAGGCCCCAG 2097

GCAGGGCCAA CCCTTCTCCT CTTGTAAATA AAGCCCTGGG ATCACT 2143

( 2 ) INFORMATION FOR SEQ ID NO:8:

( i ) SEQUENCE CHARACTERISTICS:
        ( A ) LENGTH: 631 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | |
|---|---|---|---|---|---|---|---|---|---|---|---|---|---|---|
| Met | Val | Arg | Trp | Phe | His | Arg | Asp | Leu | Ser | Gly | Leu | Asp | Ala | Glu | Thr |
| 1 | | | | 5 | | | | | 10 | | | | | 15 | |
| Leu | Leu | Lys | Gly | Arg | Gly | Val | His | Gly | Ser | Phe | Leu | Ala | Arg | Pro | Ser |
| | | | 20 | | | | | 25 | | | | | 30 | | |
| Arg | Lys | Asn | Gln | Gly | Asp | Phe | Ser | Leu | Ser | Val | Arg | Val | Gly | Asp | Gln |
| | | 35 | | | | | 40 | | | | | 45 | | | |
| Val | Thr | His | Ile | Arg | Ile | Gln | Asn | Ser | Gly | Asp | Phe | Tyr | Asp | Leu | Tyr |
| | 50 | | | | | 55 | | | | | 60 | | | | |
| Gly | Gly | Glu | Lys | Phe | Ala | Thr | Leu | Thr | Glu | Leu | Val | Glu | Tyr | Tyr | Thr |
| 65 | | | | | 70 | | | | | 75 | | | | | 80 |
| Gln | Gln | Gln | Gly | Val | Val | Gln | Asp | Arg | Asp | Gly | Thr | Ile | Ile | His | Leu |
| | | | | 85 | | | | | 90 | | | | | 95 | |
| Lys | Tyr | Pro | Leu | Asn | Cys | Ser | Asp | Pro | Thr | Ser | Glu | Arg | Trp | Tyr | His |
| | | | 100 | | | | | 105 | | | | | 110 | | |
| Gly | His | Met | Ser | Gly | Gly | Gln | Ala | Glu | Thr | Leu | Leu | Gln | Ala | Lys | Gly |
| | | 115 | | | | | 120 | | | | | 125 | | | |
| Glu | Pro | Trp | Thr | Phe | Leu | Val | Arg | Glu | Ser | Leu | Ser | Gln | Pro | Gly | Asp |
| | 130 | | | | | 135 | | | | | 140 | | | | |
| Phe | Val | Leu | Ser | Val | Leu | Ser | Asp | Gln | Pro | Lys | Ala | Gly | Pro | Gly | Ser |
| 145 | | | | | 150 | | | | | 155 | | | | | 160 |
| Pro | Leu | Arg | Val | Thr | His | Ile | Lys | Val | Met | Cys | Glu | Gly | Gly | Arg | Tyr |
| | | | | 165 | | | | | 170 | | | | | 175 | |
| Thr | Val | Gly | Gly | Leu | Glu | Thr | Phe | Asp | Ser | Leu | Thr | Asp | Leu | Val | Glu |
| | | | 180 | | | | | 185 | | | | | 190 | | |
| His | Phe | Lys | Lys | Thr | Gly | Ile | Glu | Glu | Ala | Ser | Gly | Ala | Phe | Val | Tyr |
| | | 195 | | | | | 200 | | | | | 205 | | | |
| Leu | Arg | Gln | Pro | Tyr | Tyr | Ala | Thr | Arg | Val | Asn | Ala | Ala | Asp | Ile | Glu |
| | 210 | | | | | 215 | | | | | 220 | | | | |
| Asn | Arg | Val | Leu | Glu | Leu | Asn | Lys | Lys | Gln | Glu | Ser | Glu | Asp | Thr | Ala |
| 225 | | | | | 230 | | | | | 235 | | | | | 240 |
| Lys | Ala | Gly | Phe | Trp | Glu | Glu | Phe | Glu | Ser | Leu | Gln | Lys | Gln | Glu | Val |
| | | | | 245 | | | | | 250 | | | | | 255 | |
| Lys | Asn | Leu | His | Gln | Arg | Leu | Glu | Gly | Gln | Arg | Pro | Glu | Asn | Lys | Gly |
| | | | 260 | | | | | 265 | | | | | 270 | | |
| Lys | Asn | Arg | Tyr | Lys | Asn | Ile | Leu | Pro | Phe | Asp | His | Ser | Arg | Val | Ile |
| | | 275 | | | | | 280 | | | | | 285 | | | |
| Leu | Gln | Gly | Arg | Asp | Ser | Asn | Ile | Pro | Gly | Ser | Asp | Tyr | Ile | Asn | Ala |
| | 290 | | | | | 295 | | | | | 300 | | | | |
| Asn | Tyr | Ile | Lys | Asn | Gln | Leu | Leu | Gly | Pro | Asp | Glu | Asn | Ala | Lys | Thr |
| 305 | | | | | 310 | | | | | 315 | | | | | 320 |
| Tyr | Ile | Ala | Ser | Gln | Gly | Cys | Leu | Glu | Ala | Thr | Val | Asn | Asp | Phe | Trp |
| | | | | 325 | | | | | 330 | | | | | 335 | |
| Gln | Met | Ala | Trp | Gln | Glu | Asn | Ser | Arg | Val | Ile | Val | Met | Thr | Thr | Arg |
| | | | 340 | | | | | 345 | | | | | 350 | | |
| Glu | Val | Glu | Lys | Gly | Arg | Asn | Lys | Cys | Val | Pro | Tyr | Trp | Pro | Glu | Val |
| | | 355 | | | | | 360 | | | | | 365 | | | |
| Gly | Met | Gln | Arg | Ala | Tyr | Gly | Pro | Tyr | Ser | Val | Thr | Asn | Cys | Gly | Glu |
| | 370 | | | | | 375 | | | | | 380 | | | | |
| His | Asp | Thr | Thr | Glu | Tyr | Lys | Leu | Arg | Thr | Leu | Gln | Val | Ser | Pro | Leu |
| 385 | | | | | 390 | | | | | 395 | | | | | 400 |
| Asp | Asn | Gly | Asp | Leu | Ile | Arg | Glu | Ile | Trp | His | Tyr | Gln | Tyr | Leu | Ser |
| | | | | 405 | | | | | 410 | | | | | 415 | |

| | | | | | | | | | | | | | | |
|---|---|---|---|---|---|---|---|---|---|---|---|---|---|---|
| Trp | Pro | Asp | His<br>420 | Gly | Val | Pro | Ser | Glu<br>425 | Pro | Gly | Gly | Val | Leu<br>430 | Ser | Phe |
| Leu | Asp | Gln<br>435 | Ile | Asn | Gln | Arg | Gln<br>440 | Glu | Ser | Leu | Pro | His<br>445 | Ala | Gly | Pro |
| Ile | Ile | Val<br>450 | His | Cys | Ser | Ala<br>455 | Gly | Ile | Gly | Arg | Thr<br>460 | Gly | Thr | Ile | Ile |
| Val<br>465 | Ile | Asp | Met | Leu | Met<br>470 | Glu | Asn | Ile | Ser | Thr<br>475 | Lys | Gly | Leu | Asp | Cys<br>480 |
| Asp | Ile | Asp | Ile | Gln<br>485 | Lys | Thr | Ile | Gln | Met<br>490 | Val | Arg | Ala | Gln | Arg<br>495 | Ser |
| Gly | Met | Val | Gln<br>500 | Thr | Glu | Ala | Gln | Tyr<br>505 | Lys | Phe | Ile | Tyr | Val<br>510 | Ala | Ile |
| Ala | Gln | Phe<br>515 | Ile | Glu | Thr | Thr | Lys<br>520 | Lys | Lys | Leu | Glu | Val<br>525 | Leu | Gln | Ser |
| Gln | Lys<br>530 | Gly | Gln | Glu | Ser | Glu<br>535 | Tyr | Gly | Asn | Ile | Thr<br>540 | Tyr | Pro | Pro | Ala |
| Met<br>545 | Lys | Asn | Ala | His | Ala<br>550 | Lys | Ala | Ser | Arg | Thr<br>555 | Ser | Ser | Lys | His | Lys<br>560 |
| Glu | Asp | Val | Tyr | Glu<br>565 | Asn | Leu | His | Thr | Lys<br>570 | Asn | Lys | Arg | Glu | Glu<br>575 | Ser |
| Glu | Glu | Ala | Ala<br>580 | Val | Ser | Arg | Gln | Gly<br>585 | Glu | Glu | Gln | Gly | Phe<br>590 | Pro | Gln |
| Glu | Glu | Val<br>595 | Ser | Gly | Ala | Val | Leu<br>600 | Arg | Trp | Pro | Cys | Leu<br>605 | Ser | Pro | Asp |
| Pro | Val<br>610 | Glu | Ala | Phe | Arg | Asp<br>615 | Gly | Gln | Thr | His | Asn<br>620 | Leu | Asn | Leu | Gly |
| Val<br>625 | Pro | His | Ser | Phe | Val<br>630 | Ile | | | | | | | | | |

( 2 ) INFORMATION FOR SEQ ID NO:9:

( i ) SEQUENCE CHARACTERISTICS:
        ( A ) LENGTH: 380 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..380

( x i ) SEQUENCE DESCRIPTION: SEQ ID NO:9:

| | | | | | | | | | | | | | | | | |
|---|---|---|---|---|---|---|---|---|---|---|---|---|---|---|---|---|
| AAA | TGT | CCG | CAA | TAT | TGG | CCT | GAT | GAG | TGT | GCA | CTC | AAA | GAG | TAT | GGC | 48 |
| Lys<br>1 | Cys | Pro | Gln | Tyr<br>5 | Trp | Pro | Asp | Glu | Cys<br>10 | Ala | Leu | Lys | Glu | Tyr<br>15 | Gly | |
| GTC | ATG | CGT | GTG | AGG | AAC | GTC | AGA | GAA | AGT | GCT | GCG | CAT | GAC | TAC | ACC | 96 |
| Val | Met | Arg | Val<br>20 | Arg | Asn | Val | Arg | Glu<br>25 | Ser | Ala | Ala | His | Asp<br>30 | Tyr | Thr | |
| TTA | CGA | GAA | GTG | AAA | GTG | TGT | AAG | GTC | GGA | CAA | GGA | AAC | ACA | GAG | AGA | 144 |
| Leu | Arg | Glu<br>35 | Val | Lys | Val | Cys | Lys<br>40 | Val | Gly | Gln | Gly | Asn<br>45 | Thr | Glu | Arg | |
| ACC | GTC | TGG | CAG | TAC | CAC | TTT | CGG | ACC | TGG | CCA | GAC | CAC | GGT | GTG | CCT | 192 |
| Thr | Val<br>50 | Trp | Gln | Tyr | His | Phe<br>55 | Arg | Thr | Trp | Pro | Asp<br>60 | His | Gly | Val | Pro | |
| AGT | GAC | CCT | GGA | GGT | GTG | CTG | GAC | TTG | GTG | GAG | GAG | GTC | CAC | CAC | AAG | 240 |
| Ser<br>65 | Asp | Pro | Gly | Gly | Val<br>70 | Leu | Asp | Leu | Val | Glu<br>75 | Glu | Val | His | His | Lys<br>80 | |

| | | | | | | | | | | | | | | | | |
|---|---|---|---|---|---|---|---|---|---|---|---|---|---|---|---|---|
| CAG | GAG | AGC | ATC | GTG | GAT | GCA | GGC | CCT | GTC | GTG | GTT | CAC | TGC | AGT | GCT | 288 |
| Gln | Glu | Ser | Ile | Val | Asp | Ala | Gly | Pro | Val | Val | Val | His | Cys | Ser | Ala | |
| | | | | 85 | | | | | 90 | | | | | 95 | | |
| GGG | ATT | GGC | CGG | ACA | GGA | ACG | TTC | ATT | GTG | ATT | GAT | ATC | CTT | ATT | GAC | 336 |
| Gly | Ile | Gly | Arg | Thr | Gly | Thr | Phe | Ile | Val | Ile | Asp | Ile | Leu | Ile | Asp | |
| | | | 100 | | | | | 105 | | | | | 110 | | | |
| ATC | ATC | CGA | GAG | AAA | GGT | GTG | GAC | TGT | GAC | ATC | GAC | GTT | CCT | AA | | 380 |
| Ile | Ile | Arg | Glu | Lys | Gly | Val | Asp | Cys | Asp | Ile | Asp | Val | Pro | | | |
| | | 115 | | | | | 120 | | | | | 125 | | | | |

(2) INFORMATION FOR SEQ ID NO:10:

(i) SEQUENCE CHARACTERISTICS:
        (A) LENGTH: 126 amino acids
        (B) TYPE: amino acid
        (D) TOPOLOGY: linear (ii) MOLECULE TYPE: protein (xi) SEQUENCE DESCRIPTION: SEQ ID NO:10:

| | | | | | | | | | | | | | | | |
|---|---|---|---|---|---|---|---|---|---|---|---|---|---|---|---|
| Lys | Cys | Pro | Gln | Tyr | Trp | Pro | Asp | Glu | Cys | Ala | Leu | Lys | Glu | Tyr | Gly |
| 1 | | | | 5 | | | | | 10 | | | | | 15 | |
| Val | Met | Arg | Val | Arg | Asn | Val | Arg | Glu | Ser | Ala | Ala | His | Asp | Tyr | Thr |
| | | | 20 | | | | | 25 | | | | | 30 | | |
| Leu | Arg | Glu | Val | Lys | Val | Cys | Lys | Val | Gly | Gln | Gly | Asn | Thr | Glu | Arg |
| | | 35 | | | | | 40 | | | | | 45 | | | |
| Thr | Val | Trp | Gln | Tyr | His | Phe | Arg | Thr | Trp | Pro | Asp | His | Gly | Val | Pro |
| | 50 | | | | | 55 | | | | | 60 | | | | |
| Ser | Asp | Pro | Gly | Gly | Val | Leu | Asp | Leu | Val | Glu | Glu | Val | His | His | Lys |
| 65 | | | | | 70 | | | | | 75 | | | | | 80 |
| Gln | Glu | Ser | Ile | Val | Asp | Ala | Gly | Pro | Val | Val | Val | His | Cys | Ser | Ala |
| | | | | 85 | | | | | 90 | | | | | 95 | |
| Gly | Ile | Gly | Arg | Thr | Gly | Thr | Phe | Ile | Val | Ile | Asp | Ile | Leu | Ile | Asp |
| | | | 100 | | | | | 105 | | | | | 110 | | |
| Ile | Ile | Arg | Glu | Lys | Gly | Val | Asp | Cys | Asp | Ile | Asp | Val | Pro | | |
| | | 115 | | | | | 120 | | | | | 125 | | | |

(2) INFORMATION FOR SEQ ID NO:11:

(i) SEQUENCE CHARACTERISTICS:
        (A) LENGTH: 2276 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 114..1893

(xi) SEQUENCE DESCRIPTION: SEQ ID NO:11:

| | | | | | | |
|---|---|---|---|---|---|---|
| CTGCCCCGCG | TCCGGTCCCG | AGCGGGCCTC | CCTCGGGCCA | GCCCGATGTG | ACCGAGCCCA | 60 |
| GCGGAGCCTG | AGCAAGGAGC | GGGTCCGTCG | CGGAGCCGGA | GGGCGGGAGG | AAC ATG | 116 |
| | | | | | Met | |
| | | | | | 1 | |

| | | | | | | | | | | | | | | | |
|---|---|---|---|---|---|---|---|---|---|---|---|---|---|---|---|
| ACA | TCG | CGG | AGA | TGG | TTT | CAC | CCA | AAT | ATC | ACT | GGT | GTG | GAG | GCA | GAA | 164 |
| Thr | Ser | Arg | Arg | Trp | Phe | His | Pro | Asn | Ile | Thr | Gly | Val | Glu | Ala | Glu | |
| | | | 5 | | | | | 10 | | | | | 15 | | | |
| AAC | CTA | CTG | TTG | ACA | AGA | GGA | GTT | GAT | GGC | AGT | TTT | TTG | GCA | AGG | CCT | 212 |
| Asn | Leu | Leu | Leu | Thr | Arg | Gly | Val | Asp | Gly | Ser | Phe | Leu | Ala | Arg | Pro | |
| | | | 20 | | | | | 25 | | | | | 30 | | | |
| AGT | AAA | AGT | AAC | CCT | GGA | GAC | TTC | ACA | CTT | TCC | GTT | AGA | AGA | AAT | GGA | 260 |

|     |     |     |     |     |     |     |     |     |     |     |     |     |     |     |     |
|---|---|---|---|---|---|---|---|---|---|---|---|---|---|---|---|
| Ser | Lys | Ser | Asn | Pro | Gly | Asp | Phe | Thr | Leu | Ser | Val | Arg | Arg | Asn | Gly |
|     | 35  |     |     |     | 40  |     |     |     |     | 45  |     |     |     |     |     |

| GCT | GTC | ACC | CAC | ATC | AAG | ATT | CAG | AAC | ACT | GGT | GAT | TAC | TAT | GAC | CTG | 308 |
|---|---|---|---|---|---|---|---|---|---|---|---|---|---|---|---|---|
| Ala | Val | Thr | His | Ile | Lys | Ile | Gln | Asn | Thr | Gly | Asp | Tyr | Tyr | Asp | Leu |  |
| 50  |     |     |     |     | 55  |     |     |     |     | 60  |     |     |     |     | 65  |  |

| TAT | GGA | GGG | GAG | AAA | TTT | GCC | ACT | TTG | GCT | GAG | TTG | GTC | CAG | TAT | TAC | 356 |
|---|---|---|---|---|---|---|---|---|---|---|---|---|---|---|---|---|
| Tyr | Gly | Gly | Glu | Lys | Phe | Ala | Thr | Leu | Ala | Glu | Leu | Val | Gln | Tyr | Tyr |  |
|     |     |     |     | 70  |     |     |     |     | 75  |     |     |     |     | 80  |     |  |

| ATG | GAA | CAT | CAC | GGG | CAA | TTA | AAA | GAG | AAG | AAT | GGA | GAT | GTC | ATT | GAG | 404 |
|---|---|---|---|---|---|---|---|---|---|---|---|---|---|---|---|---|
| Met | Glu | His | His | Gly | Gln | Leu | Lys | Glu | Lys | Asn | Gly | Asp | Val | Ile | Glu |  |
|     |     |     | 85  |     |     |     |     | 90  |     |     |     |     | 95  |     |     |  |

| CTT | AAA | TAT | CCT | CTG | AAC | TGT | GCA | GAT | CCT | ACC | TCT | GAA | AGG | TGG | TTT | 452 |
|---|---|---|---|---|---|---|---|---|---|---|---|---|---|---|---|---|
| Leu | Lys | Tyr | Pro | Leu | Asn | Cys | Ala | Asp | Pro | Thr | Ser | Glu | Arg | Trp | Phe |  |
|     | 100 |     |     |     |     | 105 |     |     |     |     | 110 |     |     |     |     |  |

| CAT | GGA | CAT | CTC | TCT | GGG | AAA | GAA | GCA | GAG | AAA | TTA | TTA | ACT | GAA | AAA | 500 |
|---|---|---|---|---|---|---|---|---|---|---|---|---|---|---|---|---|
| His | Gly | His | Leu | Ser | Gly | Lys | Glu | Ala | Glu | Lys | Leu | Leu | Thr | Glu | Lys |  |
| 115 |     |     |     |     | 120 |     |     |     |     | 125 |     |     |     |     |     |  |

| GGA | AAA | CAT | GGT | AGT | TTT | CTT | GTA | CGA | GAG | AGC | CAG | AGC | CAC | CCT | GGA | 548 |
|---|---|---|---|---|---|---|---|---|---|---|---|---|---|---|---|---|
| Gly | Lys | His | Gly | Ser | Phe | Leu | Val | Arg | Glu | Ser | Gln | Ser | His | Pro | Gly |  |
| 130 |     |     |     |     | 135 |     |     |     |     | 140 |     |     |     |     | 145 |  |

| GAT | TTT | GTT | CTT | TCT | GTG | CGC | ACT | GGT | GAT | GAC | AAA | GGG | GAG | AGC | AAT | 596 |
|---|---|---|---|---|---|---|---|---|---|---|---|---|---|---|---|---|
| Asp | Phe | Val | Leu | Ser | Val | Arg | Thr | Gly | Asp | Asp | Lys | Gly | Glu | Ser | Asn |  |
|     |     |     |     | 150 |     |     |     |     | 155 |     |     |     |     | 160 |     |  |

| GAC | GGC | AAG | TCT | AAA | GTG | ACC | CAT | GTT | ATG | ATT | CGC | TGT | CAG | GAA | CTG | 644 |
|---|---|---|---|---|---|---|---|---|---|---|---|---|---|---|---|---|
| Asp | Gly | Lys | Ser | Lys | Val | Thr | His | Val | Met | Ile | Arg | Cys | Gln | Glu | Leu |  |
|     |     |     | 165 |     |     |     |     | 170 |     |     |     |     | 175 |     |     |  |

| AAA | TAC | GAC | GTT | GGT | GGA | GGA | GAA | CGG | TTT | GAT | TCT | TTG | ACA | GAT | CTT | 692 |
|---|---|---|---|---|---|---|---|---|---|---|---|---|---|---|---|---|
| Lys | Tyr | Asp | Val | Gly | Gly | Gly | Glu | Arg | Phe | Asp | Ser | Leu | Thr | Asp | Leu |  |
|     |     |     | 180 |     |     |     |     | 185 |     |     |     |     | 190 |     |     |  |

| GTG | GAA | CAT | TAT | AAG | AAG | AAT | CCT | ATG | GTG | GAA | ACA | TTG | GGT | ACA | GTA | 740 |
|---|---|---|---|---|---|---|---|---|---|---|---|---|---|---|---|---|
| Val | Glu | His | Tyr | Lys | Lys | Asn | Pro | Met | Val | Glu | Thr | Leu | Gly | Thr | Val |  |
|     | 195 |     |     |     |     | 200 |     |     |     |     | 205 |     |     |     |     |  |

| CTA | CAA | CTC | AAG | CAG | CCC | CTT | AAC | ACG | ACT | CGT | ATA | AAT | GCT | GCT | GAA | 788 |
|---|---|---|---|---|---|---|---|---|---|---|---|---|---|---|---|---|
| Leu | Gln | Leu | Lys | Gln | Pro | Leu | Asn | Thr | Thr | Arg | Ile | Asn | Ala | Ala | Glu |  |
| 210 |     |     |     |     | 215 |     |     |     |     | 220 |     |     |     |     | 225 |  |

| ATA | GAA | AGC | AGA | GTT | CGA | GAA | CTA | AGC | AAA | TTA | GCT | GAG | ACC | ACA | GAT | 836 |
|---|---|---|---|---|---|---|---|---|---|---|---|---|---|---|---|---|
| Ile | Glu | Ser | Arg | Val | Arg | Glu | Leu | Ser | Lys | Leu | Ala | Glu | Thr | Thr | Asp |  |
|     |     |     |     | 230 |     |     |     |     | 235 |     |     |     |     | 240 |     |  |

| AAA | GTC | AAA | CAA | GGC | TTT | TGG | GAA | GAA | TTT | GAG | ACA | CTA | CAA | CAA | CAG | 884 |
|---|---|---|---|---|---|---|---|---|---|---|---|---|---|---|---|---|
| Lys | Val | Lys | Gln | Gly | Phe | Trp | Glu | Glu | Phe | Glu | Thr | Leu | Gln | Gln | Gln |  |
|     |     |     | 245 |     |     |     |     | 250 |     |     |     |     | 255 |     |     |  |

| GAG | TGC | AAA | CTT | CTC | TAC | AGC | CGA | AAA | GAG | GGT | CAA | AGG | CAA | GAA | AAC | 932 |
|---|---|---|---|---|---|---|---|---|---|---|---|---|---|---|---|---|
| Glu | Cys | Lys | Leu | Leu | Tyr | Ser | Arg | Lys | Glu | Gly | Gln | Arg | Gln | Glu | Asn |  |
|     |     | 260 |     |     |     |     | 265 |     |     |     |     | 270 |     |     |     |  |

| AAA | AAC | AAA | AAT | AGA | TAT | AAA | AAC | ATC | CTG | CCC | TTT | GAT | CAT | ACC | AGG | 980 |
|---|---|---|---|---|---|---|---|---|---|---|---|---|---|---|---|---|
| Lys | Asn | Lys | Asn | Arg | Tyr | Lys | Asn | Ile | Leu | Pro | Phe | Asp | His | Thr | Arg |  |
|     | 275 |     |     |     |     | 280 |     |     |     |     | 285 |     |     |     |     |  |

| GTT | GTC | CTA | CAC | GAT | GGT | GAT | CCC | AAT | GAG | CCT | GTT | TCA | GAT | TAC | ATC | 1028 |
|---|---|---|---|---|---|---|---|---|---|---|---|---|---|---|---|---|
| Val | Val | Leu | His | Asp | Gly | Asp | Pro | Asn | Glu | Pro | Val | Ser | Asp | Tyr | Ile |  |
| 290 |     |     |     |     | 295 |     |     |     |     | 300 |     |     |     |     | 305 |  |

| AAT | GCA | AAT | ATC | ATC | ATG | CCT | GAA | TTT | GAA | ACC | AAG | TGC | AAC | AAT | TCA | 1076 |
|---|---|---|---|---|---|---|---|---|---|---|---|---|---|---|---|---|
| Asn | Ala | Asn | Ile | Ile | Met | Pro | Glu | Phe | Glu | Thr | Lys | Cys | Asn | Asn | Ser |  |
|     |     |     |     | 310 |     |     |     |     | 315 |     |     |     |     | 320 |     |  |

| AAG | CCC | AAA | AAG | AGT | TAC | ATT | GCC | ACA | CAA | GGC | TGC | CTG | CAA | AAC | ACG | 1124 |
|---|---|---|---|---|---|---|---|---|---|---|---|---|---|---|---|---|
| Lys | Pro | Lys | Lys | Ser | Tyr | Ile | Ala | Thr | Gln | Gly | Cys | Leu | Gln | Asn | Thr |  |
|     |     |     |     | 325 |     |     |     |     | 330 |     |     |     |     | 335 |     |  |

| GTG | AAT | GAC | TTT | TGG | CGG | ATG | GTG | TTC | CAA | GAA | AAC | TCC | CGA | GTG | ATT | 1172 |
|---|---|---|---|---|---|---|---|---|---|---|---|---|---|---|---|---|
| Val | Asn | Asp | Phe | Trp | Arg | Met | Val | Phe | Gln | Glu | Asn | Ser | Arg | Val | Ile |  |
|     |     |     | 340 |     |     |     |     | 345 |     |     |     |     | 350 |     |     |  |

| GTC | ATG | ACA | ACG | AAA | GAA | GTG | GAG | AGA | GGA | AAG | AGT | AAA | TGT | GTC | AAA | 1220 |

| | | | | | | | | | | | | | | | | |
|---|---|---|---|---|---|---|---|---|---|---|---|---|---|---|---|---|
| Val | Met | Thr | Thr | Lys | Glu | Val | Glu | Arg | Gly | Lys | Ser | Lys | Cys | Val | Lys | |
| | 355 | | | | 360 | | | | | 365 | | | | | | |
| TAC | TGG | CCT | GAT | GAG | TAT | GCT | CTA | AAA | GAA | TAT | GGC | GTC | ATG | CGT | GTT | 1268 |
| Tyr | Trp | Pro | Asp | Glu | Tyr | Ala | Leu | Lys | Glu | Tyr | Gly | Val | Met | Arg | Val | |
| 370 | | | | | 375 | | | | | 380 | | | | | 385 | |
| AGG | AAC | GTC | AAA | GAA | AGC | GCC | GCT | CAT | GAC | TAT | ACG | CTA | AGA | GAA | CTT | 1316 |
| Arg | Asn | Val | Lys | Glu | Ser | Ala | Ala | His | Asp | Tyr | Thr | Leu | Arg | Glu | Leu | |
| | | | | 390 | | | | | 395 | | | | | 400 | | |
| AAA | CTT | TCA | AAG | GTT | GGA | CAA | GGG | AAT | ACG | GAG | AGA | ACG | GTC | TGG | CAA | 1364 |
| Lys | Leu | Ser | Lys | Val | Gly | Gln | Gly | Asn | Thr | Glu | Arg | Thr | Val | Trp | Gln | |
| | | | 405 | | | | | 410 | | | | | 415 | | | |
| TAC | CAC | TTT | CGG | ACC | TGG | CCG | GAC | CAC | GGC | GTG | CCC | AGC | GAC | CCT | GGG | 1412 |
| Tyr | His | Phe | Arg | Thr | Trp | Pro | Asp | His | Gly | Val | Pro | Ser | Asp | Pro | Gly | |
| | | 420 | | | | | 425 | | | | | 430 | | | | |
| GGC | GTG | CTG | GAC | TTC | CTG | GAG | GAG | GTG | CAC | CAT | AAG | CAG | GAG | AGC | ATC | 1460 |
| Gly | Val | Leu | Asp | Phe | Leu | Glu | Glu | Val | His | His | Lys | Gln | Glu | Ser | Ile | |
| | 435 | | | | | 440 | | | | | 445 | | | | | |
| ATG | GAT | GCA | GGG | CCG | GTC | GTG | GTG | CAC | TGC | AGT | GCT | GGA | ATT | GGC | CGG | 1508 |
| Met | Asp | Ala | Gly | Pro | Val | Val | Val | His | Cys | Ser | Ala | Gly | Ile | Gly | Arg | |
| 450 | | | | | 455 | | | | | 460 | | | | | 465 | |
| ACA | GGG | ACG | TTC | ATT | GTG | ATT | GAT | ATT | CTT | ATT | GAC | ATC | ATC | AGA | GAG | 1556 |
| Thr | Gly | Thr | Phe | Ile | Val | Ile | Asp | Ile | Leu | Ile | Asp | Ile | Ile | Arg | Glu | |
| | | | | 470 | | | | | 475 | | | | | 480 | | |
| AAA | GGT | GTT | GAC | TGC | GAT | ATT | GAC | GTT | CCC | AAA | ACC | ATC | CAG | ATG | GTG | 1604 |
| Lys | Gly | Val | Asp | Cys | Asp | Ile | Asp | Val | Pro | Lys | Thr | Ile | Gln | Met | Val | |
| | | | 485 | | | | | 490 | | | | | 495 | | | |
| CGG | TCT | CAG | AGG | TCA | GGG | ATG | GTC | CAG | ACA | GAA | GCA | CAG | TAC | CGA | TTT | 1652 |
| Arg | Ser | Gln | Arg | Ser | Gly | Met | Val | Gln | Thr | Glu | Ala | Gln | Tyr | Arg | Phe | |
| | | 500 | | | | | 505 | | | | | 510 | | | | |
| ATC | TAT | ATG | GCG | GTC | CAG | CAT | TAT | ATT | GAA | ACA | CTA | CAG | CGC | AGG | ATT | 1700 |
| Ile | Tyr | Met | Ala | Val | Gln | His | Tyr | Ile | Glu | Thr | Leu | Gln | Arg | Arg | Ile | |
| | 515 | | | | | 520 | | | | | 525 | | | | | |
| GAA | GAA | GAG | CAG | AAA | AGC | AAG | AGG | AAA | GGG | CAC | GAA | TAT | ACA | AAT | ATT | 1748 |
| Glu | Glu | Glu | Gln | Lys | Ser | Lys | Arg | Lys | Gly | His | Glu | Tyr | Thr | Asn | Ile | |
| 530 | | | | | 535 | | | | | 540 | | | | | 545 | |
| AAG | TAT | TCT | CTA | GCG | GAC | CAG | ACG | AGT | GGA | GAT | CAG | AGC | CCT | CTC | CCG | 1796 |
| Lys | Tyr | Ser | Leu | Ala | Asp | Gln | Thr | Ser | Gly | Asp | Gln | Ser | Pro | Leu | Pro | |
| | | | | 550 | | | | | 555 | | | | | 560 | | |
| CCT | TGT | ACT | CCA | ACG | CCA | CCC | TGT | GCA | GAA | ATG | AGA | GAA | GAC | AGT | GCT | 1844 |
| Pro | Cys | Thr | Pro | Thr | Pro | Pro | Cys | Ala | Glu | Met | Arg | Glu | Asp | Ser | Ala | |
| | | | 565 | | | | | 570 | | | | | 575 | | | |
| AGA | GTC | TAT | GAA | AAC | GTG | GGC | CTG | ATG | CAA | CAG | CAG | AAA | AGT | TTC | AGA | T | 1893 |
| Arg | Val | Tyr | Glu | Asn | Val | Gly | Leu | Met | Gln | Gln | Gln | Lys | Ser | Phe | Arg | |
| | | 580 | | | | | 585 | | | | | 590 | | | | |

```
GAGAAAACCT  GCCAAAACTT  CAGCACAGAA  ATAGATGTGG  ACTTTCACCC  TCTCCCTAAA   1953

AAGATCAAGA  ACAGACGCAA  GAAAGTTTAT  GTGAAGACAG  AATTTGGATT  TGGAAGGCTT   2013

GCAATGTGGT  TGACTACCTT  TTGATAAGCA  AAATTTGAAA  CCATTTAAAG  ACCACTGTAT   2073

TTTAACTCAA  CAATACCTGC  TTCCCAATTA  CTCATTTCCT  CAGATAAGAA  GAAATCATCT   2133

CTACAATGTA  GACAACATTA  TATTTTATAG  AATTTGTTTG  AAATTGAGGA  AGCAGTTAAA   2193

TTGTGCGCTG  TATTTTGCAG  ATTATGGGGA  TTCAAATTCT  AGTAATAGGC  TTTTTTATTT   2253

TTATTTTTAT  ACCCTTAACC  AGG                                              2276
```

( 2 ) INFORMATION FOR SEQ ID NO:12:

( i ) SEQUENCE CHARACTERISTICS:
        ( A ) LENGTH: 593 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| Met | Thr | Ser | Arg | Arg | Trp | Phe | His | Pro | Asn | Ile | Thr | Gly | Val | Glu | Ala |
| 1 | | | | 5 | | | | | 10 | | | | | 15 | |

| Glu | Asn | Leu | Leu | Leu | Thr | Arg | Gly | Val | Asp | Gly | Ser | Phe | Leu | Ala | Arg |
| | | | | 20 | | | | | 25 | | | | | 30 | |

| Pro | Ser | Lys | Ser | Asn | Pro | Gly | Asp | Phe | Thr | Leu | Ser | Val | Arg | Arg | Asn |
| | | | 35 | | | | | 40 | | | | | 45 | | |

| Gly | Ala | Val | Thr | His | Ile | Lys | Ile | Gln | Asn | Thr | Gly | Asp | Tyr | Tyr | Asp |
| | | | 50 | | | | 55 | | | | | 60 | | | |

| Leu | Tyr | Gly | Gly | Glu | Lys | Phe | Ala | Thr | Leu | Ala | Glu | Leu | Val | Gln | Tyr |
| 65 | | | | | 70 | | | | | 75 | | | | | 80 |

| Tyr | Met | Glu | His | His | Gly | Gln | Leu | Lys | Glu | Lys | Asn | Gly | Asp | Val | Ile |
| | | | | 85 | | | | | 90 | | | | | 95 | |

| Glu | Leu | Lys | Tyr | Pro | Leu | Asn | Cys | Ala | Asp | Pro | Thr | Ser | Glu | Arg | Trp |
| | | | | 100 | | | | | 105 | | | | | 110 | |

| Phe | His | Gly | His | Leu | Ser | Gly | Lys | Glu | Ala | Glu | Lys | Leu | Leu | Thr | Glu |
| | | | | 115 | | | | | 120 | | | | | 125 | |

| Lys | Gly | Lys | His | Gly | Ser | Phe | Leu | Val | Arg | Glu | Ser | Gln | Ser | His | Pro |
| | | 130 | | | | | 135 | | | | | 140 | | | |

| Gly | Asp | Phe | Val | Leu | Ser | Val | Arg | Thr | Gly | Asp | Asp | Lys | Gly | Glu | Ser |
| 145 | | | | | 150 | | | | | 155 | | | | | 160 |

| Asn | Asp | Gly | Lys | Ser | Lys | Val | Thr | His | Val | Met | Ile | Arg | Cys | Gln | Glu |
| | | | | 165 | | | | | 170 | | | | | 175 | |

| Leu | Lys | Tyr | Asp | Val | Gly | Gly | Gly | Glu | Arg | Phe | Asp | Ser | Leu | Thr | Asp |
| | | | 180 | | | | | 185 | | | | | 190 | | |

| Leu | Val | Glu | His | Tyr | Lys | Lys | Asn | Pro | Met | Val | Glu | Thr | Leu | Gly | Thr |
| | | | 195 | | | | | 200 | | | | | 205 | | |

| Val | Leu | Gln | Leu | Lys | Gln | Pro | Leu | Asn | Thr | Thr | Arg | Ile | Asn | Ala | Ala |
| | 210 | | | | | 215 | | | | | 220 | | | | |

| Glu | Ile | Glu | Ser | Arg | Val | Arg | Glu | Leu | Ser | Lys | Leu | Ala | Glu | Thr | Thr |
| 225 | | | | | 230 | | | | | 235 | | | | | 240 |

| Asp | Lys | Val | Lys | Gln | Gly | Phe | Trp | Glu | Glu | Phe | Glu | Thr | Leu | Gln | Gln |
| | | | | 245 | | | | | 250 | | | | | 255 | |

| Gln | Glu | Cys | Lys | Leu | Leu | Tyr | Ser | Arg | Lys | Glu | Gly | Gln | Arg | Gln | Glu |
| | | | 260 | | | | | 265 | | | | | 270 | | |

| Asn | Lys | Asn | Lys | Asn | Arg | Tyr | Lys | Asn | Ile | Leu | Pro | Phe | Asp | His | Thr |
| | | | 275 | | | | | 280 | | | | | 285 | | |

| Arg | Val | Val | Leu | His | Asp | Gly | Asp | Pro | Asn | Glu | Pro | Val | Ser | Asp | Tyr |
| | 290 | | | | | 295 | | | | | 300 | | | | |

| Ile | Asn | Ala | Asn | Ile | Ile | Met | Pro | Glu | Phe | Glu | Thr | Lys | Cys | Asn | Asn |
| 305 | | | | | 310 | | | | | 315 | | | | | 320 |

| Ser | Lys | Pro | Lys | Lys | Ser | Tyr | Ile | Ala | Thr | Gln | Gly | Cys | Leu | Gln | Asn |
| | | | | 325 | | | | | 330 | | | | | 335 | |

| Thr | Val | Asn | Asp | Phe | Trp | Arg | Met | Val | Phe | Gln | Glu | Asn | Ser | Arg | Val |
| | | | 340 | | | | | 345 | | | | | 350 | | |

| Ile | Val | Met | Thr | Thr | Lys | Glu | Val | Glu | Arg | Gly | Lys | Ser | Lys | Cys | Val |
| | | | 355 | | | | | 360 | | | | | 365 | | |

| Lys | Tyr | Trp | Pro | Asp | Glu | Tyr | Ala | Leu | Lys | Glu | Tyr | Gly | Val | Met | Arg |
| | | | 370 | | | | | 375 | | | | | 380 | | |

| Val | Arg | Asn | Val | Lys | Glu | Ser | Ala | Ala | His | Asp | Tyr | Thr | Leu | Arg | Glu |
| 385 | | | | | 390 | | | | | 395 | | | | | 400 |

| | | | | | | | | | | | | | |
|---|---|---|---|---|---|---|---|---|---|---|---|---|---|
| Leu | Lys | Leu | Ser | Lys<br>405 | Val | Gly | Gln | Gly | Asn<br>410 | Thr | Glu | Arg | Thr | Val<br>415 | Trp |
| Gln | Tyr | His | Phe<br>420 | Arg | Thr | Trp | Pro | Asp<br>425 | His | Gly | Val | Pro | Ser<br>430 | Asp | Pro |
| Gly | Gly | Val<br>435 | Leu | Asp | Phe | Leu | Glu<br>440 | Glu | Val | His | His | Lys<br>445 | Gln | Glu | Ser |
| Ile | Met<br>450 | Asp | Ala | Gly | Pro | Val<br>455 | Val | Val | His | Cys | Ser<br>460 | Ala | Gly | Ile | Gly |
| Arg<br>465 | Thr | Gly | Thr | Phe | Ile<br>470 | Val | Ile | Asp | Ile | Leu<br>475 | Ile | Asp | Ile | Ile | Arg<br>480 |
| Glu | Lys | Gly | Val | Asp<br>485 | Cys | Asp | Ile | Asp | Val<br>490 | Pro | Lys | Thr | Ile | Gln<br>495 | Met |
| Val | Arg | Ser | Gln<br>500 | Arg | Ser | Gly | Met | Val<br>505 | Gln | Thr | Glu | Ala | Gln<br>510 | Tyr | Arg |
| Phe | Ile | Tyr<br>515 | Met | Ala | Val | Gln | His<br>520 | Tyr | Ile | Glu | Thr | Leu<br>525 | Gln | Arg | Arg |
| Ile | Glu<br>530 | Glu | Glu | Gln | Lys | Ser<br>535 | Lys | Arg | Lys | Gly | His<br>540 | Glu | Tyr | Thr | Asn |
| Ile<br>545 | Lys | Tyr | Ser | Leu | Ala<br>550 | Asp | Gln | Thr | Ser | Gly<br>555 | Asp | Gln | Ser | Pro | Leu<br>560 |
| Pro | Pro | Cys | Thr | Pro<br>565 | Thr | Pro | Pro | Cys | Ala<br>570 | Glu | Met | Arg | Glu | Asp<br>575 | Ser |
| Ala | Arg | Val | Tyr | Glu<br>580 | Asn | Val | Gly | Leu<br>585 | Met | Gln | Gln | Gln | Lys<br>590 | Ser | Phe |
| Arg |

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

AARTGYSMNS ARTAYTGGCC 20

( 2 ) INFORMATION FOR SEQ ID NO:14:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

CCNAYNCCNG CNGARCARTG NAC 23

( 2 ) INFORMATION FOR SEQ ID NO:15:

( i ) SEQUENCE CHARACTERISTICS:
        ( A ) LENGTH: 97 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Lys Cys Val Lys Tyr Trp Pro Asp Glu Cys Ala Leu Lys Glu Tyr Gly
  1           5                    10                    15

Val Met Arg Val Arg Asn Val Arg Glu Ser Ala Ala His Asp Tyr Thr
             20              25                        30

Leu Arg Glu Val Lys Val Cys Lys Val Gly Gln Gly Asn Thr Glu Arg
         35              40                     45

Thr Val Trp Gln Tyr His Phe Arg Thr Trp Pro Asp His Gly Val Pro
     50              55                  60

Ser Asp Pro Gly Gly Val Leu Asp Leu Val Glu Val His His Lys
 65              70                  75                  80

Gln Glu Ser Ile Val Asp Ala Gly Pro Val Val His Cys Ser Ala
             85              90                      95

Gly
```

(2) INFORMATION FOR SEQ ID NO:16:

(i) SEQUENCE CHARACTERISTICS:
      (A) LENGTH: 97 amino acids
      (B) TYPE: amino acid
      (D) TOPOLOGY: linear (ii) MOLECULE TYPE: protein (xi) SEQUENCE DESCRIPTION: SEQ ID NO:16:

```
Lys Cys Val Lys Tyr Trp Pro Asp Glu Tyr Ala Leu Lys Glu Tyr Gly
  1           5                    10                    15

Val Met Arg Val Arg Asn Val Lys Glu Ser Ala Ala His Asp Tyr Thr
             20              25                        30

Leu Arg Glu Leu Lys Leu Ser Lys Val Gly Gln Gly Asn Thr Glu Arg
         35              40                     45

Thr Val Trp Gln Tyr His Phe Arg Thr Trp Pro Asp His Gly Val Pro
     50              55                  60

Ser Asp Pro Gly Gly Val Leu Asp Phe Leu Glu Glu Val His His Lys
 65              70                  75                  80

Gln Glu Ser Ile Met Asp Ala Gly Pro Val Val Val His Cys Ser Ala
             85              90                      95

Gly
```

(2) INFORMATION FOR SEQ ID NO:17:

(i) SEQUENCE CHARACTERISTICS:
      (A) LENGTH: 99 amino acids
      (B) TYPE: amino acid
      (D) TOPOLOGY: linear (ii) MOLECULE TYPE: protein (xi) SEQUENCE DESCRIPTION: SEQ ID NO:17:

```
Lys Cys Ala Arg Tyr Trp Pro Asp Glu Gly Arg Ser Glu Gln Phe Gly
  1           5                    10                    15

His Ala Arg Ile Gln Cys Val Ser Glu Asn Ser Thr Ser Asp Tyr Thr
             20              25                        30

Leu Arg Glu Phe Leu Val Ser Trp Arg Asp Gln Pro Ala Arg Arg Ile
         35              40                     45

Phe His Tyr His Phe Gln Val Trp Pro Asp His Gly Val Pro Ala Asp
     50              55                  60

Pro Gly Cys Val Leu Asn Phe Leu Gln Asp Val Asn Thr Arg Gln Ser
 65              70                  75                      80

His Leu Ala Gln Ala Gly Glu Lys Pro Gly Pro Ile Cys Val His Cys
```

Ser Ala Gly ( 2 ) INFORMATION FOR SEQ ID NO:18:

( i ) SEQUENCE CHARACTERISTICS:
      ( A ) LENGTH: 97 amino acids
      ( B ) TYPE: amino acid
      ( D ) TOPOLOGY: linear ( i i ) MOLECULE TYPE: protein ( x i ) SEQUENCE DESCRIPTION: SEQ ID NO:18:

```
Lys Cys Val Pro Tyr Trp Pro Glu Val Gly Met Gln Arg Ala Tyr Gly
  1               5                  10                  15
Pro Tyr Ser Val Thr Asn Cys Gly Glu His Asp Thr Thr Glu Tyr Lys
             20                  25                  30
Leu Arg Thr Leu Gln Val Ser Pro Leu Asp Asn Gly Asp Leu Ile Arg
         35                  40                  45
Glu Ile Trp His Tyr Gln Tyr Leu Ser Trp Pro Asp His Gly Val Pro
     50                  55                  60
Ser Glu Pro Gly Gly Val Leu Ser Phe Leu Asp Gln Ile Asn Gln Arg
 65                  70                  75                  80
Gln Glu Ser Leu Pro His Ala Gly Pro Ile Ile Val His Cys Ser Ala
                 85                  90                  95
Gly
```

( 2 ) INFORMATION FOR SEQ ID NO:19:

( i ) SEQUENCE CHARACTERISTICS:
      ( A ) LENGTH: 99 amino acids
      ( B ) TYPE: amino acid
      ( D ) TOPOLOGY: linear ( i i ) MOLECULE TYPE: protein ( x i ) SEQUENCE DESCRIPTION: SEQ ID NO:19:

```
Leu Cys Pro Gln Tyr Trp Pro Glu Asn Gly Val His Arg His Gly Pro
  1               5                  10                  15
Ile Gln Val Glu Phe Val Ser Ala Asp Leu Glu Glu Asp Ile Ile Ser
             20                  25                  30
Arg Ile Phe Arg Ile Tyr Asn Ala Ala Arg Pro Gln Asp Gly Tyr Arg
         35                  40                  45
Met Val Gln Gln Phe Gln Phe Leu Gly Trp Pro Met Tyr Arg Asp Thr
     50                  55                  60
Pro Val Ser Lys Arg Ser Phe Leu Lys Leu Ile Arg Gln Val Asp Lys
 65                  70                  75                  80
Trp Gln Glu Glu Tyr Asn Gly Gly Glu Gly Pro Thr Val Val His Cys
                 85                  90                  95
Leu Asn Gly
```

( 2 ) INFORMATION FOR SEQ ID NO:20:

( i ) SEQUENCE CHARACTERISTICS:
      ( A ) LENGTH: 97 amino acids
      ( B ) TYPE: amino acid
      ( D ) TOPOLOGY: linear ( i i ) MOLECULE TYPE: protein ( x i ) SEQUENCE DESCRIPTION: SEQ ID NO:20:

```
Lys  Cys  Asp  His  Tyr  Trp  Pro  Ala  Asp  Gln  Asp  Ser  Leu  Tyr  Tyr  Gly
 1              5                        10                       15

Asp  Leu  Ile  Leu  Gln  Met  Leu  Ser  Glu  Ser  Val  Leu  Pro  Glu  Trp  Thr
               20                   25                       30

Ile  Arg  Glu  Phe  Lys  Ile  Cys  Gly  Glu  Gln  Leu  Asp  Ala  His  Arg
          35                        40                  45

Leu  Ile  Arg  His  Phe  His  Tyr  Thr  Val  Trp  Pro  Asp  His  Gly  Val  Pro
          50                        55                       60

Glu  Thr  Thr  Gln  Ser  Leu  Ile  Gln  Phe  Val  Arg  Thr  Val  Arg  Asp  Tyr
 65                       70                        75                       80

Ile  Asn  Arg  Ser  Pro  Gly  Ala  Gly  Pro  Thr  Val  Val  His  Cys  Ser  Ala
                    85                        90                       95

Gly
```

(2) INFORMATION FOR SEQ ID NO:21:

(i) SEQUENCE CHARACTERISTICS:
    (A) LENGTH: 95 amino acids
    (B) TYPE: amino acid
    (D) TOPOLOGY: linear (ii) MOLECULE TYPE: protein (xi) SEQUENCE DESCRIPTION: SEQ ID NO:21:

```
Lys  Cys  His  Gln  Tyr  Trp  Pro  Ala  Glu  Arg  Ser  Ala  Arg  Tyr  Gln  Tyr
 1              5                        10                       15

Phe  Val  Val  Asp  Pro  Met  Ala  Glu  Tyr  Asn  Met  Pro  Gln  Tyr  Ile  Leu
               20                   25                       30

Arg  Glu  Phe  Lys  Val  Thr  Asp  Ala  Arg  Asp  Gly  Gln  Ser  Arg  Thr  Ile
          35                        40                  45

Arg  Gln  Phe  Gln  Phe  Thr  Asp  Trp  Pro  Glu  Gln  Gly  Val  Pro  Lys  Thr
          50                        55                       60

Gly  Glu  Gly  Phe  Ile  Asp  Phe  Ile  Gly  Gln  Val  His  Lys  Thr  Lys  Glu
 65                       70                        75                       80

Gln  Phe  Gly  Gln  Asp  Gly  Pro  Ile  Thr  Val  His  Cys  Ser  Ala  Gly
                    85                        90                       95
```

(2) INFORMATION FOR SEQ ID NO:22:

(i) SEQUENCE CHARACTERISTICS:
    (A) LENGTH: 95 amino acids
    (B) TYPE: amino acid
    (D) TOPOLOGY: linear (ii) MOLECULE TYPE: protein (xi) SEQUENCE DESCRIPTION: SEQ ID NO:22:

```
Lys  Cys  His  Gln  Tyr  Trp  Pro  Ala  Glu  Arg  Ser  Ala  Arg  Tyr  Gln  Tyr
 1              5                        10                       15

Phe  Val  Val  Asp  Pro  Met  Ala  Glu  Tyr  Asn  Met  Pro  Gln  Tyr  Ile  Leu
               20                   25                       30

Arg  Glu  Phe  Lys  Val  Thr  Asp  Ala  Arg  Asp  Gly  Gln  Ser  Arg  Thr  Val
          35                        40                  45

Arg  Gln  Phe  Gln  Phe  Thr  Asp  Trp  Pro  Glu  Gln  Gly  Val  Pro  Lys  Ser
          50                        55                       60

Gly  Glu  Gly  Phe  Ile  Asp  Phe  Ile  Gly  Gln  Val  His  Lys  Thr  Lys  Glu
 65                       70                        75                       80

Gln  Phe  Gly  Gln  Asp  Gly  Pro  Ile  Ser  Val  His  Cys  Ser  Ala  Gly
                    85                        90                       95
```

( 2 ) INFORMATION FOR SEQ ID NO:23:

( i ) SEQUENCE CHARACTERISTICS:
        ( A ) LENGTH: 95 amino acids
        ( B ) TYPE: amino acid
        ( D ) TOPOLOGY: linear ( i i ) MOLECULE TYPE: protein ( x i ) SEQUENCE DESCRIPTION: SEQ ID NO:23:

```
Lys Cys Phe Gln Tyr Trp Pro His Glu Arg Ser Val Arg Tyr Gln Tyr
 1               5                  10                  15
Tyr Val Val Asp Pro Ile Ala Glu Tyr Asn Met Pro Gln Tyr Lys Leu
             20                  25                  30
Arg Glu Phe Lys Val Thr Asp Ala Arg Asp Gly Ser Ser Arg Thr Val
         35                  40                  45
Arg Gln Phe Gln Phe Ile Asp Trp Pro Glu Gln Gly Val Pro Lys Ser
     50                  55                  60
Gly Glu Gly Phe Ile Asp Phe Ile Gly Gln Val His Lys Thr Lys Glu
 65                  70                  75                  80
Gln Phe Gly Gln Asp Gly Pro Ile Thr Val His Cys Ser Ala Gly
                 85                  90                  95
```

( 2 ) INFORMATION FOR SEQ ID NO:24:

( i ) SEQUENCE CHARACTERISTICS:
        ( A ) LENGTH: 100 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

```
Trp Phe His Pro Asn Ile Thr Gly Val Glu Ala Glu Asn Leu Leu Leu
 1               5                  10                  15
Thr Arg Gly Val Asp Gly Ser Phe Leu Ala Arg Pro Ser Lys Ser Asn
             20                  25                  30
Pro Gly Asp Phe Thr Leu Ser Val Arg Arg Asn Gly Ala Val Thr His
         35                  40                  45
Ile Lys Ile Gln Asn Thr Gly Asp Tyr Tyr Asp Leu Tyr Gly Gly Glu
     50                  55                  60
Lys Phe Ala Thr Leu Ala Glu Leu Val Gln Tyr Tyr Met Glu His His
 65                  70                  75                  80
Gly Gln Leu Lys Glu Lys Asn Gly Asp Val Ile Glu Leu Lys Tyr Pro
                 85                  90                  95
Leu Asn Cys Ala
         100
```

( 2 ) INFORMATION FOR SEQ ID NO:25:

( i ) SEQUENCE CHARACTERISTICS:
        ( A ) LENGTH: 99 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

```
Trp Phe His Pro Thr Ile Ser Gly Ile Glu Ala Glu Lys Leu Leu Gln
 1               5                  10                  15
Glu Gln Gly Phe Asp Gly Ser Phe Leu Ala Arg Leu Ser Ser Ser Asn
             20                  25                  30
```

```
Pro Gly Ala Phe Thr Leu Ser Val Arg Arg Gly Asn Glu Val Thr His
        35                  40                  45
Ile Lys Ile Gln Asn Asn Gly Asp Phe Phe Asp Leu Tyr Gly Gly Glu
    50                  55                  60
Lys Phe Ala Thr Leu Pro Glu Leu Val Gln Tyr Tyr Met Glu Asn Gly
65                  70                  75                      80
Glu Leu Lys Glu Lys Asn Gly Gln Ala Ile Glu Leu Lys Gln Pro Leu
                85                  90                  95
Ile Cys Ala
```

( 2 ) INFORMATION FOR SEQ ID NO:26:

( i ) SEQUENCE CHARACTERISTICS:
        ( A ) LENGTH: 100 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Trp Phe His Arg Asp Leu Ser Gly Leu Asp Ala Glu Thr Leu Leu Lys
1                   5                   10                  15
Gly Arg Gly Val His Gly Ser Phe Leu Ala Arg Pro Ser Arg Lys Asn
                20                  25                  30
Gln Gly Asp Phe Ser Leu Ser Val Arg Val Gly Asp Gln Val Thr His
        35                  40                  45
Ile Arg Ile Gln Asn Ser Gly Asp Phe Tyr Asp Leu Tyr Gly Gly Glu
    50                  55                  60
Lys Phe Ala Thr Leu Thr Glu Leu Val Glu Tyr Tyr Thr Gln Gln Gln
65                  70                  75                      80
Gly Val Val Gln Asp Arg Asp Gly Thr Ile Ile His Leu Lys Tyr Pro
                85                  90                  95
Leu Asn Cys Ser
            100
```

( 2 ) INFORMATION FOR SEQ ID NO:27:

( i ) SEQUENCE CHARACTERISTICS:
        ( A ) LENGTH: 102 amino acids
        ( B ) TYPE: amino acid
        ( D ) TOPOLOGY: linear ( i i ) MOLECULE TYPE: protein ( x i ) SEQUENCE DESCRIPTION: SEQ ID NO:27:

```
Trp Phe His Gly His Leu Ser Gly Lys Glu Ala Glu Lys Leu Leu Thr
1                   5                   10                  15
Glu Lys Gly Lys His Gly Ser Phe Leu Val Arg Glu Ser Gln Ser His
                20                  25                  30
Pro Gly Asp Phe Val Leu Ser Val Arg Thr Gly Asp Asp Lys Gly Glu
        35                  40                  45
Ser Asn Asp Gly Lys Ser Lys Val Thr His Val Met Ile Arg Cys Gln
    50                  55                  60
Glu Leu Lys Tyr Asp Val Gly Gly Gly Glu Arg Phe Asp Ser Leu Thr
65                  70                  75                      80
Asp Leu Val Glu His Tyr Lys Lys Asn Pro Met Val Glu Thr Leu Gly
                85                  90                  95
Thr Val Leu Gln Leu Lys
            100
```

( 2 ) INFORMATION FOR SEQ ID NO:28:

( i ) SEQUENCE CHARACTERISTICS:
        ( A ) LENGTH: 92 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

```
Trp Phe His Gly Asn Leu Ser Gly Lys Glu Ala Glu Lys Leu Ile Leu
 1               5                  10                 15
Glu Arg Gly Lys Asn Gly Ser Phe Leu Val Arg Glu Ser Gln Ser Lys
            20                  25                 30
Pro Gly Asp Phe Val Leu Ser Val Arg Thr Asp Asp Lys Val Thr His
        35                  40                 45
Val Met Ile Arg Trp Gln Asp Lys Lys Tyr Asp Val Gly Gly Gly Glu
    50                  55                 60
Ser Phe Gly Thr Leu Ser Glu Leu Ile Asp His Tyr Lys Arg Asn Pro
65                  70                  75                 80
Met Val Glu Thr Cys Gly Thr Val Val His Leu Arg
                85                  90
```

( 2 ) INFORMATION FOR SEQ ID NO:29:

( i ) SEQUENCE CHARACTERISTICS:
        ( A ) LENGTH: 100 amino acids
        ( B ) TYPE: amino acid
        ( D ) TOPOLOGY: linear ( i i ) MOLECULE TYPE: protein ( x i ) SEQUENCE DESCRIPTION: SEQ ID NO:29:

```
Trp Tyr His Gly His Met Ser Gly Gly Gln Ala Glu Thr Leu Leu Gln
 1               5                  10                 15
Ala Lys Gly Glu Pro Trp Thr Phe Leu Val Arg Glu Ser Leu Ser Gln
            20                  25                 30
Pro Gly Asp Phe Val Leu Ser Val Leu Ser Asp Gln Pro Lys Ala Gly
        35                  40                 45
Pro Gly Ser Pro Leu Arg Val Thr His Ile Lys Val Met Cys Glu Gly
        50                  55                 60
Gly Arg Tyr Thr Val Gly Gly Leu Glu Thr Phe Asp Ser Leu Thr Asp
65                  70                  75                 80
Leu Val Glu His Phe Lys Lys Thr Gly Ile Glu Glu Ala Ser Gly Ala
                85                  90                 95
Phe Val Tyr Leu
            100
```

( 2 ) INFORMATION FOR SEQ ID NO:30:

( i ) SEQUENCE CHARACTERISTICS:
        ( A ) LENGTH: 96 amino acids
        ( B ) TYPE: amino acid
        ( D ) TOPOLOGY: linear ( i i ) MOLECULE TYPE: protein ( x i ) SEQUENCE DESCRIPTION: SEQ ID NO:30:

```
Trp Tyr His Gly Ala Ile Pro Arg Ile Glu Ala Gln Glu Leu Leu Lys
 1               5                  10                 15
Lys Gln Gly Asp Phe Leu Val Arg Glu Ser His Gly Lys Pro Gly Glu
```

|   |   |   |   |   | 20  |   |   |   |   | 25  |   |   |   |   | 30  |   |   |
|---|---|---|---|---|-----|---|---|---|---|-----|---|---|---|---|-----|---|---|

```
Tyr Val Leu Ser Val Tyr Ser Asp Gly Gln Arg Arg His Phe Ile Ile
             35                  40                  45

Gln Tyr Val Asp Asn Met Tyr Arg Phe Glu Gly Thr Gly Phe Ser Asn
 50                  55                  60

Ile Pro Gln Leu Ile Asp His His Tyr Thr Thr Lys Gln Val Ile Thr
 65              70                  75                       80

Lys Lys Ser Gly Val Val Leu Leu Asn Pro Ile Pro Lys Asp Lys Lys
                 85                  90                       95
```

(2) INFORMATION FOR SEQ ID NO:31:

(i) SEQUENCE CHARACTERISTICS:
        (A) LENGTH: 100 amino acids
        (B) TYPE: amino acid
        (D) TOPOLOGY: linear (ii) MOLECULE TYPE: protein (xi) SEQUENCE DESCRIPTION: SEQ ID NO:31:

```
Trp Phe His Gly Lys Ile Ser Lys Gln Glu Ala Tyr Asn Leu Leu Met
 1               5                  10                  15

Thr Val Gly Gln Ala Cys Ser Phe Leu Val Arg Pro Ser Asp Asn Thr
                 20                  25                  30

Pro Gly Asp Tyr Ser Leu Tyr Phe Arg Thr Ser Glu Asn Ile Gln Arg
             35                  40                  45

Phe Lys Ile Cys Pro Thr Pro Asn Asn Gln Phe Met Met Gly Gly Arg
 50                  55                  60

Tyr Tyr Asn Ser Ile Gly Asp Ile Ile Asp His Tyr Arg Lys Glu Gln
 65              70                  75                       80

Ile Val Glu Gly Tyr Tyr Leu Lys Glu Pro Val Pro Met Gln Asp Gln
                 85                  90                       95

Glu Gln Val Leu
            100
```

(2) INFORMATION FOR SEQ ID NO:32:

(i) SEQUENCE CHARACTERISTICS:
        (A) LENGTH: 107 amino acids
        (B) TYPE: amino acid
        (D) TOPOLOGY: linear (ii) MOLECULE TYPE: protein (xi) SEQUENCE DESCRIPTION: SEQ ID NO:32:

```
Trp Tyr Phe Gly Lys Ile Ser Arg Lys Asp Ala Glu Arg Gln Leu Leu
 1               5                  10                  15

Ser Ser Gly Asn Pro Gln Gly Ala Phe Leu Ile Arg Glu Ser Glu Thr
                 20                  25                  30

Thr Lys Gly Ala Tyr Ser Leu Ser Ile Arg Asp Trp Asp Gln Asn Arg
             35                  40                  45

Gly Asp His Ile Lys His Tyr Lys Ile Arg Lys Leu Asp Thr Gly Gly
         50                  55                  60

Tyr Tyr Ile Thr Thr Arg Ala Gln Phe Asp Ser Ile Gln Asp Leu Val
 65                  70                  75                   80

Gln His Tyr Met Glu Val Asn Asp Gly Leu Cys Tyr Leu Leu Thr Ala
                 85                  90                       95

Pro Cys Thr Thr Thr Lys Pro Gln Thr Leu Gly
             100                 105
```

( 2 ) INFORMATION FOR SEQ ID NO:33:

( i ) SEQUENCE CHARACTERISTICS:
        ( A ) LENGTH: 96 amino acids
        ( B ) TYPE: amino acid
        ( D ) TOPOLOGY: linear ( i i ) MOLECULE TYPE: protein ( x i ) SEQUENCE DESCRIPTION: SEQ ID NO:33:

```
Trp Tyr Tyr Gly Lys Val Thr Arg His Gln Ala Glu Met Ala Leu Asn
 1               5                  10                  15
Glu Arg Gly His Glu Gly Asp Phe Leu Ile Arg Asp Ser Glu Ser Ser
             20                  25                  30
Pro Asn Asp Phe Ser Val Ser Leu Lys Ala Gln Gly Lys Asn Lys His
         35                  40                  45
Phe Lys Val Gln Leu Lys Glu Thr Val Tyr Cys Ile Gly Gln Arg Lys
     50                  55                  60
Phe Ser Thr Met Glu Glu Leu Val Glu His Tyr Lys Lys Ala Pro Ile
 65                  70                  75                  80
Phe Thr Ser Glu Gln Gly Glu Lys Leu Tyr Leu Val Lys His Leu Ser
                 85                  90                  95
```

( 2 ) INFORMATION FOR SEQ ID NO:34:

( i ) SEQUENCE CHARACTERISTICS:
        ( A ) LENGTH: 102 amino acids
        ( B ) TYPE: amino acid
        ( D ) TOPOLOGY: linear ( i i ) MOLECULE TYPE: protein ( x i ) SEQUENCE DESCRIPTION: SEQ ID NO:34:

```
Trp Tyr Phe Gly Asp Val Lys Arg Ala Lys Ala Glu Lys Arg Leu Met
 1               5                  10                  15
Val Arg Gly Leu Pro Ser Gly Thr Phe Leu Ile Arg Lys Ala Glu Thr
             20                  25                  30
Ala Val Gly Asn Phe Ser Leu Ser Val Arg Asp Gly Asp Ser Val Lys
         35                  40                  45
His Tyr Arg Val Arg Lys Leu Asp Thr Gly Gly Tyr Phe Ile Thr Thr
     50                  55                  60
Arg Ala Pro Phe Asn Ser Leu Tyr Glu Leu Val Gln His Tyr Thr Lys
 65                  70                  75                  80
Asp Ala Asp Gly Leu Val Cys Ala Leu Thr Leu Pro Cys Pro Lys Asp
                 85                  90                  95
Lys Pro Val Thr Gly Gly
             100
```

( 2 ) INFORMATION FOR SEQ ID NO:35:

( i ) SEQUENCE CHARACTERISTICS:
        ( A ) LENGTH: 99 amino acids
        ( B ) TYPE: amino acid
        ( D ) TOPOLOGY: linear ( i i ) MOLECULE TYPE: protein ( x i ) SEQUENCE DESCRIPTION: SEQ ID NO:35:

```
Trp Tyr Phe Gly Lys Ile Ser Arg Lys Asp Ala Glu Arg Gln Leu Leu
 1               5                  10                  15
Ser Ser Gly Asn Pro Gln Gly Ala Phe Leu Ile Arg Glu Ser Glu Thr
             20                  25                  30
```

```
Thr Lys Gly Ala Tyr Ser Leu Ser Ile Arg Asp Trp Asp Gln Asn Arg
        35                  40                  45
Gly Asp His Ile Lys His Tyr Lys Ile Arg Lys Leu Asp Thr Gly Gly
        50                  55                  60
Tyr Tyr Ile Thr Thr Arg Ala Gln Phe Asp Ser Ile Gln Asp Leu Val
65                   70                  75                  80
Gln His Tyr Met Glu Val Asn Asp Gly Leu Cys Tyr Leu Leu Thr Ala
                 85                  90                  95
Pro Cys Thr
```

( 2 ) INFORMATION FOR SEQ ID NO:36:

( i ) SEQUENCE CHARACTERISTICS:
        ( A ) LENGTH: 99 amino acids
        ( B ) TYPE: amino acid
        ( D ) TOPOLOGY: linear ( i i ) MOLECULE TYPE: protein ( x i ) SEQUENCE DESCRIPTION: SEQ ID NO:36:

```
Trp Tyr Phe Gly Lys Met Gly Arg Lys Asp Ala Glu Arg Leu Leu Leu
1               5                   10                  15
Asn Pro Gly Asn Gln Arg Gly Ile Phe Leu Val Arg Glu Ser Glu Thr
            20                  25                  30
Thr Lys Gly Ala Tyr Ser Leu Ser Ile Arg Asp Trp Asp Glu Val Arg
        35                  40                  45
Gly Asp Asn Val Lys His Tyr Lys Ile Arg Lys Leu Asp Asn Gly Gly
        50                  55                  60
Tyr Tyr Ile Thr Thr Arg Ala Gln Phe Glu Ser Leu Gln Lys Leu Val
65                   70                  75                  80
Lys His Tyr Arg Glu His Ala Asp Gly Leu Cys His Lys Leu Thr Thr
                 85                  90                  95
Val Cys Pro
```

( 2 ) INFORMATION FOR SEQ ID NO:37:

( i ) SEQUENCE CHARACTERISTICS:
        ( A ) LENGTH: 99 amino acids
        ( B ) TYPE: amino acid
        ( D ) TOPOLOGY: linear ( i i ) MOLECULE TYPE: protein ( x i ) SEQUENCE DESCRIPTION: SEQ ID NO:37:

```
Trp Tyr Phe Gly Lys Leu Gly Arg Lys Asp Ala Glu Arg Gln Leu Leu
1               5                   10                  15
Ser Phe Gly Asn Pro Arg Gly Thr Phe Leu Ile Arg Glu Ser Glu Thr
            20                  25                  30
Thr Lys Gly Ala Tyr Ser Leu Ser Ile Arg Asp Trp Asp Asp Met Lys
        35                  40                  45
Gly Asp His Val Lys His Tyr Lys Ile Arg Lys Leu Asp Asn Gly Gly
        50                  55                  60
Tyr Tyr Ile Thr Thr Arg Ala Gln Phe Glu Thr Leu Gln Gln Leu Val
65                   70                  75                  80
Gln His Tyr Ser Glu Arg Ala Ala Gly Leu Cys Cys Arg Leu Val Val
                 85                  90                  95
Pro Cys His
```

5,536,636

81
82
-continued ( 2 ) INFORMATION FOR SEQ ID NO:38:

( i ) SEQUENCE CHARACTERISTICS:
        ( A ) LENGTH: 99 amino acids
        ( B ) TYPE: amino acid
        ( D ) TOPOLOGY: linear ( i i ) MOLECULE TYPE: protein ( x i ) SEQUENCE DESCRIPTION: SEQ ID NO:38:

```
Trp  Phe  Phe  Lys  Asn  Leu  Ser  Arg  Lys  Asp  Ala  Glu  Arg  Gln  Leu  Leu
1               5                        10                            15

Ala  Pro  Gly  Asn  Thr  His  Gly  Ser  Phe  Leu  Ile  Arg  Glu  Ser  Glu  Ser
              20                        25                      30

Thr  Ala  Gly  Ser  Phe  Ser  Leu  Ser  Val  Arg  Asp  Phe  Asp  Gln  Asn  Gln
         35                       40                      45

Gly  Glu  Val  Val  Lys  His  Tyr  Lys  Ile  Arg  Asn  Leu  Asp  Asn  Gly  Gly
    50                       55                       60

Phe  Tyr  Ile  Ser  Pro  Arg  Ile  Thr  Phe  Pro  Gly  Leu  His  Asp  Leu  Val
65                      70                       75                          80

Arg  His  Tyr  Thr  Asn  Ala  Ser  Asp  Gly  Leu  Cys  Thr  Lys  Leu  Ser  Arg
               85                        90                           95

Pro  Cys  Gln
```

( 2 ) INFORMATION FOR SEQ ID NO:39:

( i ) SEQUENCE CHARACTERISTICS:
        ( A ) LENGTH: 98 amino acids
        ( B ) TYPE: amino acid
        ( D ) TOPOLOGY: linear ( i i ) MOLECULE TYPE: protein ( x i ) SEQUENCE DESCRIPTION: SEQ ID NO:39:

```
Trp  Phe  Phe  Arg  Thr  Ile  Ser  Arg  Lys  Asp  Ala  Glu  Arg  Gln  Leu  Leu
1               5                        10                            15

Ala  Pro  Met  Asn  Lys  Ala  Gly  Ser  Phe  Leu  Ile  Arg  Glu  Ser  Glu  Ser
              20                        25                      30

Asn  Lys  Gly  Ala  Phe  Ser  Leu  Ser  Val  Lys  Asp  Ile  Thr  Thr  Gln  Gly
         35                       40                      45

Glu  Val  Val  Lys  His  Tyr  Lys  Ile  Arg  Ser  Leu  Asp  Asn  Gly  Gly  Tyr
    50                       55                       60

Tyr  Ile  Ser  Pro  Arg  Ile  Thr  Phe  Pro  Thr  Leu  Gln  Ala  Leu  Val  Gln
65                      70                       75                          80

His  Tyr  Ser  Lys  Lys  Gly  Asp  Gly  Leu  Cys  Gln  Lys  Leu  Thr  Leu  Pro
               85                        90                           95

Cys  Val
```

( 2 ) INFORMATION FOR SEQ ID NO:40:

( i ) SEQUENCE CHARACTERISTICS:
        ( A ) LENGTH: 91 amino acids
        ( B ) TYPE: amino acid
        ( D ) TOPOLOGY: linear ( i i ) MOLECULE TYPE: protein ( x i ) SEQUENCE DESCRIPTION: SEQ ID NO:40:

```
Trp  Tyr  Tyr  Gly  Lys  Val  Thr  Arg  His  Gln  Ala  Glu  Met  Ala  Leu  Asn
1               5                        10                            15

Glu  Arg  Gly  His  Glu  Gly  Asp  Phe  Leu  Ile  Arg  Asp  Ser  Glu  Ser  Ser
              20                        25                      30
```

```
        Pro  Asn  Asp  Phe  Ser  Val  Ser  Leu  Lys  Ala  Gln  Gly  Lys  Asn  Lys  His
                  35                       40                      45

Phe  Lys  Val  Gln  Leu  Lys  Glu  Thr  Val  Tyr  Cys  Ile  Gly  Gln  Arg  Lys
                  50                       55                      60

Phe  Ser  Thr  Met  Glu  Glu  Leu  Val  Glu  His  Tyr  Lys  Lys  Ala  Pro  Ile
        65                       70                      75                      80

Phe  Thr  Ser  Glu  Gln  Gly  Glu  Lys  Leu  Tyr  Leu
                       85                      90
```

( 2 ) INFORMATION FOR SEQ ID NO:41:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

TCCACGGTAG CTTCCTGGCT C    21

( 2 ) INFORMATION FOR SEQ ID NO:42:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

AGTGGGATCG GAGCAGTTCA G    21

( 2 ) INFORMATION FOR SEQ ID NO:43:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:43:

CCATCATCCA CCTCAAGTAC CCG    23

( 2 ) INFORMATION FOR SEQ ID NO:44:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

CCACCCTCGC ACATGACCTT G    21

( 2 ) INFORMATION FOR SEQ ID NO:45:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:45:

CCGCTCAGGG TCACCCACAT C    21

( 2 ) INFORMATION FOR SEQ ID NO:46:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:46:

CTGTATCCTC GGACTCCTGC                                          20

( 2 ) INFORMATION FOR SEQ ID NO:47:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:47:

CGAGTGTTGG AACTGAACAA G                                        21

( 2 ) INFORMATION FOR SEQ ID NO:48:

( i ) SEQUENCE CHARACTERISTICS:
            ( A ) LENGTH: 22 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:48:

GATGTAGTTG GCATTGATGT AG                                       22

( 2 ) INFORMATION FOR SEQ ID NO:49:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:49:

GACGGGACAG TAACATCCCC G                                        21

( 2 ) INFORMATION FOR SEQ ID NO:50:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:50:

CCATAAGCAC GCTGCATGCC                                          20

( 2 ) INFORMATION FOR SEQ ID NO:51:

( i ) SEQUENCE CHARACTERISTICS:
            ( A ) LENGTH: 21 base pairs
            ( B ) TYPE: nucleic acid
            ( C ) STRANDEDNESS: single
            ( D ) TOPOLOGY: linear ( x i ) SEQUENCE DESCRIPTION: SEQ ID NO:51:

GAACAAATGC GTCCCATACT G                                        21

( 2 ) INFORMATION FOR SEQ ID NO:52:

( i ) SEQUENCE CHARACTERISTICS:

( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:52:

CTGCCGCTGG TTGATCTGGT C                    21

( 2 ) INFORMATION FOR SEQ ID NO:53:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( x i ) SEQUENCE DESCRIPTION: SEQ ID NO:53:

GGGTGTCCTC AGCTTCCTG                       19

( 2 ) INFORMATION FOR SEQ ID NO:54:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:54:

CTTGTACTGC GCCTCCGTCT G                    21

METHODS FOR IDENTIFYING A TYROSINE PHOSPHATASE ABNORMALITY ASSOCIATED WITH NEOPLASTIC DISEASE

GOVERNMENT SUPPORT

The invention described herein was supported in part by grants from the National Institutes of Health (5 ROI CA49152-04).

RELATED APPLICATIONS

This application is a continuation-in-part of U.S. Ser. No. 07/983,926, filed Dec. 1, 1992, by Robert M. Freeman, Jr., Jorge Plutzky, Benjamin G. Neel and Robert D. Rosenberg, now abandoned; which is a continuation-in-part of U.S. Ser. No. 07/829,141, filed Jan. 31, 1992, by Jorge Plutzky, Benjamin G. Neel and Robert D. Rosenberg, now abandoned; which is a continuation-in-part of U.S. Ser. No. 07/721,112, filed Jun. 26, 1991 by Jorge Plutzky, Benjamin G. Neel and Robert D. Rosenberg, now abandoned. The contents of these applications are incorporated herein by reference.

BACKGROUND OF THE INVENTION

Protein tyrosyl phosphorylation is an important cellular regulatory mechanism. Much work has implicated protein tyrosine kinases (PTKs) in the control of cell proliferation and differentiation. Many PTKs, when mutated and/or captured by retroviruses, can promote oncogenesis (Bishop, J. M., *Cell* 64:235–248 (1991); Cantley, L. et al., *Cell* 64:281–302 (1991); Hunter, T., *Cell* 64:249–270 (1991)). In addition, several PTKs have been shown to be essential for normal differentiation and development. For example, the Drosophila gene torso is essential for proper formation of anterior and posterior structures (Casanova, J. et al., *Genes and Devel.* 3:2025–2038 (1989)); Sprenger, F., et al., *Nature* 338:478–483 (1989)). The *Caenorhabditis elegans* let-23 gene regulates vulval development (Horvits, H. et al., *Nature* 351:535–541 (1991)), and murine c-kit is required during early embryogenesis for normal hematopoiesis (Geissler, E. N., et al., *Cell* 55:185–192 (1988); Chabot, B. et al., *Nature* 335:88–89 1988)).

Much has been learned about PTK signal transduction pathways (Cantley, L., et al., *Cell* 64:281–302 (1991)). Many growth factor (GF) receptors are transmembrane PTKs, which autophosphorylate upon ligand addition. Activated GF receptors are linked to downstream cellular events by recruitment of secondary signaling molecules to autophosphorylated receptors; some of these signaling molecules are also substrates for the receptor PTKs. Secondary signaling molecules such as GTPase-activating protein (Kaplan, D. R., et al. *Cell* 61:125–133 (1990)); phospholipase C-γ (Margolis, B., et al., *Cell* 57:1101–1107 (1989); Meisenhelder, J., et al., *Cell* 57:1109–1122 (1989)), and phosphatidylinositol 3-kinase (Otso, M., et al. *Cell* 65:91–104 (1991); Skolnik, E. Y., et al., *Cell* 65:83–90 (1991); Escobedo, J. A. et al. *Cell* 65:75–82 (1991)) associate with activated receptors through src-homology 2 (SH2) domains, conserved stretches of approximately 100 amino acids which promote intra- or inter-molecular protein-protein interactions via binding to specific phosphorylated tyrosyl residues (Koch, C., et al., *Science* 252:668–674 (1991)). Since different subsets of phosphotyrosyl proteins bind to different SH2 domains with varying avidity, the specificity of the cellular response to GFs may be largely determined by the strength and spectrum of these intermolecular SH2/phosphotyrosyl interactions (Koch, C. et al., *Science* 252:668–674 (1991)).

Src homology region 2 (SH2) is a sequence of about 100 amino acids and was originally identified in the v-Src and v-Fps tyrosine kinases. This noncatalytic domain is conserved among a variety of tyrosine kinases including Src, Src family members, and Fps, for example (Koch, C. A., et al., *Science* 252:668–674 (1991)). In addition, the SH2 domain is found in the cytoskeletal protein tension, as well as in several cytoplasmic signalling proteins that are regulated by receptor protein-tyrosine kinases, such as phospholipase C-γ and GAP (Ras GTPase activating protein) (Koch, C. A., et al., *Science* 252:668–674 (1991)).

The SH2 domains present in Src, Abl and Fps tyrosine kinases interact with the kinase domain to modulate activity and may play a role in substrate interaction. In cytoplasmic signalling proteins, the SH2 domain appears to mediate the formation of heteromeric complexes between growth factor receptors and the SH2 domain. In vitro studies have shown bonding of a fragment of GAP containing only the SH2 domains to a C-terminal phosphopeptide from the EGF receptor. It is also though that the SH2 domains of PI3K (phosphatidyl inositol 3'-kinase), GAP and PLC-γ recognize phosphorylated tyrosine on the β-PDGF receptor tyrosine kinase (Koch, C. A., et al., *Science* 252:668–674 (1991)).

The steady-state level of protein tyrosyl phosphorylation is also controlled by the opposing action of protein tyrosine phosphatases (PTPs); however, little is known about the role of PTPs in signal transduction. Molecular cloning of a large number of PTPs has revealed that they can be grouped into two forms, cytosolic and transmembrane (Fischer, E., et al., *Science* 253:401–406 (1991)). The cytosolic PTPs include PTP 1B and T cell PTP, both of low molecular weight (37 kD and 48 kD, respectively). These cytosolic PTPs consist primarily of a 300 amino acid domain containing two conserved cysteine active sites with 74% amino acid sequence homology between the two forms. These cytosolic PTPs can be further grouped into subfamilies, based upon distinctive structural features of their non-catalytic regions. These include the presence of a hydrophobic C-terminal sequence in PTP-IB and T-cell PTP (Cool, D. E., et al., *Proc. Natl. Acad. Sci. USA* 86:5257–5261; Chernoff, J., et al., *Proc. Natl. Acad. Sci. USA* 87:2735–2739 (1990); Brown-Shimer, S. et al., *Proc. Natl. Acad. Sci. USA* 87:5148–5152 (1990)), as well as the presence of domains with similarity to cytoskeletal proteins in PTP-Meg (Gu, M. et al., *Proc. Natl. Acad. USA* 88:5867–5871 (1991)) and PTP-HI (Yang, Q., et al., *Proc. Natl. Acad. USA* 88:5949–5953 (1991)). Whether these structural similarities have functional significance is not yet known; the regulation and function of non-transmembrane PTPs remain obscure.

The transmembrane PTPs include CD45, also known as leukocyte common antigen (LCA) (Charbonneau, H. et al., *Proc. Natl. Acad. Sci. USA* 85:7182–7186 (1988)); leukocyte common antigen related protein (LAR) (Streuli, M. et al., *J. Exp. Med.* 168:1523–1530 (1988)); and two Drosophila homologs (DPTP and DLAR). These transmembrane PTPs are thought to be receptors which modulate their activity in response to ligands as yet unidentified. The transmembrane forms contain a duplication of the 300 amino acid domain present in cytosolic PTPs, creating an imperfect tandem repeat with extensive internal homology between domains I and II. The tandem 300 amino acid domains display homology across forms (to other PTP's of both classes), and across species (human, rat, mouse—90% homology). Of the four conserved cysteines in the 300 amino acid tandem domains (2 per domain), only the first appears essential for phosphatase activity. Two of the cysteines in the first domain represent 2 out of 40 invariant amino acid residues in the first domain of all known PTPs. Although no PTPs have any serine/threonine phosphatase homology, the trans-membrane PTPs possess short hydrophobic transmembrane stretches followed by extracellular regions with immunoglobulin- and fibronectin-like repeats, consistent with ligand binding regions. Despite the sequence conservation in the intracellular (cytoplasmic) domains of the molecules, the extracellular portions have no homology with one another.

Further information concerning PTPs may provide insight into the role of PTPs in cellular function and in regulatory mechanisms in the cell.

SUMMARY OF THE INVENTION

The present invention relates to the isolation of genes encoding novel protein tyrosine phosphatases (PTPs), the nucleic acid sequences isolated, and the encoded phosphatases. In particular, two clones encoding PTPs, designated M1PTP (see SEQ ID NO.: 1 and NO.: 2) and M2PTP (see SEQ ID NO.: 3 and NO.: 4), were isolated from a rat megakaryocyte cDNA library. A probe from the M1PTP clone was used to isolate a human cDNA clone, designated SH-PTP1 (SEQ ID NO.: 5). Surprisingly, this clone contains two tandem Src homology 2 (SH2) domains, in addition to a cytosolic PTP homology domain. The SH-PTP1 gene sequences (see SEQ ID NO.: 5), or a portion thereof, may be used to isolate genes encoding related PTPs and other related SH2-containing proteins in particular. SH-PTP1 may be the prototype of a class of tyrosine phosphatases with SH2 domains. SH-PTP1 was found to map to 12p13, a region commonly involved in leukemia-associated chromosomal abnormalities. Gross chromosomal abnormalities are found in this region in approximately 10% of patients with acute lymphoblastic leukemia (ALL). In an analysis of the SH-PTP1 gene in an ALL patient by single strand conformational polymorphism analysis, abnormalities consisting of significantly smaller bands were detected in DNA samples. The smaller bands were found to have a 117 nucleotide deletion compared to the wild type sequence. This deletion corresponded to nucleotides 537–653 of the SH-PTP1 cDNA sequence, which corresponds in the protein sequence to roughly the second half of the second SH2 domain of SH-PTP1. Western blot analysis of other ALL patients also demonstrated putative abnormalities in SH-PTP1 expression, including low levels of SH-PTP1 expression and smaller proteins immunoreactive with anti-SH-PTP1 antibodies (see Example 5). Thus, SH-PTP1 and sequences which hybridize to SH-PTP1 can be used as probes or primers in methods of detecting abnormalities associated with neoplastic disease, such as for diagnosis or for detection of minimal residual disease.

The invention further relates to methods of altering tyrosine phosphatase activities encoded by the novel phosphatases. By altering (i.e., increasing or decreasing) tyrosine phosphatase activity, one can alter megakaryocyte cell function, and thereby alter platelet production.

In addition, the current invention pertains to a clone, designated 3B4-15, isolated from a λgt11 rat brain cDNA library. This clone, which contains a fragment of a novel PTP, was used to screen the rat brain library. A partial rat brain cDNA from this screen was used to screen a λgt11 human lung cDNA library; a cDNA clone from the human lung library was used to screen a λAZapII human fetal brain library. From this library was isolated several partial cDNA clones, and a clone encoding a novel PTP gene, designated S-PTP2 (SEQ ID NO.: 11). The SH-PTP2 gene sequences, or a portion thereof, may also be used to isolate genes encoding related PTPs and other related SH2-containing proteins in particular. SH-PTP2 was found to be expressed nearly ubiquitously and to be homologous to the *Drosophilia corkscrew* gene. Thus, SH-PTP2 and sequences which hybridize to S-PTP2 can be used to locate other genes which are involved in cellular growth control.

BRIEF DESCRIPTION OF THE DRAWINGS

FIG. 2 is the nucleic acid sequence of the coding strand of the human SH-PTP1 gene (SEQ ID NO.: 5). The two SH2 domains are underlined. The predicted protein sequence is shown. Standard single letter amino acid abbreviations are used: A=Ala; R=Arg; N=Asn; D=Asp; C=Cys; Q=Gln; E=Glu; G=Gly; H=His; I=Ile; L=Leu; K=Lys; M=Met; F=Phe; P=Pro; S=Ser; T=Thr; W=Trp; Y=Tyr; and V=Val. The two SH2 domains are underlined. Asterisks denote the stop codon, and a polyadenylation signal is marked by arrowheads. A potential phosphorylation site for cdc2 kinase is indicated by double underlining, and two potential tyrosine phosphorylation sites are noted by a dotted underline.

FIG. 4B) by an SH-PTP fusion protein.

FIG. 6A shows the amino acid sequence comparisons of the phosphatase domains of rat brain SH-PTP2 (3B4-15 clone) (SEQ ID NO.: 15) and human fetal brain SH-PTP2 (SEQ ID NO.: 16) with other members of the PTP family. The phosphatase domains of the other members of the PTP family shown are csw (Csw; SEQ ID NO.: 17); SH-PTP1 (SEQ ID NO.: 18); human receptor-linked PTPμ (hum RPTPμ; SEQ ID NO.: 19); human PTPβ (hum HPTPβ; SEQ ID NO.: 20); human LAR (hum LAR; SEQ ID NO.: 21); human PTPδ (SEQ ID NO.: 22); and DLAR (SEQ ID NO.: 23). Solid lines indicate identical residues; conservative substitutions, as determined by GAP (Devereux, J., et al., *Nucl. Acids Res.* 12:387–395 (1984)), are marked by colons and periods. In proteins containing more than one phosphatase domain, the N-terminal domain is shown. Residues common to SH-PTP2 and csw are indicated by boldface type and are also highlighted in the other PTPs; highly conserved residues found in PTPs are indicated by asterisks. Gapped alignments were made using PILEUP (Devereux, J., et al., *Nucl. Acids Res.* 12:387–395 (1984)). Sequence similarity extends throughout the entire PTP domain and is not shown due to space limitations.

FIG. 6B shows the nucleic acid sequence and the predicted amino acid sequence of human SH-PTP2 (SEQ ID NO.: 11). The nucleic acid sequence is numbered on the right and the predicted amino acid sequence is numbered underneath the amino acids. The two SH2 domains are indicated by a solid underline and the phosphatase domain is indicated by a dotted underline. Positions of the oligonucleotides used to prime the rat 3B4-15 fragment are in boldface type. Potential serine/threonine or tyrosine phosphorylation sites (Kennelly, P. J., et al., *J. Biol. Chem.* 266:15555–15558 (1991), Kemp, B. E., et al., TIBS 15:342–346 (1990)) include: T127, S499, S576, and S591 for protein kinase C; T12, T73, S118, T153, S189, S264, T337, T356, T397, T422, S448, S548, T553 for casein kinase II; S189, S234, S265, S576 for S6 kinase; S558, T564, T566 for cdc2; and Y62, Y63, Y66, 79, Y375 for tyrosine kinases. An asterisk denotes the stop codon. The sequences of the remaining 5' and 3' untranslated regions have not yet been determined.

FIG. 7 is an illustration of amino acid sequence comparisons between SH-PTP2, csw, SH-PTP1, and other known SH2 domains. The following amino acid sequences are shown: amino-terminal SH2 domain of SH-PTP2 (SH-PTP2-N; SEQ ID NO.: 24); amino-terminal SH2 domain of csw (Csw-N; SEQ ID NO.: 25); amino-terminal SH2 domain of SH-PTP1 (SH-PTP1N; SEQ ID NO.: 26); carboxyl-terminal SH2 domain of SH-PTP2 (SH-PTP2-C; SEQ ID NO.: 27); carboxyl-terminal SH2 domain of csw (Csw-C; SEQ ID NO.: 28); carboxyl-terminal SH2 domain of SH-PTP1 (SH-PTP1-C; SEQ ID NO.: 29); SH2 domain of human fer (hum fer; SEQ ID NO.: 30); SH2 domain of bovine guanidine triphosphate (GTPase) activating protein (bov GAP; SEQ ID NO.: 31); amino-terminal SH2 domain of mouse fgr (mouse fgr-N; SEQ ID NO.: 32); amino-terminal SH2 domain of human Nck (hum Nck-N; SEQ ID NO.: 33); SH2 domain of hydra stk (hydra stk; SEQ ID NO.: 34); carboxyl-terminal SH2 domain of mouse fgr (mouse fgr-C; SEQ ID NO.: 35); SH2 domain of chicken yes (Chick yes; SEQ ID NO.: 36); SH2 domain of human fyn (hum fyn; SEQ ID NO.: 37); SH2 domain of mouse lsk (mouse lsk; SEQ ID NO.: 38); SH2 domain of mouse blk (mouse blk; SEQ ID NO.: 39); carboxyl-terminal SH2 domain of human Nck (hum Nck-C; SEQ ID NO.: 40); and the consensus regions. The two SH2 domains of SH-PTP2, SH-PTP1 and csw are aligned with and compared above other SH2-containing proteins. A consensus sequence for the SH2 domains found in SH2-containing PTPs is given. Residues common to SH-PTP2 and csw are indicated by boldface type and are also highlighted in the other SH2-containing proteins. A • indicates invariant residues in SH2 proteins; +marks basic amino acids thought to be involved in phosphotyrosine recognition (Koch, E., et al., *Science* 252:668–674 (1991)). Those proteins with two SH2 domains are suffixed —N for amino-terminal and —C for carboxyl-terminal domains. Gapped alignments were made using PILEUP (Devereux, J., et al., *Nucl. Acids Res.* 12:387–395 (1984)) and are grouped into the conserved SH2 subdomains I-V ((Koch, E., et al., *Science* 252:668–674 (1991)).

FIG. 9 shows the amino acid sequences for primers which can be used to amplify regions of SH-PTP1 DNA. 200A =SEQ ID NO.: 41; 200B=SEQ ID NO.: 42; 400A=SEQ ID NO.: 43; 400B=SEQ ID NO.: 44; 600A=SEQ ID NO.: 45; 600B=SEQ ID NO.: 46; 800A=SEQ ID NO.: 47; 800B= SEQ ID NO.: 48; 1000A=SEQ ID NO.: 49; 1000B=SEQ ID NO.: 50; 1200A=SEQ ID NO.: 51; 1200B=SEQ ID NO.: 52; 1400A =SEQ ID NO.: 53, AND 1400B=SEQ ID NO.: 54.

DETAILED DESCRIPTION OF THE INVENTION

Figure 1:
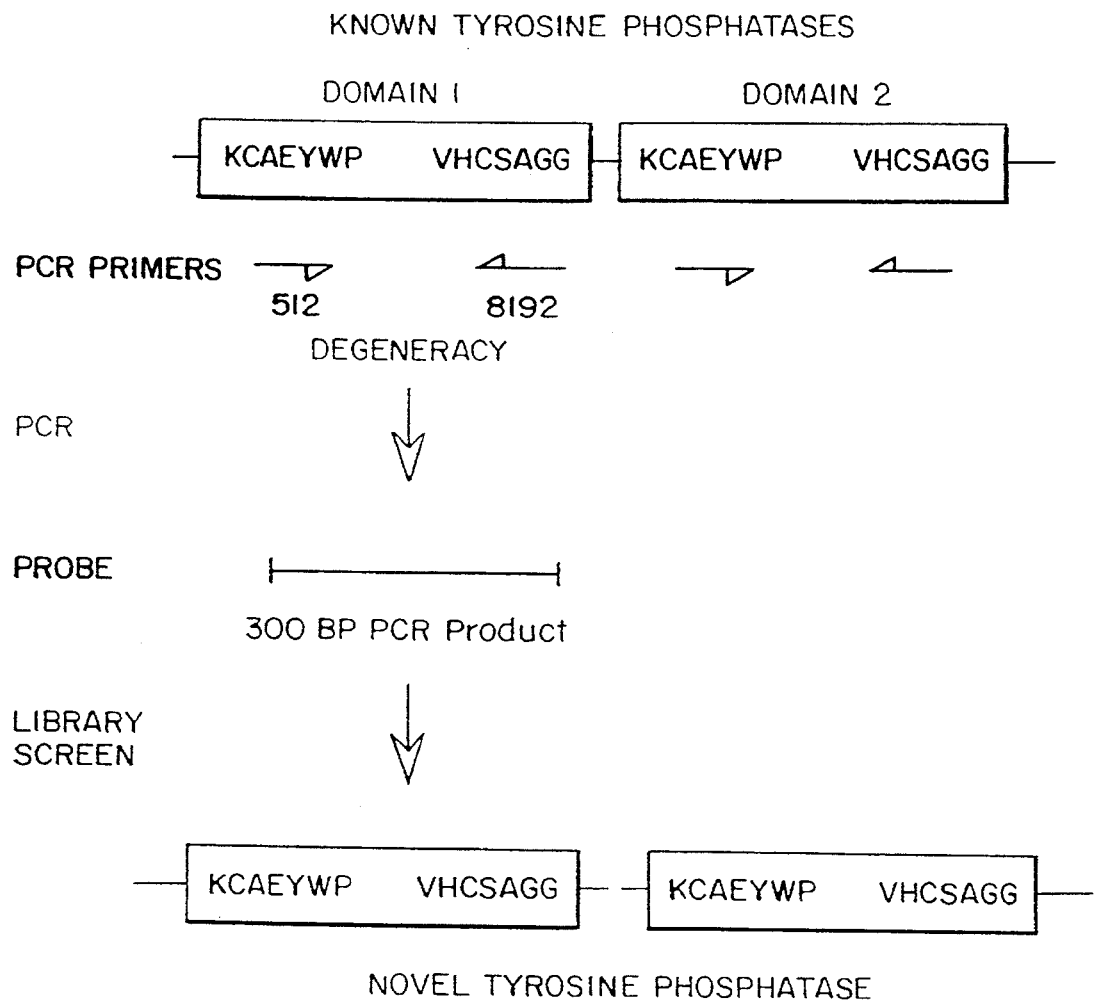
FIG. 1 is a schematic illustration of the cloning strategy used to isolate SH-PTP1. Degenerate oligonucleotide primers with homology to nucleotide sequences encoding the amino acid sequences Lys-Cys-Ala-Glu-Tyr-Trp-Pro (KCAEYWP) and Val-His-Cys-Ser-Ala-Gly-Gly (VHC-SAGG), with degeneracy of 512 and 8192, respectively, are represented by arrows. The expected 300 bp PCR product from PTP domain 1 is indicated. This probe is used to screen a library to isolate related clones with one or more homology domains.

Protein tyrosine phosphatases (PTPs) represent a family of enzymes which dephosphorylate tyrosine residues in a highly specific manner. As such, they control, along with phosphotyrosine kinases (PTKs), tyrosine phosphorylation states, a factor implicated in many aspects of cell function: growth factor responses, cellular differentiation, cell cycle control and neoplastic transformation. Megakaryocytes, as a hematopoietic lineage, are of particular interest with regard to tyrosine phosphorylation. Megakaryocytes contain large amounts of tyrosine kinase activity, and of the PTK c-src in particular (Golden, et al., *Proc. Natl. Acad. Sci. USA*, 83:852 (1986)). Rapid changes in tyrosine phosphorylation are seen in platelets in response to physiological agonists like thrombin (Golden, et al., *Proc. Natl. Acad. Sci. USA*, 86:901 (1986); Ferrel and Martin, *Mol. Cell Biol.* 8:3603 (1988)). Physiologically, megakaryocytes are influenced by multiple hematopoietic growth factors, and exhibit a unique cell cycle that allows endoreduplication (nuclear duplication to highly ploidy states without cell division), with known potential for transformation. Eventually, megakaryocytes produce platelets, highly reactive cytoplasmic fragments with abundant phosphotyrosine levels, which vary in response to stimulation. The identification of novel members of the PTP family in megakaryocytes could clarify the role of tyrosine phosphatases in megakaryocyte function.

Isolation of a Novel PTP—First Method

As described in Example 1, in order to identify novel PTPs, a pair of degenerate oligonucleotide primers derived from conserved peptide regions of known PTPs was used in the polymerase chain reaction to isolate novel members of the PTP family from a rat megakaryocyte library. The primers spanned conserved cysteine residues in both duplicated PTP domains of CD45, DPTP, DLAR, and the single domain of PTP1B. Several PCR products were observed; however, only the expected 300 bp PCR product yielded protein tyrosine phosphatase sequences. The PCR products were cloned and 20 isolates were sequenced. Multiple PTP forms were identified including LAR, LRP, CD45, as well as two novel highly conserved PTP clones.

The 300 bp fragments from the novel isolates were utilized as probes to screen a rat megakaryocyte cDNA library. The clones corresponding to two novel PTPs, designated M1PTP and M2PTP, were further characterized. Of the two novel PTP's, the first, designated M1PTP (SEQ ID NO.: 1 and NO.: 2), encodes a 3.0 kb message with high homology to rat and human LAR, LRP, LCA and PTP1B across the first phosphatase domain (approximately 56% nucleic acid homology). RNA expression of M1PTP appeared to be predominantly in lung and megakaryocytes, as determined by Northern analysis. The second novel PTP, designated M2PTP (SEQ ID NO.: 3 and NO.: 4), has an 8 kb message with expression largely limited to megakaryocytes.

These studies reveal the ability of degenerate oligo-based PCR to identify PTPs that are not only novel but also of apparently restricted tissue expression. Clones encoding M1PTP and M2PTP will be useful in determining the role of tyrosine phosphatases in pulmonary and megakaryocyte physiology, for example.

As the M1PTP rat clone appeared to be incomplete, the insert was used in an additional screening of human lung and human erythroleukemia cell cDNA libraries. Several overlapping clones were isolated from each library. Sequence analysis of the clones revealed a full-length cDNA (FIG. 2).

Properties of SH-PTP1

The nucleotide sequence of the human clones encodes a predicted protein of 595 amino acids (FIG. 2; SEQ ID NO.: 5 and NO.: 6). The 300 amino acid PTP homology domain is located near the C-terminal end of the predicted protein (see FIG. 3), and retains all 25 invariant and many conserved amino acids of the PTP family. SH-PTP1 appears to lack a signal sequence or potential transmembrane region, indicating that it is a non-transmembrane PTP. SH-PTP1 encodes a protein having phosphatase activity (Example 1).

Figure 3:
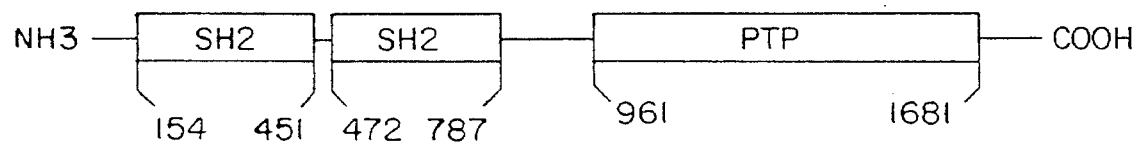
FIG. 3 is a schematic diagram of the domain structure of the protein encoded by the human SH-PTP1 gene. The tandem SH2 domains are indicated (SH2) and the region having homology to the low-$M_r$ (cytosolic) protein tyrosine phosphatases is indicated (PTP). Numbers refer to positions in the predicted amino acid sequence. "NH3" indicates the amino-terminus and "COOH" indicates the carboxyl-terminus.

Surprisingly, the N-terminal end of the protein has two tandem SH2 homology repeats (underlined in FIG. 2; see also FIG. 3). Thus, the gene was designated SHPTP1. The N-terminal SH2 domain (SH2-N) begins at amino acid position 4, and the second SH2 domain (SH2-C) begins at amino acid position 110.

The homology between the two SH2 regions of SH-PTP1 and known SH2 domains spans the entire SH2 domain, clustering within the five conserved subdomains (Koch, C.A., et al., *Science* 252:668–674 (1991)). The three invariant residues of SH2 proteins are present in both SH2 domains of SH-PTP1. Two out of three basic amino acid residues proposed as possible phosphotyrosine recognition sites are also present. As with other SH2 proteins, the conserved subdomains of SH-PTP1 are interrupted by glycine/proline rich variable regions. Overall, the two SH2 domains in SH-PTP1 are most similar to the two SH2 domains of GAP (45% identity).

SH-PTP1 contains several potential phosphorylation sites (FIG. 2). There is a single site located in the second SH2 domain which conforms to the consensus target sequence for the cell cycle regulated cdc2 kinase (FIG. 2; Maller, *Biochemistry* 29:3157 (1990); Shalloway and Nurse, *J. Cell Science, Supp.* 12:53). There are also 12 potential tyrosine phosphorylation sites near the C-terminus. Numerous possible phosphorylation sites for other serine/threonine kinases exist throughout the molecule (Kemp and Pearson, *Trends in Biochem. Sci.* 15:342 (1990)).

Expression of SH-PTP1 and Implications for Its Role in Cell Signal Transduction

Interestingly, SH-PTP1 is expressed at high levels predominantly in hematopoietic cells. Disturbances in regulation of the activity of protein tyrosine kinases in hematopoietic cells, due to chromosomal abnormalities (e.g., the t(9;22) translocation in chronic myelogenous leukemia resulting in the bcr-abl gene fusion) or to retroviral gene transduction (e.g., of the v-erb B onogene), can contribute to leukemogenesis. Similarly, it is conceivable that deranged control of PTP with a key role in signal transduction could have similarly deleterious effects. Therefore, panels of somatic cell hybrids and fluorescent in situ hybridization were used to determine the chromosomal localization of the tyrosine phosphatase, SH-PTP1, which contains two SH2 domains. As shown in Example 2, SH-PTP1 was found to map to 12p13, a region commonly involved in leukemia-associated chromosomal abnormalities. Since SH-PTP1 is expressed at high levels in hematopoietic cells of all lineages, and since its expression is induced early in hematopoietic differentiation, altered expression and/or structure of SH-PTP1 may play a role in leukemogenesis. This hypothesis is supported by data demonstrating an abnormality in the SH-PTP1 gene of a patient with acute lymphoblastic leukemia (ALL). As described in Example 5, an ALL patient was found to have a deletion in the SH-PTP1 gene corresponding to roughly the second half of the second SH2 domain of the SH-PTP1 protein.

The presence of SH2 domains in a PTP also suggests several possible roles for SH-PTP1 in signal transduction (Plutzky, J., et al. *Proc. Natl. Acad. USA* 88:1123–1127 (1992); Yi, T., et al., *Mol. Cell. Biol.* 12:836–846 (1992); Shen, S.—H., et al., *Nature* 52:736–739 (1991); Matthews, R. J., et al., *Mol. Cell. Biol.* 12:2396–2405 (1992)). Further clues were provided by the recent finding that the Drosophilia developmental gene corkscrew (csw) is also a PTP containing two SH2 domains (Perkins, L. A. et al., *Cell* 70:225–236 (1992)). csw functions in the terminal class signal transduction pathway in concert with the Drosophila l(1)polehole gene to positively transduce signals generated by the torso receptor PTK (Perkins, L., et al., *Cell* 70:225–236 (1992)). l(1)polehole (D-raf) is the Drosophila counterpart of mammalian c-raf, a serine/threonine kinase (Ambrosio, L., et al., *Nature* 342.:288–290 (1989)). Based on sequence similarity between csw and SH-PTP1, Perkins et al. (*Cell* 70:225–236 (1992)) suggested that SH-PTP1 might the mammalian csw homolog. However, unlike SH-PTP1, which is found mainly in hematopoietic cells (Plutzky, J., et al., *Proc. Natl. Acad. USA* 88:1123–1127 (1992); Yi, T., et al., *Mol. Cell. Biol.* 12:836–846 (1992); Matthews, R. J., et al., *Mol. Cell. Biol.* 12:2396–2405 (1992))), csw is expressed ubiquitously during embryogenesis (Perkins, L., et al., *Cell* 70:225–236 (1992)).

Identification of a Novel PTP—Second Method

As described in Example 3, a method slightly different from that used to isolate SH-PTP1 was employed to isolate additional novel PTPs. Degenerate mixed oligonucleotides (sense, AA(A/G)TG(C/T) (C/G) (A/C)X(C/G)A(A/G)TA(C/T)TGGCC (SEQ ID NO.: 13); antisense, CCXA(C/T)XCCXGCXGA(A/G)CA(A/G)TGXAC (SEQ ID NO.: 14)) to conserved sequences in the catalytic domains of known PTPs, including SH-PTP1, were used to prime PCRs from a rat brain cDNA library. PCR fragments of the same size as those from the non-transmembrane PTP PTP-1B (~300 bp) were subcloned and sequenced. Forty-two subclones which contained sequences from the phage vector or the elongation factor, but not conserved sequences from PTPs, were labeled and used in negative selection to eliminate any remaining clones which contained phage vector or elongation factor, but not sequences. Over half of the remaining clones contained inserts with strong PTP similarities; although most represented rat homologs of known PTPs, one novel clone, designated 3B4-15, was isolated (SEQ ID NO.: 9). 3B4-15 was used to re-screen the rat cDNA library and partial cDNAs from the rat cDNA library were used to screen a human being library. A partial cDNA clone from the lung library was used in turn to screen a human fetal brain cDNA library, which resulted in several partial cDNA clones as well as a novel PTP gene, designated SH-PTP2 (SEQ ID NO.: 11).

Properties of SH-PTP2

The nucleotide sequence of the human clone encodes a predicted protein of 593 amino acids (SEQ ID NO.: 11 and 12), with a predicted molecular weight of 68 kD. A single tyrosine phosphatase domain is located at amino acids 268–525; it contains residues essential for catalysis. Two SH2 domains are found N-terminal to the PTP domain. No hydrophobic region appears to be present, indicating that SH-PTP2, like SH-PTP1, is a cytosolic protein. Human SH-PTP2 was found to be similar to the Drosophilia gene corkscrew (csw); overall, the protein sequences are 62% identical. As described in Example 3, the SH2 domains of SH-PTP2 are more similar to csw than to SH-PTP1.

Role of SH2 Domains in PTPs

The specificity and avidity of SH2 domains for phosphotyrosyl residues are dictated by their amino acid sequences (Koch, C., et al., *Science 252:668–674* (1991)). Since the SH2 domains of SH-PTps comprise a distinct subfamily, the SH-PTPs may bind to similar or related subsets of phosphotyrosyl proteins. In addition, the phosphotyrosyl binding partners of the SH-PTPs may be distinct from those bound by other SH2-containing proteins. As mentioned above, the first conserved basic amino acid in both SH2 domains of the SH-PTPs is replaced by a glycol residue. Recent x-ray co-crystallographic studies of the SH2 domain of Src (J. Kuriyan, personal communication) indicate that this conserved residue is located on the surface and interacts with the phenolic ring of the bound phosphotyrosine. SH2 domains with an arginine to glycine substitution at this position might be predicted to have lower avidity and/or relaxed specificity for phosphotyrosyl peptides. Decreased avidity of binding might be important to prevent binding of SH-PTPs to key tyrosyl-phosphorylated secondary signaling molecules at inappropriate times during signal transmission. Specific SH-PTP2/phosphotyrosyl interactions might then be promoted at particular times by post-translational modifications of SH-PTP2 that function to increase binding avidity. Altered specificity conceivably could include binding to phosphoseryl or phosphothreonyl residues. However, substitution at the first conserved basic residue is clearly not necessary for relaxed specificity; the SH2 domain of Abl, which does bind to serylphosphorylated peptides (Pendergast, A. M., et al., *Cell 66:161–171* (1991)), has an arginine at this position. Moreover, glycol substitution does not preclude phosphotyrosyl binding, since recent work indicates that SH-PTP1 binds to specific phosphotyrosyl proteins. Experiments in progress should help to define how glycol substitution alters the physicochemical properties of SH2-phospho-tyrosyl peptide interactions.

The SH2 domain of an SH-PTP could target an SH-PTP to signal transduction complexes for signal termination or amplification. Termination could occur by reversing the tyrosine phosphorylation of receptor activated signalling proteins. Amplification could take place by releasing bound signaling molecules, freeing them to find other substrates within the cell.

The observation of SH2 domains in a PTP, previously identified only in tyrosine kinases, signal transduction proteins, and certain cytoskeletal proteins (e.g., tension) provides a possible link between the tyrosine kinases and tyrosine phosphatases. Both classes of proteins have recognized roles in control of the cell cycle. Phosphorylation of tyrosine has also been implicated in the response of cells to growth factors and hormones. The balance between phosphorylated and dephosphorylated states depends upon the balance of activities of tyrosine kinases and tyrosine phosphatases.

Coordination of the activities of kinases and phosphatases may occur through the SH2 domains. Specific regulatory proteins may coregulate specific kinases and phosphatases to regulate processes of the cell cycle. In addition, an SH2 domain of a selected tyrosine phosphatase may interact with a selected tyrosine kinase to regulate kinase function. Such interaction could occur at a site of auto-phosphorylation on the tyrosine kinase, for example. In megakaryocytes, such regulation could be essential to the control of megakaryocytopoiesis and the unique cell cycle.

Uses of the Present Invention

The strategies outlined herein can be used to isolate other PTPs. Other degenerate probes may be designed based on the conserved sequences present in SH-PTP1 (SEQ ID NO.: 5), or SH-PTP2 (SEQ ID NO.: 11), for example. In addition, the cloned M1PTP, M2PTP, SH-PTP1, 3B4-15, and SH-PTP2 genes, or portions of each of the foregoing, can be used as probes to isolate additional PTPs. A "portion" of a gene, as used herein, indicates a part of the gene encoding conserved sequences in the M1PTP, SH-PTP1, 3B4-15, and SH-PTP2 genes. The SH2 domains of these genes are of particular interest as possible probes for PTPs or other proteins with one or more SH2 homology regions. Possibly, specific SH2 regions will be found in association with coregulated tyrosine phosphatases and tyrosine kinases. To obtain other PTPs, stringency conditions should be tailored to eliminate hybridization of the probes to extraneous DNA sequences (see Sambrook et al. (eds), Molecular Cloning: A Laboratory Manual (2nd ed.) V.2, Cold Spring Harbor Laboratories Press (1989), particularly ch. 11.45).

Novel PTP genes or nucleotide sequences which can be isolated using M1PTP (see SEQ ID NO.: 1), M2PTP (see SEQ ID NO.: 3), SH-PTP1 (SEQ ID NO.: 5), or portions thereof, under conditions which result in the isolation of M1PTP, M2PTP, or SH-PTP1, and which encode at least one SH2 domain, are designated "MPTP homologs". SH-PTP1 itself is an example of an MPTP homolog. If less stringent conditions than those used to isolate M1PTP, M2PTP and SH-PTP1 are used, the isolated genes will be termed "MPTP related". Novel PTP genes or nucleotide sequences which can be isolated using 3B4-15(SEQ ID NO.: 9), SH-PTP2 (SEQ ID NO.: 11), or portions thereof, under conditions which result in the isolation of SH-PTP2 and which encode of least one SH2 domain, are designated "3B4-15 homologs". SH-PTP2 is an example of a 3B4-15 homolog. If less stringent conditions are used, the isolated genes will be termed "3B4-15 related."

Use of an SH2 region as a probe could lead to the isolation of genes for tyrosine kinases, and further, for signal transduction proteins. For example, by analogy to phospholipase C-γ, signal transduction proteins which mediate megakaryocyte responses to a growth factor may contain SH2 domains. Species such as these do not contain PTP homology domains, but can be isolated using SH2 domains as probes. If isolated under conditions which lead to isolation of M1PTP, M2PTP, SH-PTP1, 3B4-15, or SH-PTP2 these species would be termed "SH2 homologs". If less stringent conditions are used, the isolated genes or nucleic acid sequences are termed "SH2 related".

The cloned genes can be used to produce proteins or peptides encoded by the nucleotide sequences (see e.g., SEQ ID NO.: 2, NO.: 4, NO.: 6, NO.: 10, and NO.: 12). The isolation and characterization of additional PTPs encoded by homologs can provide information regarding the regulation of pathways controlled by tyrosine phosphorylation and dephosphorylation.

(a) Uses of MPTP Homologs and MPTP-Related Genes

By overexpressing or interfering with the function of megakaryocyte PTPs or MPTP homologs, one can alter megakaryocyte and/or platelet function. PTPs may have a role in controlling the differentiation of stem cells into megakaryocytes (megakaryocytopoiesis) and the megakaryocyte cell cycle. As used herein, megakaryocytopoiesis refers to the differentiation of megakaryocytes from stem or progenitor cells, as well as to the endoreduplication process which generates polyploid megakaryocytes. Fragmentation of megakaryocytes generates small nucleate platelets, which are required for normal hemostasis. Thus, alteration of megakaryocyte function, in turn will influence platelet function.

A number of clinical disorders of megakaryocytopoiesis are known, such as congenital megakaryocyte hypoplasia, acquired a megakaryocytic thrombocytopenic purpura, and megakaryoblastic leukemia (Gewirtz, A. M. and Hoffman, R., *Hematology/Oncology Clinics of North America* 4(1):43–64 (1990)). Increases in bone marrow megakaryocytes and thrombocytosis are frequently observed in myeloproliferative disorders. In addition, megakaryocyte hyperplasia and increased platelet counts have been observed in association with a variety of disease states, including infection and cancer (solid tumors). Platelets play a role in pathological processes, such as thrombosis, atherogenesis, and cancer cell metastasis. Platelets are also important in wound healing. Thus, pathogenic states are associated with both increases and decreases in megakaryocyte and platelet function.

Increasing or decreasing MPTP activity (e.g., tyrosine phosphorylation) to alter (i.e., increase or decrease) megakaryocyte function (e.g., megakaryocytopoiesis) may have therapeutic value in treating disorders and pathological processes in which megakaryocytes and platelets are involved, such as those described above. For example, the SH-PTP1 gene can be inserted into an appropriate retroviral expression vector and introduced into bone marrow stem cells to alter megakaryocyte and/or platelet function. Expression of a fragment of the SH-PTP1 gene or a mutated version (e.g., dominant negative mutant) may lead to interference with SH-PTP1 function, and a desired alteration in activity. In one embodiment, expression of a fragment of SH-PTP1 comprising an SH2 domain can lead to modulation of SH-PTP1 activity.

In another embodiment, a mutant which is inactive as a phosphatase is designed and introduced into a cell. Cellular (e.g., megakaryocyte) proteins which normally interact with a PTP via its SH2 domain can interact with the sH2 domain of the inactive mutant PTP, rather than with the corresponding cellular PTP. In effect, such an inactive mutant PTP acts as a decoy, and can be used to modulate PTP function in the cell, thereby altering cell function. Such mutants are also useful for studying SH-PTPase function. A mutant lacking phosphatase activity is described in Example 1.

Interestingly, one of the clones isolated from the HEL cell line contains a two-base deletion (SEQ ID NO.: 7) relative to the SH-PTP1 sequence (SEQ ID NO.: 5). This deletion (AG at position 1868–1869) results in a change in reading frame and is predicted to generate a variant protein with an altered and extended C-terminus (see SEQ ID NO.: 8) relative to that encoded by SH-PTP1 (SEQ ID NO.: 5 and NO.: 6). It is possible that, in addition to the version designated SH-PTP1 (SEQ ID NO.: 5), the HEL cell line encodes an altered version of SH-PTP1 (a variant SH-PTP1; SEQ ID NO.: 7). cDNAs corresponding to the variant SH-PTP1 and to SH-PTP1 were isolated from the HEL line library, while only SH-PTP1 was isolated from the lung library. Possibly, the variant form arises from use of a cryptic splice acceptor site. Alternatively, the variant may have altered activity which has contributed to transformation of the cell line.

The localization of SH-PTP1 at 12p13 is also of interest (Example 2), since the distal short arm of chromosome 12 is involved in chromosomal abnormalities in several forms of leukemia. Approximately 10% of pediatric acute lymphoblastic leukemia (ALL) cases display abnormalities in the 12p12-13 region; these include interstitial and terminal deletions and trans-locations (Raimondi et al., *Blood* 68:69–75 (1986); Carroll et al., *Blood* 70:1962–1965 (1987)). Several different chromosomes participate with 12p in these translocations, suggesting that a 12p gene(s) is the target for these rearrangements. An intriguing exception to this theme is the dicentric translocation [tdic (9;12) (p11;p12)] found in about 1% of pediatric ALLs (Carroll et al., *Blood* 70:1962–1965 (1987)). Deletions of the 9p11 region are found independently in ALL (Pellet et al., *Leukemia* 5:468–472 (1991)), raising the tantalizing possibility that the dicentric translocation simultaneously targets 9p and 12p genes. Adult leukemias, of both lymphoid and myeloid origin, also display 12p abnormalities, although at much lower frequency (Zaccaria et al., *Cancer Genet. Cytogenet.* 15:309–314 (1985); Wilmoth et al., *Cancer Genet. Cytogenet.* 15:95–98 (1985); Berger et al., *Cancer Genet. Cytogenet.* 29:9–21 (1987); Keene et al., *Br. J. Haematol.* 67:25–31 (1987)). Such abnormalities may be particularly common in leukemias associated with eosinophilia (Keene et al., *Br. J. Haematol.* 67:25–31 (1987). Involvement of 12p12 has been implicated in some studies and 12p13 in others. However, given the difficulty of precisely specifying chromosomal breakpoints in clinical specimens, it is possible that all of these leukemia-associated 12p abnormalities are targeting a single gene, an SH-PTP, at 12p.

The ubiquitous expression in hematopoietic cells of all lineages and differentiation stages suggests that SHPTP1 plays an important role in hematopoietic cell signal transduction. This notion is further supported by data indicating that SH-PTP1 expression is induced at an early stage of hematopoietic cell differentiation (not shown). Mutations in an SH2-containing PTP could perturb normal hematopoietic growth or differentiation. Thus, SH-PTP1 is a good candidate for the gene targeted by leukemia-associated 12p chromosome abnormalities. As such, an SHPTP1 sequence can be used in the diagnosis of neoplastic disease. Sequences of SH-PTP1 can be particularly useful for diagnosis of neoplasias associated with chromosome 12p abnormalities (e.g., translocations, inversions, deletions, mutations) and of 12p13 abnormalities, for confirmation of such a diagnosis, for monitoring the progression of treatment, and/or for detection of minimal residual disease. In addition, other sequences capable of hybridizing with SH-PTP1 (e.g., other SH-PTPs) can also be used for diagnosis of chromosome 12p-related neoplasia. For instance, SH-PTP1 can be as useful in the diagnosis of leukemia of lymphoid or myeloid origin in an individual, such as acute leukemia (e.g., adult or pediatric acute lympho-blastic leukemia). Other SH-PTPs may be similarly associated with neoplasia and can be useful for detecting abnormalities which are indicative of the presence of those diseases.

For example, it is possible to detect chromosome 12p abnormalities using as a probe a nucleotide sequence which is complementary to all or a portion of either strand of the SH-PTP1 gene (e.g., an SH-PTP1 sequence) and, particularly, a portion which includes the abnormality or abnormal region to be detected. A sample, such as a tumor or blood sample, is obtained from an individual. The sample is processed in a manner appropriate for rendering the nucleic acids (RNA and/or DNA) present in the sample available for hybridization. The processed sample is combined with the probe under conditions appropriate for hybridization to occur between the probe and a nucleic acid present in the sample. Hybridization can be detected using known techniques, for example, by use of a labeled probe or by detecting the probe in a second step (e.g., by enzymatic amplification). Suitable labels include, but are not limited to, radioisotopes, enzymes, and fluorescent labels.

Probes useful in this method include those which are sufficiently complementary to all or a portion of the SH-PTP1 gene to hybridize to the target region in 12p and be detected under the conditions used. A probe can be complementary to a region of a chromosome (e.g., 12p) or a gene (e.g., SH-PTP1) which includes the abnormal region or abnormality to be detected. For example, a probe can be complementary to a specific mutation(s) or alteration(s), the presence of which is associated with neoplastic disease. Hybridization with nucleic acids in a sample can be indicative of the presence of the mutation(s) or alteration(s) and of the neoplastic disease. The presence of an abnormality in a sample can also be revealed by a hybridization pattern which is different from that obtained from a normal sample.

Similar methods can also be used to detect alterations in the SH-PTP1 gene. Alternatively, it is possible to detect abnormalities in the SH-PTP1 gene using methods such as those described in Example 5. For example, single strand conformational polymorphism analysis (SSCP) or reverse transcription polymerase chain reaction (RT-PCR) can be used to examine the SH-PTP1 gene in DNA from a patient suspected of having an altered gene, such as an ALL patient, to determine whether a deletion or alteration of the SH-PTP1 gene exists. Primers such as those shown in FIG. 9 (SEQ ID NO.: 41–54) can be used to amplify regions of the SH-PTP1 gene. Alternatively, Western blot analysis can be conducted to determine whether an alteration in the expression or structure of the SH-PTP1 protein exists.

(b) Uses of 3B4-15 Homologs and 3B4-15-Related Genes

The similarity between SH-PTP2 and csw has interesting implications for SH-PTP2's role in signal transduction. Anterior and posterior structures in the developing Drosophila embryo are dependent upon the localized activation of the transmembrane tyrosine kinase torso, which ultimately activates transcription of the tailless and huckebein transcription factors (Bronner, G., et al., *Mech. of Devel.* 35:205–211 (1991), Pignoni, F., et al., *Cell* 62:151–163 (1990)). The torso signal is thought to be conducted via a phosphorylation cascade, at least one component of which is D-raf (reviewed in St. Johnston, D., et al., *Cell* 68:201–219 (1992)). csw functions to potentiate the D-raf signal (Perkins, L. A., et al., *Cell* 70:225–236 (1992)).

Analogously, in mammalian cells, the signal generated by many, if not all, GFs appears to be transmitted from receptgr tyrosine kinases to the nucleus via a pathway(s) dependent on c-Raf (and perhaps other Raf family members) (Rapp, U.R., *Oncogene* 6:495–500 (1991), Li, P., et al., *Cell* 64:479–482 (1991)). If SH-PTP2 is the mammalian csw homolog, it likely acts in proximity to Raf in signal transduction. Some workers have reported a direct interaction between Raf and activated GF receptors and/or that Raf is a substrate of receptor tyrosine kinases (App, H., et al., *Mol. Cell. Biol.* 11:913–919 (1991); Baccarini, M., et al., *EMBO J.* 9:3649–3657 (1990); Morrison, D. K., *Proc. Natl. Acad. Sci. USA* 85:8855–8859 (1988); Morrison, D. K., et al., *Cell* 58:648–657, (1989)). However, the extent to which Raf is found phosphorylated by and/or associated with different activated GF receptors varies substantially in different systems and in reports from different laboratories (reviewed in Rapp, U. R., *Oncogene* 6:495–500 (1991), Li, P., et al., *Cell* 64:479–82 (1991)). Moreover, unlike all other proteins that interact with activated GF receptors, Raf lacks SH2 domains.

One appealing hypothesis, based upon the genetic relationship between csw and D-raf, is that SH-PTP2 and Raf physically interact. SH-PTP2 could then act, at least in part, as an adapter molecule, bringing Raf to activated receptors. Since SH-PTP2 is a tyrosine phosphatase, such a model might account for the variability seen in Raf tyrosine phosphorylation and receptor association: slight variations in conditions could lead to variable tyrosyl dephosphorylation of Raf during extraction. SH-PTP2 might simultaneously function to dephosphorylate the activated receptor, thus terminating the GF signal. Alternative explanations are also possible. For example, there could be one or more other intervening signaling molecules between SH-PTP2 and Raf. Alternatively, the reported genetic interaction between csw and D-raf (Perkins, L. A., et al., *Cell* 70:225–236 (1992)) could imply that SH-PTP2 is a substrate for Raf and/or vice-versa.

Any model proposing an SH-PTP2/Raf interaction relies on the proposition that SH-PTP2 is the mammalian csw homolog. Despite their striking similarity, SH-PTP2 does differ from csw in its lack of an insert in its phosphatase domain. Although Perkins, et al. (*Cell* 70:225–236 (1992)) speculate that it may have a regulatory role, the function of the csw insert is unknown. Several csw transcripts exist, and their relative abundance varies at different stages of development (Perkins, L. A., et al., *Cell* 70:225–236 (1992)). These transcripts probably arise as a consequence of alternative splicing, but their precise genetic content has not yet been defined. It will be interesting to see whether all csw isoforms have a phosphatase insert. Similarly, it will be important to determine whether insert-containing isoforms of SH-PTP2 exist. The methods described herein can be used to isolate such isoforms; for example, SH-PTP2 or antibodies to its encoded protein can be used as probes. Even if SH-PTP2 is not the true csw homolog, the sequence features of the SH2-containing PTPs allow the definition of a consensus sequence for SH2 domains associated with PTPs (FIG. 7) and suggest straightforward PCR approaches towards the isolation of other SH2-containing PTPs.

(c) Uses of SH2 Homologs and SH2-Related Genes

PTPs may also act as anti-oncogenes or tumor suppressor genes. As such, overexpression of the phosphatase activity could lead to resistance to transformation mediated by a protein tyrosine kinase such as src. Activation or expression of the PTP could also be expected to reverse the transformed phenotype of a cell by an oncogenic tyrosine kinase. Introduction of the SH-PTP1 or SH-PTP2 gene into cells, in a manner such that it is expressed or overexpressed, could lead to resistance to transformation or to reversal of the transformed phenotype of a transformed cell.

In addition, the deletion or inactivation of a PTP could cause enhanced tyrosine phosphorylation, leading to transformation. In this situation, the PTP would act as a recessive oncogene in a cell. Reintroduction of an operative PTP into such a cell could restore the cell to normal, reduce or reverse the transformation process.

The present invention will now be illustrated by the following Examples, which are not intended to be limiting in any way.

EXAMPLE 1

Cloning of SH-PTP1 and Related Sequences

One strategy for isolation of novel protein tyrosine phosphatases is summarized in FIG. 1. As described below in more detail, two cDNA clones encoding novel PTPs were isolated from a rat megakaryocyte cDNA library using the strategy shown in FIG. 1. One of these clones (M1PTP; SEQ ID NO.: 1) was used as a probe to isolate a series of overlapping human cDNA clones defining the SH-PTP1 gene (SEQ ID NO.:5).

Degenerate Oligonucleotide-Based PCR and Library Screening

In order to isolate clones with both structural and functional homology to PTPs, degenerate oligomers were designed corresponding to amino acid sequences spanning conserved cysteine residues. The nucleotide sequence of the 20 base pair (bp) sense primer (SEQ ID NO.: 13) (SEQ ID NO.: 14) was based on the conserved amino acid sequence KCAEYWP, and incorporated several possible conservative substitutions. In particular, the sequences coded for all possible combinations of the peptide sequence KC[A, D or H] [Q or E] YWP. The oligonucleotides designed had a degeneracy of 512 and included an EcoRI site on the 5'-end. In the nucleotide sequences below, X indicates A, G, C or T at that position. [T/C] indicates a T or a C at that position of the oligonucleotide, for example.

```
     K       C      [A,D,H]   [Q/E]     Y      W      P
AA[A/G] TG[T/C] [G/C][A/C]X [G/C]A[A/G] TA[T/C] TGG CC-3'
(SEQ ID NO.: 13).
```

The 23 bp antisense primer (SEQ ID NO.: 14) was based on the non-coding strand corresponding to the conserved amino acid sequence VHCSAG[V/I] G. The set of oligonucleotides had a degeneracy of 8192, and a BamHI site on the 3'-end. (In the amino acid sequence below, the C-terminal residue is at the left.)

```
       G    [V/I]    G      A      S      C      H      V
5'-CC XA[C/T] XCC XGC XGA [G/A]CA [A/G]TG XAC
(SEQ ID NO.: 14).
```

A rat megakaryocyte cDNA library was amplified via liquid lysis and the bacteriophage were isolated. The PCR protocol included the following conditions:

| 900 ng of bacteriophage, 5 minutes at 100° | |
|---|---|
| denaturation | 1 minute at 94° |
| annealing | 1 minute at 45° |
| extension | 3 minutes at 720 for 30 cycles |
| final extension | 10 minutes at 72°. |

PCR products were analyzed by agarose gel electrophoresis on 1.0% agarose gels. Seven bands ranging in size from 100 to 1000 base pairs were consistently observed. The DNA in these bands was subcloned into vector pUC19 after digestion with EcoRI and BamHI, using standard techniques.

Consistent with the expected intraprimer distance of 300 bp, of all size inserts analyzed via sequencing, only inserts from the PCR products of 300 bp yielded clones with homology to PTPs. Twenty clones with 300 bp inserts were sequenced. Among these were 7 clones which had no homology to PTPs or other known cDNAs, 6 clones which were identified as rat CD45, and 1 clone which was subsequently reported as Leukocyte Common Antigen Related Phosphatase (LRP), a transmembrane PTP. Two additional clones of the twenty analyzed, M1PTP (3 isolates) and M2PTP (1 isolate), were identified as novel PTPs (see SEQ ID NO.: 2 and SEQ ID NO.: 4, respectively) based on sequence homology. The genes corresponding to the rat megakaryocyte M1PTP and M2PTP clones were initially termed M1PTP (see SEQ ID NO.: 1) and M2PTP (see SEQ ID NO.: 3), respectively.

The 300 bp fragments from M1PTP (see SEQ ID NO.: 1) and M2PTP (SEQ ID NO.: 3) were labeled and used as probes to screen a rat megakaryocyte cDNA library derived from elutriated megakaryocyte poly A RNA. A total of 1×10⁶ plaques were screened for each clone, with subsequent isolates plaque purified and subcloned into pUC19. Rat cDNA clones obtained from the library using the M1PTP PCR probe were sequenced using λgt11 sequencing primers, as well as specific oligomers designed from sequence data from both 5' and 3' directions. The resulting sequence is designated SEQ ID NO.: 1.

Characterization of M1PTP and M2PTP

M1PTP and M2PTP were characterized according to message size; tissue expression in normal and busulfan-induced pancytopenic rats, to eliminate white blood cell/ platelet contamination (tissues analyzed included: brain, lung, heart, kidney, adrenal, muscle, skeletal muscle, spleen, and liver); expression in the human erythroleukemia cell line (HEL), known for its megakaryocytic features; inducibility of message in response to a non-specific differentiating agent (DMSO) in HEL cells; PTP homology via computer analysis; and Southern blot analysis.

For Northern blot analysis, RNA was prepared from whole tissues via the cold phenol method, fractionated by electrophoresis on denaturing formaldehyde gels, transferred to Nytran membranes, and hybridized to a random-primer generated $^{32}$P-labeled probes in Church-Gilbert buffer. The $^{32}$P-labeled probes used to probe Northern blots include a 1745 bp fragment encompassing the coding sequence of M1PTP and a 300 bp fragment from the PTP homology region of M2PTP.

Of the two novel PTPs, the first, designated M1PTP, encodes a 3.0 kb message. Although M1PTP mRNA was detected in RNA isolated from other tissues (e.g., kidney, spleen, liver), M1PTP expression appeared to occur predominantly in the lung and megakaryocytes. M1PTP mRNA was also detected in RNA isolated from HEL cells, which have megakaryocyte features. Further, expression in HEL cells was shown to be inducible by treatment with DMSO. M1PTP displayed strong sequence similarity at the nucleotide level (56%) to rat and human LAR, LRP, LCA and PTP1B across the first phosphatase domain.

The second clone, M2PTP, encodes an 8.0 kb message, with expression largely restricted to megakaryocytes. It is possible that mRNA detected in RNA from other tissue samples is due to contamination by platelets, and that both M1PTP and M2PTP expression is highly tissue specific.

Isolation of Human M1PTP

The M1PTP rat cDNA clone isolated (SEQ ID NO.: 1) did not appear to be a full-length clone. The sequence ended in frame with no initiator methionine (see SEQ ID NO.: 1 and SEQ ID NO.: 2). Furthermore, the length of the messenger RNA detected on Northern blots indicated that the gene was larger than that encoded by the isolated clone. Because the M1PTP gene was highly expressed in lung and HEL cells as determined by Northern analysis, both human lung (λgt11 library; Clontech) and human erythroleukemia cell line (HEL; λgt11 library from Dr. M. Ponzc, University of Pennsylvania School of Medicine) cDNA libraries were probed from M1PTP clones.

Using a 1745 bp fragment (see SEQ ID NO.: 1) which spans the M1PTP coding sequence form the rat M1PTP cDNA clone as a probe, a total of five overlapping cDNA clones were isolated. Three of these clones were isolated from the lung library and 2 clones were isolated from the HEL library. The nucleotide sequence encoded by the clones from the two sources appear to be identical, and the sequence of the full-length composite gene is shown in FIG. 2. The human gene, which was isolated using the rat M1PTP gene fragment as a probe, is designated SH-PTP1 (SEQ ID NO.: 5). An additional sequence was isolated from the library obtained from the HEL cell line. This variant form lacks the AG at positions 1868 and 1869 of SH-PTP1 (SEQ ID NO.: 5) and was designated SEQ ID NO.: 7.

Southern blot analysis of human genomic DNA was carried out using a fragment comprising the full-length human SH-PTP1 coding sequence as a probe. Although genomic DNA was digested with seven different restriction enzymes (PvuII, BglI, BglII, XbaI, DraI, PstI and EcoRI), hybridization to only one to approximately four bands was observed under stringent conditions. This analysis suggested that SH-PTP1 is a single-copy gene.

Total RNA was prepared from rat brain, heart, lung, liver, kidney platelets, and elutriated megakaryocytes (Berkow et al., *J. Lab Clin. Med.* 103:811 (1984)) by the guanidinium isothiocyanate method, electrophoresed on 1% agarose/2.2M formaldehyde gels, transferred to nylon membranes, and hybridized with randomly labeled SH-PTP probe. Hybridizations were carried out in Church-Gilbert buffer (Church and Gilbert, *Proc. Natl. Acad. Sci. USA* 81:1991 (1984)). Ethidium bromide staining of the gel revealed equal loading of RNA. The Northern analysis of total RNA revealed that SH-PTP1 is expressed at high levels in megakaryocytes and platelets, and also in lung. SH-PTP1 is also expressed in primary tracheobronchial epithelial cells. Expression in other tissues (e.g., rat brain, heart, liver, kidney) was substantially lower. Absent or low level signals were also observed in adrenal, stomach, diaphragm, and skeletal muscle. Further characterization of SH-PTP1 indicated that it is a phosphoprotein having a-molecular weight of 66,000.

Tyrosine Phosphatase Activity of SH-PTP1

(a) Preparation of Fusion Proteins.

The SH-PTP1 coding sequence was introduced into the bacterial expression vector pGEX-2T (Pharmacia; Smith and Johnson, *Gene* 67:31–40 (1988)). An SH-PTP1 EcoRI fragment was inserted into vector pGEX-2T which had been cleaved with EcoRI to generate a fusion protein. (The variant SH-PTP1 was used in this assay; SEQ ID NO.: 7). Several recombinant clones were obtained. The fusion protein consisted of glutathione S-transferase plus a 9 amino acid spacer fused to the complete SH-PTP1 protein sequence of SEQ ID NO.: 7, and is referred to as GEX-SH phosphatase (GEX-SH-PTP).

For expression of GEX fusion proteins, freshly diluted overnight cultures were induced at mid-log phase with 1 mM isopropyl β-thiogalactopyranoside. Lysates were prepared from 1 ml of induced culture, by resuspending in 150 μl of phosphate buffered saline containing 1% NP40 and sonicating (0° C.) for 3 minutes. Parallel cultures expressing the parental GEX-2T vector, which products glutathione S-transferase alone, were treated similarly.

(b) phosphatase Activity of GEX-Fusions.

Figure 4A:
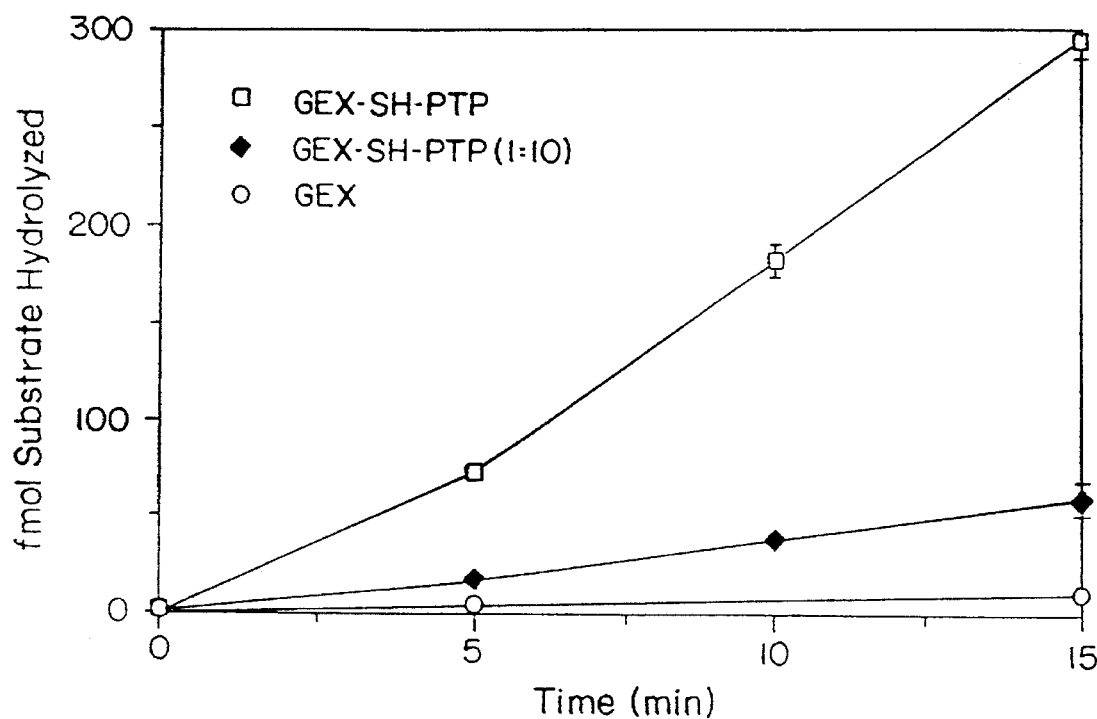
FIGS. 4A and 4B are a pair of graphs illustrating the time course of dephosphorylation of model substrates Raytide (FIG. 4A) and myelin basic protein (MBP.
Figure 4B:
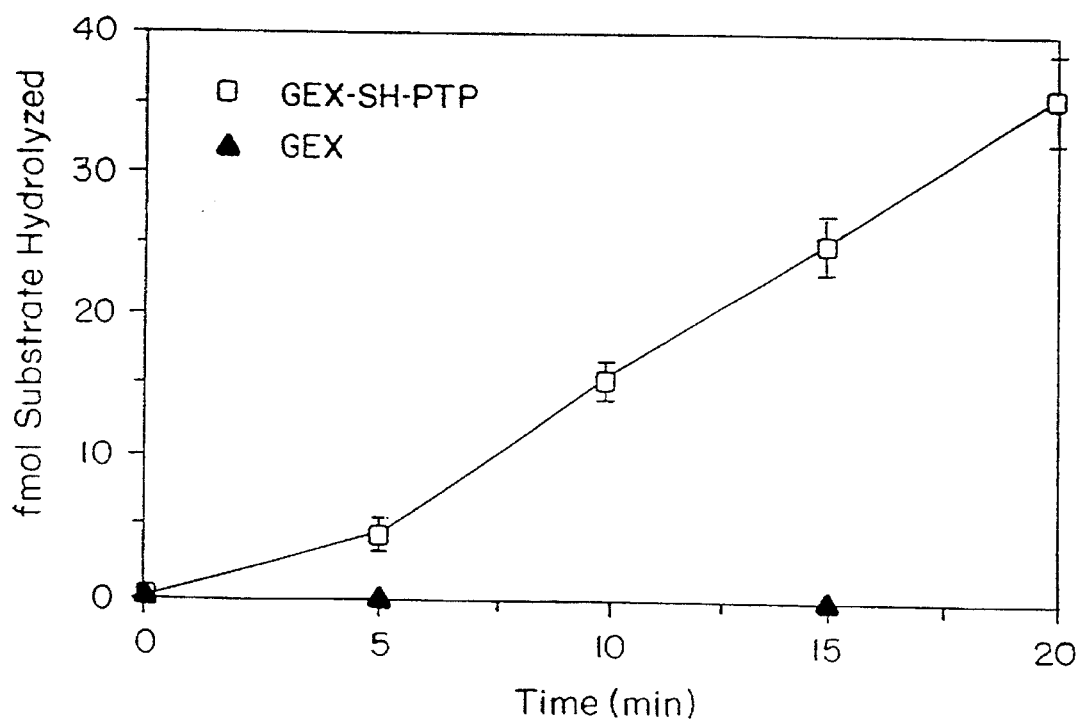

Phosphatase activity against two model substrates, the synthetic peptide Raytide (FIG. 4A), and myelin basic protein (MBP; FIG. 4B), was determined. Raytide (Oncogene Sciences) and myelin basic protein (Sigma Chemical Co., St. Louis, Mo.) were phosphorylated on their unique tyrosines using recombinant p43 v-$^{ab1}$ protein (Oncogene Sciences) and γ$^{32}$P-ATP (200 mCi), and the product was precipitated and washed as described, (Streuli, M. et al., *EMBO J.* 9:2399–2407 (1990)). Typical specific activities obtained were from 1 to 2×10$^5$ cpm/pmol, representing 1 to 2% incorporation (Raytide) and 5 to 10% incorporation (MBP).

Phosphatase assays (in 25 mM imidazole, pH 7.2, 1 mg/ml BSA, 10 mM dithiothreitol, 100 nM phosphorylated substrate, and bacterial protein) were incubated at 30° C. for the indicated times. Dephosphorylation was measured as described (Streuli, M. et al., *EMBO J.* 9:2399–2407 (1990)).

Equal amounts of total protein (500 ng for GEX and GEX-SH-PTP; 50 ng for "GEX-SH-PTP 1:10") isolated from *E. coli* expressing glutathione transferase (GEX) or the glutathione transferase-SH-PTP1 fusion (GEX-SH-PTP) were incubated with the indicated substrate. At the indicated times (FIG. 4), data points were taken in triplicate and assayed for release of $^{32}$P using the charcoal binding assay. The mean ± SEM is indicated for each time point. Lysates from cells expressing GEX-SH phosphatase displayed substantially increased phosphatase activity against the two model substrates as compared with control lysates expressing glutathione-S-transferase from the parental GEX-2T vector (FIG. 4A and 4B). However, there was no significant activity against the serine phosphorylated model substrate Kemptide (data not shown), consistent with a specificity for tyrosine. Similar results were obtained with fusion proteins which were partially purified on glutathione-agarose beads (Pharmacia; Smith and Johnson, *Gene* 67:31–40 (1988)).

Figure 5:
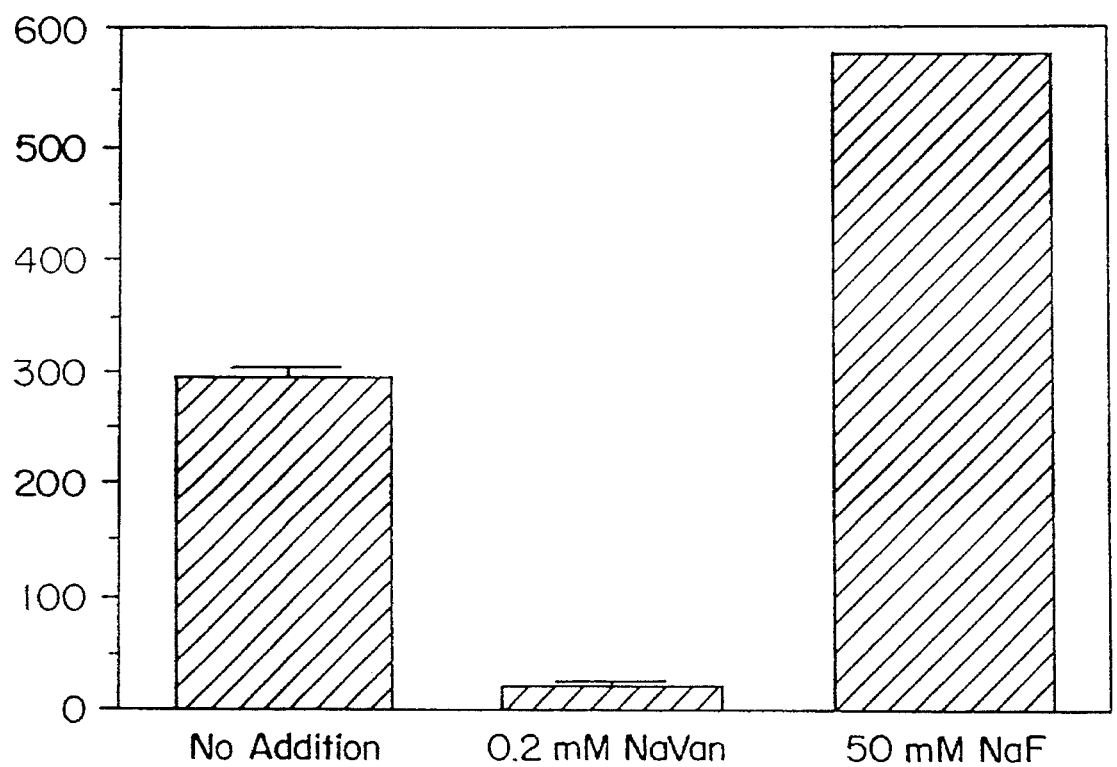
FIG. 5 is a histogram illustrating the effect of phosphatase inhibitors on GEX-SH-PTP activity. Phosphatase assays were carried out in the presence or absence of either sodium orthovanadate (NaVan; 200 mM) or sodium fluoride (NaF; 50 mM).

The effect of phosphatase inhibitors on GEX-SH-PTPase activity was also determined using the phosphatase assay (FIG. 5). Phosphatase assays were carried out as described above in the presence or absence of either sodium orthovanadate (200 mM) or sodium fluoride (50 mM). Phosphate release was measured after fifteen minutes of incubation. As predicted for a tyrosine phosphatase, GEX-SH-PTPase activity was strongly inhibited by sodium orthovanadate, but not by sodium fluoride (FIG. 5). In fact, sodium fluoride appeared to be moderately stimulatory.

An Inactive Mutant SH-PTP1

A cysteine residue located in the "VHCSAG" homology sequence of protein tyrosine phosphatases is located at the active site of the enzyme. A mutation of the cysteine to serine has been shown to abolish phosphatase activity in other PTPs. Using the polymerase chain reaction, SH-PTP1 (SEQ ID NO.: 5) was mutated as follows:

```
5'-CAC TGC AGC ...  changed to  5'-CAC TCC AGC
   His Cys Ser                     His Ser Ser
```

This nucleotide change replaces cysteine 453 (Cys) of SH-PTP1, located in the VHCSAG sequence of the encoded protein (bold letters in FIG. 2, with nucleotide sequence in capital letters), with serine 453 (Ser) to encode a VHSSAG sequence. The altered SH-PTP1 nucleotide sequence encoding the "VHSSAG mutant" is designated SH-PTP1 (S453) The resulting "VHSSAG mutant" an SH-PTP1 protein having a Cyc 453 to Ser 453 mutation, was then expressed as a fusion protein in bacteria as described above, and was found to be inactive as a phosphatase.

EXAMPLE 2

Chromosomal Localization of SH-PTP1

DNA was prepared from 32 somatic cell hybrids involving 15 unrelated human and 4 mouse cell lines (Shows et al., *Cytogenet. Cell Genet.* 21:99–104 (1978); Shows, et al., in: *Advances in Human Genetics,* Hattis, H and K. Hirschhorn, Eds., Vol. 12, (Plenum Press: New York, London), pp. 341–452 (1982); Shows et al., *Somat. Cell Mol. Gen.* 10:315–318 (1984)). The hybrids were characterized by karyotyping, and with mapped enzyme markers (Shows et al., *Cytogenet. Cell Genet.* 21:99–104 (1978); Shows et al. In: *Advances in Human Genetics.* Hattis, H and K. Hirschhorn, Eds., Vol. 12, (Plenum Press: New York, London), pp. 341–452 (1982); Shows, T. In: *Isozymes: Current Topics in Biological and Medical Research,* Rattazzi, M. C. et al., Eds Vol. 10, (A. R. Liss, New York) pp. 323–330 (1983)). The properties of the hybrids are summarized in Table 1. The chromosome content of each hybrid is indicated. A "t" in Table 1 indicates that only the translocation indicated in the column labelled "Translocations" is present, and that no intact chromosome is present.

Bands corresponding to human and mouse SH-PTP1 can easily be distinguished on Southern blots of EcoRI-digested DNA. Accordingly, hybrid cell DNA was digested with EcoRI, fractionated by agarose gel electrophoresis, and transferred to Nylon membranes for Southern blotting as described (Naylor et al., *J. Exp. Med.* 57:1020–1027 (1983)). The 2.2 kb full length SH-PTP1 cDNA was labelled with $\alpha^{32}$P-dCTP using the random primers method (Feinberg and Vogelstein, *Anal. Biochem.* 132:6–13 (1983)) and hybridized to the blot. Each hybrid DNA was scored for the presence (+) or absence (−) or human SH-PTP1 bands. The results of this analysis were compared against the known presence or absence of specific human chromosomes in each hybrid. A 0% discordance indicates matched segregation of the probe with a particular chromosome. As shown in the Table, there was 0% discordance between the presence of human SH-PTP1 bands by Southern analysis and the presence of human chromosome 12 in a given hybrid. Thus, SH-PTP1 maps to chromosome 12 by somatic cell hybrid analysis.

TABLE 1

Segregation of SHPTP1 with Human Chromosomes in EcoRI Digested Human-Mouse Cell Hybrid DNA

| DNA# HYBRID | SHPTP1 | 1 | 2 | 3 | 4 | 5 | 6 | 7 | 8 | 9 | 10 | 11 | 12 | 13 | 14 | 15 | 16 | 17 | 18 | 19 | 20 | 21 | 22 | X | Translocations |
|---|---|---|---|---|---|---|---|---|---|---|---|---|---|---|---|---|---|---|---|---|---|---|---|---|---|
| 660 ATR-13 | + | + | + | + | + | + | + | + | + | + | + | − | + | + | + | + | + | + | + | − | − | + | t |  | 5/X |
| 233 | − | − | + | − | − | − | − | + | + | − | − | − | − | + | + | − | − | + | − | − | − | − | − | − |  |
| DUA-3BSAGA | − | − | + | − | − | − | − | + | + | − | − | − | − | + | + | − | − | + | − | − | − | − | − | − |  |
| 197 | − | − | − | + | − | + | − | − | − | − | − | + | − | − | + | − | − | + | + | − | − | + | − | − |  |
| DUA-5BSAGA 859 DUA-6 | − | − | + | − | + | + | − | − | − | − | − | − | − | − | − | + | − | − | + | + | − | − | − | + |  |
| 186 DUM-13 | + | + | + | + | − | + | + | + | − | − | + | + | + | − | + | t | + | + | + | + | + | + | + | t | X/15, 15/X |
| 1185 GAR-1 | + | − | − | + | − | + | − | − | + | − | + | − | + | + | − | + | + | − | − | − | + | − | − | + |  |
| 389 JSR-2 | − | − | − | + | + | − | − | + | − | − | − | − | − | + | + | − | − | − | − | − | − | − | − | + |  |
| 402 JSR-14 | + | − | + | + | + | + | + | − | − | − | − | − | + | + | − | − | − | + | − | − | + | + | − | + |  |
| 187 JWR-26C | + | t | + | + | + | + | + | + | − | + | + | + | + | − | + | + | + | + | − | + | + | − | + |  | 1/2 |
| 830 KER-3 | − | − | − | − | − | − | − | − | − | − | − | + | − | + | + | − | + | − | − | − | − | − | − | + |  |
| 1146 NSL-9 | + | − | − | − | − | + | − | − | + | t | + | − | + | + | − | + | + | + | + | − | + | + | + | − | 17/9 |
| 192 NSL-16 | + | − | − | + | + | + | − | + | + | t | + | − | + | − | + | + | + | + | − | + | + | − | − |  | 17/9 |
| 42 REW-11 | + | − | − | − | + | − | − | + | − | − | − | + | + | + | − | + | + | − | − | − | + | + | + | + |  |
| 184 REX-11BSAgB | − | − | − | + | − | − | − | − | − | − | + | − | − | − | + | − | − | − | + | − | − | − | − | − |  |
| 254 | − | − | − | − | + | − | − | − | − | − | − | + | − | − | − | + | + | − | − | − | + | − | − | − | t | t 22/X |

TABLE 1-continued

Segregation of SHPTP1 with Human Chromosomes in EcoRI Digested Human-Mouse Cell Hybrid DNA

| DNA# HYBRID | SHPTP1 | \multicolumn{23}{c}{Human Chromosomes} | Trans-lo-cations |
|---|---|---|---|---|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | X | |
| REX-11BSHF 394 REX-26 | + | + | + | + | + | − | − | + | + | + | + | + | + | − | + | − | + | + | + | + | − | + | t | t | 22/X |
| 1162 RSR-3 | − | − | − | − | + | − | − | + | − | − | + | + | − | − | + | + | + | + | − | − | − | + | − | + | |
| 390 SIR-11 | − | − | − | − | − | − | − | + | − | − | − | − | − | + | − | − | − | − | − | − | − | + | + | + | |
| 643 TSL-1 | − | − | + | + | + | − | − | − | − | − | + | + | − | + | − | − | + | + | + | − | + | + | − | − | |
| 644 TSL-2 | + | − | + | t | − | + | + | − | + | − | + | − | + | − | + | − | − | t | + | − | + | + | − | + | 17/3 |
| 395 VTL-6 | − | − | + | − | − | − | + | + | + | − | + | + | − | − | − | + | − | + | − | + | + | + | + | − | |
| 407 VTL-17 | − | − | − | − | − | − | + | − | + | − | − | + | + | − | + | + | + | − | + | − | − | + | + | − | − | |
| 212 WIL-2 | + | − | − | − | − | − | − | − | + | − | + | − | + | − | − | + | − | + | − | − | − | + | − | + | |
| 425 WIL-6 | − | − | + | − | + | + | + | + | + | − | + | + | − | − | − | − | − | + | − | + | + | + | − | + | |
| 424 WIL-8X | + | − | − | + | + | + | − | + | + | − | + | + | + | − | + | − | − | + | + | + | + | + | − | + | |
| 347 WIL-14 | + | + | − | + | − | + | − | + | + | − | + | − | + | − | + | + | − | + | − | − | − | − | − | + | |
| 25 WIL-15 | + | − | + | + | + | − | + | + | − | − | + | + | + | + | + | + | − | + | + | − | + | + | − | + | |
| 534 XOL-6 | + | t | − | − | − | + | + | + | − | − | + | + | + | − | + | − | − | + | − | + | + | − | + | t | 1/X |
| 555 XOL-13 | + | t | − | − | + | + | − | + | − | − | + | + | + | − | − | − | − | + | − | − | + | − | − | + | X/1 |
| 1107 XOL-21 | + | − | − | + | − | − | − | t | + | + | + | + | + | − | + | − | − | + | + | − | + | − | − | + | ISO7p |
| 332 XTR-2 | + | − | − | t | − | + | − | − | + | − | + | − | + | + | + | − | − | − | + | − | + | + | − | t | 3/X |
| 57 XTR-3BSAgB | + | − | − | t | − | − | − | − | − | + | t | − | + | − | − | − | − | − | − | + | + | − | t | 3/X, 10q- |
| Chromosome | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | X | |
| Concordant # of Hybrids | (+/+) | 4 | 7 | 11 | 9 | 13 | 7 | 11 | 11 | 5 | 16 | 9 | 19 | 7 | 13 | 10 | 8 | 14 | 11 | 5 | 15 | 13 | 5 | 11 | |
| | (−/−) | 13 | 8 | 8 | 8 | 9 | 11 | 6 | 10 | 13 | 6 | 6 | 13 | 7 | 4 | 10 | 10 | 6 | 8 | 10 | 9 | 6 | 10 | 6 | |
| Discordant # of Hybrids | (+/−) | 12 | 12 | 5 | 10 | 6 | 12 | 7 | 8 | 12 | 2 | 10 | 0 | 12 | 6 | 8 | 11 | 4 | 8 | 14 | 4 | 6 | 13 | 2 | |
| | (−/+) | 0 | 5 | 5 | 5 | 4 | 2 | 7 | 3 | 0 | 7 | 7 | 0 | 6 | 9 | 3 | 3 | 7 | 5 | 3 | 4 | 7 | 2 | 6 | |
| % Discordancy | | 41 | 53 | 34 | 47 | 31 | 44 | 45 | 34 | 40 | 29 | 53 | 0 | 56 | 47 | 35 | 44 | 35 | 41 | 53 | 25 | 41 | 50 | 32 | |

To determine regional localization on chromosome 12, fluorescent in situ hybridization (FISH) was performed on metaphase chromosomes. Chromosome spreads were prepared from 5-bromodeoxyuridine-synchronized lymphocyte cultures. Full length SH-PTP1 cDNA insert was biotinylated and hybridized to the chromosome spreads. Following appropriate washing, hybridization was detected by reaction with fluorescein-conjugated avidin (Vector Labs). Chromosome identification was achieved by means of Q banding (DAPI counterstaining) and R banding (propidium iodine counterstaining) (Cherif et al., *Hum. Genet.* 81:358–362 (1989); Fan et al., *Proc. Natl. Acad. Sci. USA* 87:6223–6227 (1990)). Slides were evaluated using a Nikon fluorescence microscope.

Figure 6C:
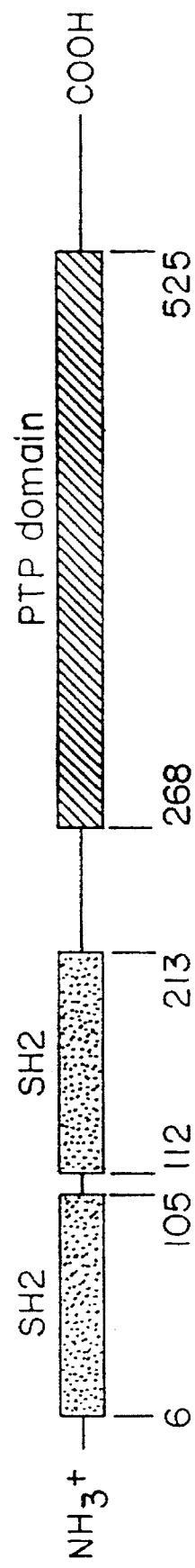
FIG. 6C is a schematic diagram of the predicted protein structure of SH-PTP2. The relative positions of the two SH2 domains and the PTP domain are indicated, corresponding to their predicted amino acid sequence.

Thirty metaphases were examined. A fluorescent signal was detected at 12p13 on both chromatids of at least a single chromosome 12 in 26 of the 30 metaphase spreads examined (86%; FIG. 6). In 2 of the 26 spreads, signals were detected at band p13 on both chromatids of both chromosomes 12, whereas 6 of the 26 spreads had an additional single signal on one chromatid of the other chromosome 12. No other chromosome displayed significant hybridization. These data clearly localize SH-PTP1 to 12p13.

EXAMPLE 3

Cloning of SH-PTP2 and Related Sequences

Degenerate Oligonucleotide Based PCR and Library Screening

Brain contains numerous biochemically distinct tyrosine phosphatase activities (Jones, S. W. et al., *J. Biol. Chem.* 264:7747–7753 (1989)). For this reason, degenerate mixed oligonucleotides (sense, AA(A/G)TG(C/T) (C/G) (A/C)X(C/G)A(A/G)TA(C/T)TGGCC (SEQ ID NO.: 13); antisense, CCXA(C/T)XCCXGCXGA(A/G)CA(A/G)T- GXAC (SEQ ID NO.: 14)) to conserved sequences in the catalytic domains of known PTPs, including SH-PTP1, were synthesized (Plutzky, J., et al. *Proc. Natl. Acad. USA* 89:1123–1127 (1992)). These oligonucleotides were used to prime PCRs in which 100 ng total bacteriophage DNA from a λgt11 rat brain cDNA library (D. Chikaraishi, Tufts University School of Medicine) were used as template. The conditions for amplification were as described previously (Plutzky, J., et al. *Proc. Natl. Acad. USA* 89:1123–1127 (1992)), except that primer annealing was carried out at 37° C. for three cycles followed by 50° C. for 27 cycles.

PCR fragments of approximately the same size (~300 base pairs) as that generated using as template the non-transmembrane PTP, PTP-1B (Chernoff, J., et al., *Proc. Natl. Acad. Sci.* 87:2735–2739 (1990)), were excised and subcloned into Bam HI-EcoRI-linearized pBlueScript KS (Stratagene). Of the initial 42 clones sequenced, all were derived from the lambda phage vector or elongation factor 1α. Sequenced clones not containing protein sequences conserved among known PTPs were pooled, labeled by the random primers method (Feinberg, et al., *Anal. Biochem.* 132:6–13 (1983)), and used to negatively select the remaining clones by colony hybridization. Of the 48 clones that failed to hybridize to these pooled inserts, over 50% contained inserts with strong similarity to PTPs. Nearly all represented rat homologs of known PTPs, including LRP (Matthews, et al., *Proc. Natl. Acad. Sci. USA* 87:4444–4448 (1990)), LAR (Streuli, M., et al., *J. Exp. Med.* 168:1523–1530 (1988)), and HPTPδ (Krueger. M. X., et al., *EMBO J.* 9:3241–3252 (1990)). However, one novel insert, 3B4-15, was obtained (SEQ. ID NO.: 9, SEQ ID NO.: 10). This fragment was excised, radiolabelled as above, and used to screen the rat brain cDNA library; however, all attempts to obtain a full length clone from this library were unsuccessful. Northern blotting of RNA from various rat tissues (data not shown) revealed widespread expression, including high levels of expression in lung and brain. Based on these results, we used a partial rat brain cDNA to screen a λgt11 human lung cDNA library (Clonetech). Again, full length cDNAs could not be obtained. A partial cDNA clone from the human lung library was used to screen a λZap II human fetal brain cDNA library (Stratagene). This library yielded several overlapping partial cDNA clones as well as one clone containing the complete coding region for a novel PTP gene, which was termed SH-PTP2. Positive clones were plaque-purified and cDNA inserts subcloned into plasmid vectors (for λgt11 clones) or rescued by single-strand helper phage (for λZap II clones). Rat and human cDNA clones corresponding to the initial 3B4-15 fragment, hereafter described as SH-PTP2 clones, included a partial rat brain cDNA, several partial human lung and fetal brain cDNAs, and one human fetal brain cDNA that contains the complete coding region of SH-PTP2.

Characterization of 3B4-15 and SH-PTP2

All phage inserts were sequenced on both strands using oligonucleotide primers by the dideoxy chain termination method (Sanger, F., et al., *Proc. Natl. Acad. Sci. USA* 74:5463–5467 (1977)) with Sequenase (USB) or with fluorescent dye technology and Taq polymerase on a 373A DNA Sequencer (Applied Biosystems, Inc.). DNA and deduced amino acid sequences were analyzed using BLAST (Altschul, S.F., et al., *J. Mol. Biol.* 215:403–410 (1990)) or the University of Wisconsin GCG programs (FASTA, TFASTA, GAP, BESTFIT, and PILEUP) (Devereux, J., et al., *Nucl. Acids. Res.* 12:387–395 (1984)).

FIG. 6B shows the nucleic acid and deduced amino acid sequence encompassing the coding region of human SH-PTP2 (SEQ. ID NO.: 11, 12). At nucleotide 114 is a good consensus sequence (AACATGA) for translation initiation (Kozak, M., *Cell* 44:283–292 (1986)); this sequence is preceded by in-frame stop codons, making it highly likely that this is the bona fide translational start site. This is followed by a single open reading frame which encodes a 593 amino acid protein with a predicted molecular weight of 68 kD, and is followed by a 3' untranslated region with stop codons in all three frames. The remainder of the large 5' and 3' untranslated regions have not yet been characterized.

Analyses of the predicted amino acid sequence reveal several interesting features. SH-PTP2, like other non-transmembrane PTPs, contains a single tyrosine phosphatase domain (aas 268–525). The cysteine (aa 459) previously shown to be essential for catalysis (Streuli, M., et al., *Proc. Natl. Acad. Sci. USA* 86:8698–8702 (1989)) and other residues common to all members of the PTP family are present (indicated by asterisks in FIG. 6A). N-terminal to the PTP domain are two SH2 domains (aas 6–105 and aas 112–218). Both possess the three invariant residues found in all SH2 domains (Koch, C., et al., *Science* 252:668–674 (1991)), indicated by • in FIG. 2. Only two of the three conserved basic amino acids believed to participate in interactions with phosphotyrosyl residues (Koch, C. et al., *Science* 252:668–674 (1991) are present (indicated by + in FIG. 7). Interestingly, this is also true for PTP1 and csw. SH-PTP2 has several potential phosphorylation sites for serine/threonine and tyrosine kinases (Kennelly, P. J., et al., *J. Biol. Chem.* 266:15555–15558 (1991), Kemp, B. E., et al., *TIBS* 15:342–346 (1990)). The absence of an apparent nuclear localization signal (Newport,, J., et al., *Annu. Rev. Biochem.* 56:535–565 (1987), Dingwall, C., et al., *Annu. Rev. Cell Biol.* 2:367–390 (1986)) and the lack of any significant hydrophobic region, as indicated by Kyte-Doolittle hydropathy analysis (Kyte, J., et al., *J. Mol. Biol.* 157:105–132 (1982)) make it likely that SH-PTP2 is a cytosolic protein, like SH-PTP1.

Within the PTP family, human SH-PTP2 (SEQ ID NO.: 16) is most similar to Drosophila csw (SEQ ID NO.: 17) (FIG. 6A and Table 2). Unlike other PTP family members, csw contains an insert within its phosphatase domain (Perkins, L. A., et al., *Cell* 70:225–236 (1992)); SH-PTP2 lacks such an insert. When the PTP domain of SH-PTP2 is compared to csw without its insert, the two are 63% identical. Moreover, the three SH2-containing PTPs, human SH-PTP2 (SEQ ID NO.: 16), csw (SEQ ID NO.: 17), and SH-PTP1 (SEQ ID NO.: 18), are substantially more similar to each other than to any other member of the PTP family (<45%), such as human RPTµ (SEQ ID NO.: 19), HPTPβ (SEQ ID NO.: 20), human LAR (SEQ ID NO.: 21), HPTPδ (SEQ ID NO.: 22), and DLAR (SEQ ID NO.: 23), suggesting the existence of a discrete subfamily of PTPs that contain SH2 domains.

There is also striking sequence similarity between the two SH2 domains of the SH2-containing PTPs (FIG. 7 (SEQ ID NO.: 24 and NO.: 27) and Table 2). As is the case for the phosphatase domain, the SH2 domains of SH-PTP2 (SEQ ID NO. 24 and NO.: 27) are more similar to csw (SEQ ID NO.: 25 and NO.: 28) (approximately 76%) than to SH-PTP1 (SEQ ID NO.: 26 and NO.: 29) (52–63%); they are much less similar to any other SH2-containing protein, such as human fer (SEQ ID NO.: 30), bovine GAP (SEQ ID NO.: 31), mouse fgr (SEQ ID NO.: 32 and NO.: 35), human Nck (SEQ ID NO.: 33 and NO.: 40), hydra stk (SEQ ID NO.: 34), chicken yes (SEQ ID NO.: 36), human fyn (SEQ ID NO.: 37), mouse lsk (SEQ ID NO.: 38), mouse blk (SEQ ID NO.: 39) (<40%). Taken together, these data suggest the existence of a discrete subfamily of SH2 domains found primarily in SH2-containing PTPs. Moreover, the similarity between SH-PTP2 and csw extends over the entire sequence of both molecules; overall, the protein sequences of SH-PTP2 and csw are 62% identical. This remarkable similarity between human SH-PTP2 and Drosophila csw strongly suggests that SH-PTP2 is the human csw homolog.

TABLE 2

| Sequence similarity between SH2-containing PTP family members. | | | |
|---|---|---|---|
| | SH-PTP2 | csw | SH-PTP1 |
| PTP domain | | | |
| SH-PTP2 | — | 62.5 | 60.8 |
| csw | | — | 57.9 |
| SH-PTP1 | | | — |
| N-terminal SH2 domain | | | |
| SH-PTP2 | — | 75.8 | 63.0 |
| csw | | — | 59.6 |
| SH-PTP1 | | | — |
| C-terminal SH2 domain | | | |
| SH-PTP2 | — | 76.1 | 52.0 |
| csw | | — | 46.1 |
| SH-PTP1 | | | — |
| Overall | | | |
| SH-PTP2 | — | 63.2 | 54.7 |
| csw | | — | 50.1 |
| SH-PTP1 | | | — |

The SH2 and phosphatase domains of each protein were compared to one another using GAP (Devereux, J. et al., *Nucleic Acids Res.* 12:387–395 (1984)), and the percent identity noted. Comparisons were made to csw without its phosphatase insert.

Tyrosine Phosphatase Activity of SH-PTP2

(a) Preparation of Fusion Proteins

To determine whether SH-PTP2 possesses protein tyrosine phosphatase activity when expressed in bacteria, a 1.6 kb partial SH-PTP2 cDNA was subcloned as an EcoRI fragment into pGEX-3X (Pharmacia). This construct encodes a 639 amino acid protein (GST-SHPTP2) in which glutathione-Stransferase sequences (GST) are fused to amino acids 186 to 593 of SH-PTP2. This results in the expression of a fusion protein (GST-SHPTP2) with a molecular weight of approximately 70 kd (data not shown), which can be affinity purified on glutathione-agarose beads. Both GST and GST-SHPTP2 were introduced into DH5α hosts. For expression of these proteins, overnight cultures were diluted 1:50 and permitted to grow for one hour, at which time the cells were induced with 0.1 mM isopropyl β-thiogalactopyranoside (IPTG). After four hours, lysates were prepared from one ml of induced culture. Briefly, bacterial pellets were washed with 150 μL of STE (25 mM Tris, pH 8.0, 150 mM NaCl, 1 mM EDTA), lysed in 150 μl NP-40 lysis buffer (50 mM Tris, pH 8.0, 150 mM NaCl, 1% NP-40) with protease inhibitors (1 μg/ml antipain, 1 μg/ml aprotinin, 10 μg/ml leupeptin, 1 μg/ml pepstatin A, 20 μg/ml PMSF), and sonicated on ice for three minutes. Lysates were clarified by centrifugation at 10,000×g for five minutes at 4° C. before use. Protein concentrations were determined by BCA assay (Pierce). For affinity purification of GST and GST-SH-PTP2, 80 μl of the soluble lysate were adjusted to 2% Triton X-100 and incubated with 30 μl of a 50% (v/v) solution of glutathione agarose beads (Sigma) for 30 minutes at room temperature. Beads were washed three times with STE before use.

(b) Phosphatase Activity of GEX Fusions

Figure 8:
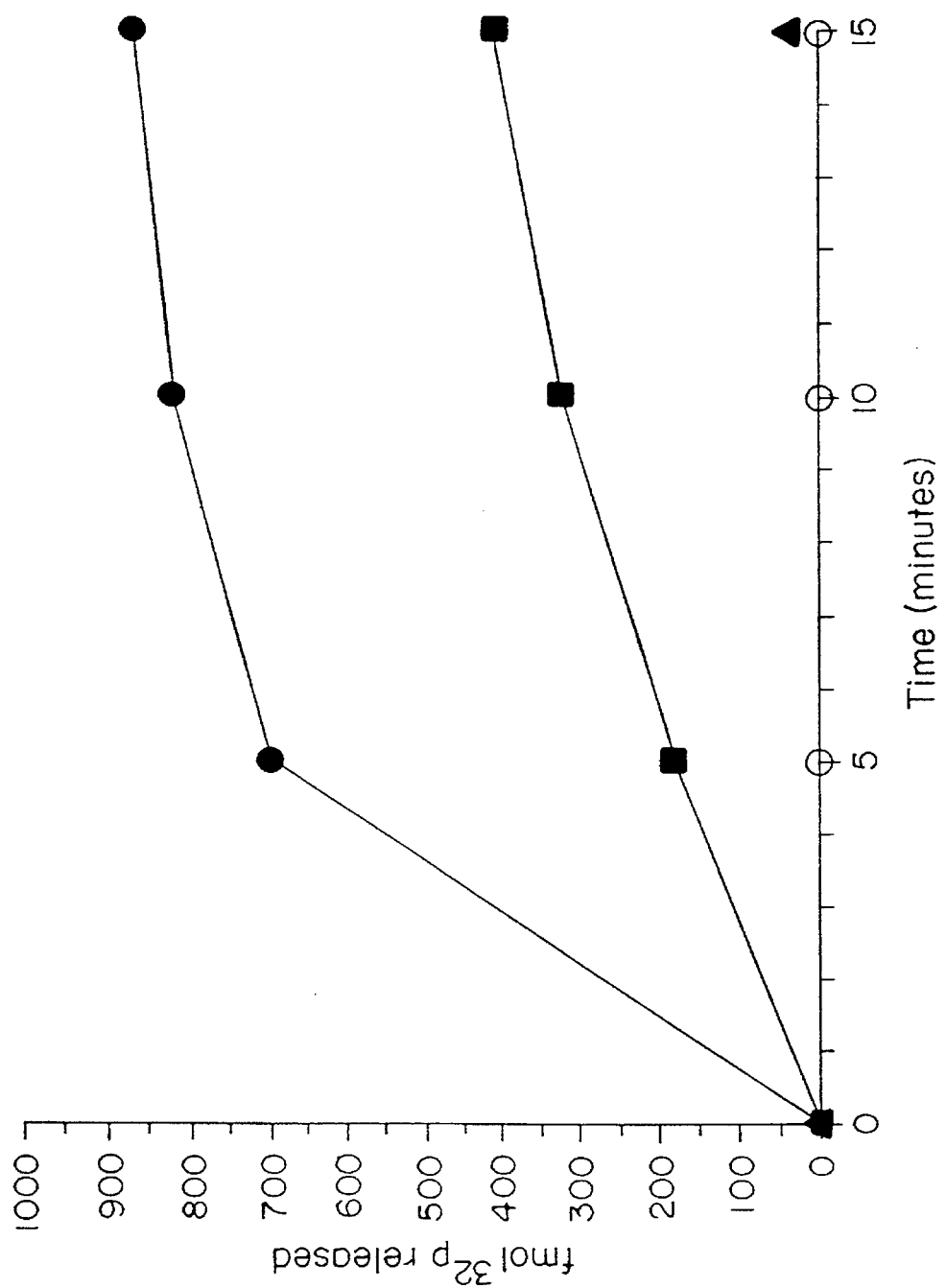
FIG. 8 is a graph illustrating the tyrosine-specific phosphatase activity of bacterially expressed SH-PTP2, and the time course of dephosphorylation of $^{32}$P-Raytide. Equal amounts of soluble protein from *E. coli* expressing GST or GST-SH-PTP2 (10 ng for GST (open circles), and 10 ng (closed circles) or 1 ng (closed squares) GST-SHPTP2) were incubated with 100 nM $^{32}$P-labeled Raytide. At the indicated times, the supernatant was assayed for release of $^{32}$P by a charcoal binding assay (57). GST-SH-PTP2-expressing lysates assayed in the presence of 100 mM $Na_3VO_4$ (closed triangle) or 50 mM NaF (open triangle) are indicated.

Equal amounts of protein from the bacteria expressing GST-SHPT-P2 or GST alone were assayed for PTP activity using radiolabeled Raytide. Raytide (Oncogene Science) was phosphorylated by recombinant p43$^{v-abl}$ (Oncogene Science) on its unique tyrosine as described (Plutzky, J., et al., *Proc. Natl. Acad. Sci. USA* 89:1123–1127 (1992)), using 67 μCi of [γ$^{32}$P]-ATP were used per 10 μg Raytide. PTP assays were conducted on soluble lysates from induced bacteria expressing GST-SH-PTP2 or GST alone using conditions described previously (Plutzky, J., et al., *Proc. Natl. Acad. Sci. USA* 89:1123–1127 (1992)). Under these conditions, substantially more GST than GST-SH-PTP2 is expressed as a percentage of total bacterial protein. GST-SHPTP2-expressing lysates showed substantially greater PTP activity than lysates expressing GST alone (FIG. 8). PTP activity was linear over time and proportional to protein concentration. As expected for a tyrosine phosphatase, this activity was blocked by the addition of 100 uM sodium vanadate, a potent tyrosine phosphatase inhibitor (FIG. 8, closed triangle), but was not affected by the addition of 50 mM sodium fluoride, a serine phosphatase inhibitor (FIG. 8, open triangle). Similar results were obtained when the respective fusion proteins were affinity purified on glutathione-agarose beads (data not shown).

EXAMPLE 4

Expression of SH-PTP2

Human genomic DNA (15 μg) was digested overnight with Bam HI, Bgl II, Eco RI, Hind III or Pst I (200 U), electrophoresed on a 0.8% agarose gel, and transferred to a charged nylon membrane (Magnagraph/MSI) for Southern blotting. Hybridization and high stringency washing conditions were as described previously (Gebert, J. F., et al., *Oncogene* 6:1859–68 (1991)); a partial SH-PTP2 cDNA corresponding to nucleotides 599 to 1881 was used as probe.

Southern blots of human genomic DNA hybridized with an SH-PTP2 partial cDNA indicated a complex pattern of bands (data not shown). The large number of bands observed with such a small part of the SH-PTP2 cDNA suggests either that SH-PTP2 is a large gene containing multiple introns, or that a family of highly related genes or pseudogenes exists. Consistent with the strong similarity between SH-PTP2 and csw, Southern analysis of genomic DNA from several other species indicates that SH-PTP2 is highly conserved (FIG. 4b).

A Northern blot of 2 μg poly A$^+$RNA from multiple human tissues (Clontech) was hybridized and washed similarly. For identification of SH-PTP2-related sequences in other species, genomic DNAs (10 μg) from chicken, human, rat, and mouse were digested with Bam HI, electrophoresed, and immobilized onto Zetabind (AMF/Cuno). To avoid detecting other PTPs, the probe utilized in this hybridization was a fragment corresponding to nucleotides 1 to 344, which lacks sequences from the phosphatase domain of SH-PTP2. Hybridization was for 18 hours at 65° C. as described (Gebert, J. F., et al., *Oncogene* 6:1859–68 (1991)). Reduced stringency washes were with 2×SSC, 0.2% SDS for 60 minutes at 40° C.

The Northern blot of RNA from various human tissues, including heart, brain, placenta, lung, liver, skeletal muscle, kidney and pancreas, indicated that SH-PTP1 is expressed as a 6 kb transcript (data not shown). Unlike SH-PTP1, which is found almost exclusively in hematopoietic cells, SH-PTP2 is expressed nearly ubiquitously. Notably, SH-PTP2 is expressed in many hematopoietic cells which also express SH-PTP1 (data not shown). Its ubiquitous expression, similar to csw (Perkins, L. A., et al., *Cell* 70:225–236 (1992)), is also consistent with the proposal that SH-PTP2 is the mammalian csw homolog.

EXAMPLE 5

Analysis of SH-PTP1 in Leukemia Patients

A primer set which amplifies the segment of DNA between nucleotides 500 and 730 of the SH-PTP1 cDNA was used to amplify the SH-PTP1 gene of a patient with acute lymphoblastic leukemia (ALL). Representative primers which can be used to amplify regions of the SH-PTP1 gene are shown in FIG. 9 (SEQ ID NO.: 41 through 54). Standard SH-PTP1 cDNA synthesis by reverse transcriptase, using standard conditions and oligo dT priming of RNA isolated from the patient was used, followed by polymerase chain reaction (PCR) using the same set of primers. PCR was carried out under standard conditions, except that $^{32}$PdCTP was included during the reaction to allow detection of the products by autoradiography. Following PCR, products were visualized by denaturing them at 94° C. and electrophoresis on a 5% non-denaturing acrylamide gel at 4° C. Detection revealed abnormalities consisting of significantly smaller bands.

Because of the abnormal bands, the entire SH-PTP1 cDNA was obtained by reverse transcription-PCR (RT-PCR) from the patient. Two products were noted: a normal product and a smaller product, the two differed by approximately 100 nucleotides on agarose gel electrophoresis. The ratio of the normal sized product to the smaller sized product was approximately 5:1. These products were cloned into a pGEM vector. Approximately 20% of the clones obtained contained the smaller (variant) product; the remaining clones were wild type in length. Both types of clone were subjected to sequence analysis using the primer set described above. The shorter clones were found to have a 117 nucleotide deletion compared to the wild type sequence. This deletion corresponded to nucleotides 537–653 of the SH-PTP1 cDNA sequence, which corresponds in the protein to roughly the second half of the second SH2 domain of SH-PTP1. The other clones were found to have wild type sequence.

To align the deleted sequence within the SH-PTP1 gene, the same primer set was used to prime a PCR reaction from the same patient's genomic DNA. This resulted in a product of approximately 600 nucleotides. This region was cloned into a plasmid vector and sequenced. Sequence analysis revealed the presence of three exons. The middle exon was 117 nucleotides in length and corresponded precisely to the deleted sequences in the shorter clones obtained above. Thus, these shorter clones, which represent at least 20% of the cDNAs from the patient, have sustained the loss of this exon.

Western blot analysis was used to investigate whether similar SH-PTP1 mutations occurred in other ALL patients. Approximately $5 \times 10^6$ cells from each of 30 patients were analyzed. Cells were pelleted and lysed in 1% NP40 buffer containing protease inhibitors and phosphatase inhibitors. Clarified lysates were boiled in SDS-PAGE sample buffer and electrophoresed on 10% SDS-PAGE gels. Proteins were immunoblotted onto Immobilon membranes and developed with anti-SH-PTP1 antibodies. To compare protein recovery between patients, the same immunoblot was probed with monoclonal anti-tubulin antibodies. The relative level of SH-PTP1 expression (as judged by the ratio of SH-PTP1/tubuline signal) was compared to the blast count (as assessed by FACS analysis for common acute lymphoblastic leukemia antigen (CALLA=CD10)).

Two types of potential abnormality were discerned. First, several patients had markedly lower levels (at least 10×lower) of SH-PTP1 protein compared with the other patients. There was no clear or consistent correlation between the percent of blasts (assessed by CALLA) and SH-PTP1 proteins; therefore, these differences in expression of SH-PTP1 can probably not be explained by differentiation-stage-specific differences in SH-PTP1 protein levels. Second, four patients displayed additional, smaller immunoreactive species with anti-SH-PTP1 antibodies. It is unlikely that the shorter species arose by proteolysis because all of the samples were prepared at the same time, using the same product; the sizes of the variant immunoreactive bands are different in different samples; and there was no evidence of tubulin proteolysis.

Equivalents

Those skilled in the art will recognize or be able to ascertain, using no more than routine experimentation, many equivalents to the specific embodiments of the invention described herein. Such equivalents are intended to be encompassed by the following claims.

---

We claim:

1. A method of detecting in a sample from an individual a chromosome 12p abnormality associated with neoplastic disease, comprising the steps of:
   (a) rendering nucleic acids in the sample available for hybridization;
   (b) contacting the nucleic acids of step (a) with a nucleic acid probe which only hybridizes to a nucleic acid fragment consisting of the sequence having nucleotides 537 to 653 shown in SEQ ID No.: 5, under stringency conditions which eliminate hybridization of the probe to extraneous nucleic acid sequences; and
   (c) detecting hybridization of the probe with nucleic acids in the sample;
wherein the absence of hydbridization is indicative of a chromosome 12p abnormality associated with neoplastic disease.

2. A method of detecting in a sample from an individual a abnormality in the SH-PTP1 gene associated with neoplastic disease, comprising the steps of:
   (a) rendering nucleic acids in the sample available for hybridization;
   (b) contacting the nucleic acids of step (a) with a nucleic acid probe which only hybridizes to a nucleic acid fragment consisting of the sequence having nucleotides 537 to 653 shown in SEQ ID No.: 5, under stringency conditions which eliminate hybridization of the probe to extraneous nucleic acid sequences; and
   (c) detecting the presence or absence of hybridization of the probe with nucleic acids in the sample;
wherein the absence of hybridization is indicative of an abnormality in the SH-PTP1 gene associated with neoplastic disease.

3. A method of detecting in a sample from an individual a chromosome 12p abnormality associated with neoplastic disease, comprising the steps of:
   (a) isolating the SH-PTP1 gene from the sample;
   (b) comparing the nucleic acid sequence of the SH-PTP1 gene from the sample to the nucleic acid sequence shown in SEQ ID NO.: 5,
wherein a difference between the sequence of the SH-PTP1 gene from the sample and the nucleic acid sequence shown in SEQ ID NO.: 5 is indicative of a chromosome 12p abnormality associated with neoplastic disease.

4. A method of detecting in a sample from an individual a chromosome 12p abnormality associated with neoplastic disease, comprising the steps of:
   (a) obtaining SH-PTP1 RNA from the sample;
   (b) generating SH-PTP1 cDNA by polymerase chain reaction; and
   (c) comparing the nucleic acid sequence of the SH-PTP1 cDNA to the nucleic acid sequence shown in SEQ ID NO.: 5,
wherein a difference between the sequence of the SH-PTP1 cDNA and the nucleic acid sequence shown in SEQ ID NO.: 5 is indicative of a chromosome 12p abnormality associated with neoplastic disease.

5. A method of detecting in a sample from an individual a abnormality in the SH-PTP1 gene associated with neoplastic disease, comprising the steps of:
   (a) isolating the SH-PTP1 gene from the sample;
   (b) comparing the nucleic acid sequence of the SH-PTP1 gene from the sample to the nucleic acid sequence shown in SEQ ID NO.: 5,
wherein a difference between the sequence of the SH-PTP1 gene from the sample and the nucleic acid sequence shown in SEQ ID NO.: 5 is indicative of an abnormality in the SH-PTP1 gene associated with neoplastic disease.

6. A method of detecting in a sample from an individual a abnormality in expression of the SH-PTP1 gene associated with neoplastic disease, comprising the steps of:

(a) obtaining SH-PTP1 RNA from the sample;

(b) generating SH-PTP1 cDNA by polymerase chain reaction; and (c) comparing the nucleic acid sequence of the SH-PTP1 cDNA to the nucleic acid sequence shown in SEQ ID NO.:5, wherein a difference between the sequence of the SHPTP1 cDNA and the nucleic acid sequence shown in SEQ ID NO.: 5 is indicative of an abnormality in expression of the SH-PTP1 gene associated with neoplastic disease.

7. The method of claim 6, wherein the difference between the sequence of the SH-PTP1 gene from the sample and the nucleic acid sequence shown in SEQ ID NO.: 5 is a deletion.

8. The method of claim 7, wherein the deletion is a deletion of all or a portion of the sequence encoding the first and/or second SH2 domains of said SH-PTP1 gene.

* * * * *